(12) United States Patent
George, Jr. et al.

(10) Patent No.: US 7,125,676 B2
(45) Date of Patent: Oct. 24, 2006

(54) EXPRESSION SYSTEM FOR HUMAN BRAIN-SPECIFIC VOLTAGE-GATED SODIUM CHANNEL, TYPE 1

(75) Inventors: Alfred L. George, Jr., Brentwood, TN (US); Christoph Lossin, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 342 days.

(21) Appl. No.: 10/374,954

(22) Filed: Feb. 25, 2003

(65) Prior Publication Data

US 2005/0260576 A1 Nov. 24, 2005

Related U.S. Application Data

(60) Provisional application No. 60/359,382, filed on Feb. 25, 2002.

(51) Int. Cl.
*G01N 33/53* (2006.01)
*G01N 33/566* (2006.01)
*C12N 5/10* (2006.01)
*C12N 15/12* (2006.01)
*C12N 15/63* (2006.01)

(52) U.S. Cl. ............... 435/7.1; 435/7.21; 435/69.1; 435/252.3; 435/320.1; 435/325; 436/501; 530/350; 536/23.1; 536/23.5

(58) Field of Classification Search ............... None
See application file for complete search history.

(56) References Cited

U.S. PATENT DOCUMENTS

| | | | |
|---|---|---|---|
| 5,670,622 A | 9/1997 | Shon et al. | |
| 5,688,830 A | 11/1997 | Berger et al. | |
| 5,776,859 A | 7/1998 | Nickel | |
| 5,780,242 A | 7/1998 | Nickel | |
| 5,858,687 A | 1/1999 | Manger et al. | |
| 5,892,018 A | 4/1999 | Welsh et al. | |
| 6,030,810 A | 2/2000 | Delgado et al. | |
| 6,030,974 A | 2/2000 | Schwartz et al. | |
| 6,060,271 A | 5/2000 | Walewski et al. | |
| 6,110,672 A | 8/2000 | Mandel et al. | |
| 6,110,937 A | 8/2000 | Loughhead et al. | |
| 6,172,085 B1 | 1/2001 | Ohkawa et al. | |
| 6,174,690 B1 | 1/2001 | Manger et al. | |
| 6,184,349 B1 | 2/2001 | Herman et al. | |
| 2002/0076780 A1 | 6/2002 | Turner, Jr. et al. | |
| 2004/0096885 A1* | 5/2004 | Rouleau et al. ............ 435/6 | |

FOREIGN PATENT DOCUMENTS

| | | |
|---|---|---|
| WO | WO 97/01577 | 1/1997 |
| WO | WO 97/42955 | 11/1997 |
| WO | WO 98/38302 | 9/1998 |
| WO | WO 98/43619 | 10/1998 |
| WO | WO 98/51290 | 11/1998 |
| WO | WO 99/47670 | 9/1999 |
| WO | WO 00/61188 | 10/2000 |
| WO | WO 00/61231 | 10/2000 |
| WO | WO 01/05831 A1 | 1/2001 |
| WO | WO 01/38564 A2 | 5/2001 |
| WO | WO 01/92304 A2 | 12/2001 |
| WO | WO 02/50096 A1 | 6/2002 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 492-495.*
Lossin et al., *Molecular Basis of an Inherited Epilepsy*, Neuron 34:877-884 (Jun. 13, 2002).
Abou-Khalil, *Partial and generalized epilepsy with febrile seizures plus and a novel SCN1A mutation*, Neurology 57:2265-2272 (2001).
Abdul et al., *Inhibition by Anticonvulsants of Prostate-specific Antigen and Interleukin-6 Secretion by Human Prostate Cancer Cells*, Anticancer Research 21:2045-2048 (2001).
Alekov et al., *A sodium channel mutation causing epilepsy in man exhibits subtle defects in fast inactivation and activation in vitro*, J. of Physiology 529(3):533-539 (2000).
Alekov et al., *Enhanced inactivation and acceleration of activation of the sodium channel associated with epilepsy in man*, European J. of Neuroscience 13:2171-2176 (2001).
Baekelandt et al., *Gene therapeutic strategies for neurodegenerative diseases*, Current Opinion in Molecular Therapeutics 2(5):540-554 (2000).
Baulac et al., *A Second Locus for Familial Generalized Epilepsy with Febrile Seizures Plus Maps to Chromosome 2q21-q33*, Am. J. Hum. Genet. 65:1078-1085 (1999).
Caron et al., *Adverse Effects of Class I Antiarrhythmic Drugs*, Drug Safety 1:8-36 (Jul. 1997).
Catterall, *From Ionic Currents to Molecular Mechanisms: The Structure and Function of Voltage-Gated Sodium Channels*, Neuron 26:13-25 (Apr. 2000).

(Continued)

*Primary Examiner*—Lorraine Spector
*Assistant Examiner*—Jon M. Lockard
(74) *Attorney, Agent, or Firm*—Jenkins, Wilson, Taylor & Hunt, P.A.

(57) ABSTRACT

Isolated nucleic acids encoding human SCN1A polypeptides, recombinantly expressed and isolated human SCN1A polypeptides, heterologous expression systems for recombinant expression of human SCN1A polypeptides, assay methods employing the same, and methods and compositions for modulation of sodium channel function.

31 Claims, 10 Drawing Sheets

OTHER PUBLICATIONS

Catterall, *Molecular Properties of Brain Sodium Channels: An Important Target for Anticonvulsant Drugs*, Advances in Neurology 79:441-456 (1999).

Claes et al., *De Novo Mutations in the Sodium-Channel Gene SCN1A Cause Severe Myoclonic Epilepsy of Infancy*, Am. J. Hum. Genet. 68:1327-1332 (2001).

Coulter, *Antiepileptic Drug Cellular Mechanisms of Action: Where Does Lamotrigine Fit In?* J. of Child Neurology 12(Supp 1):S2-S9 (Nov. 1997).

Diss et al., *Expression Profiles of Voltage-Gated $Na^+$ Channel α-Subunit Genes in Rat and Human Prostate Cancer Cell Lines*, The Prostate 48:165-178 (2001).

Duch et al., *Volatile anesthetics significantly suppress central and peripheral mammalian sodium channels*, Toxicology Letters 100-101:255-263 (1998).

Escayg et al., *Mutations of SCN1A, encoding a neuronal sodium channel, in two families with GEFS+2*, Nature Genetics 24:343-345 (Apr. 2000).

Escayg et al., *A Novel SCN1A Mutation Associated with Generalized Epilepsy with Febrile Seizures Plus-and Prevalence of Variants in Patients with Epilepsy*, Am. J. Hum. Genet. 68:866-873 (2001).

Goldin, *Diversity of Mammalian Voltage-Gated Sodium Channels*, Annals New York Academy of Sciences 40-50 (Date Unknown).

Hickenbottom et al., *Neuroprotective Therapy*, Seminars in Neurology 18(4):485-492 (1998).

Isom, *Pathobiology of Visceral Pain: Molecular Mechanisms and Therapeutic Implications I. Cellular and molecular biology of sodium channel β-subunits: therapeutic implications for pain?* Am. J. Physiol. Gastrointest. Liver Physiol. 278:G349-G353 (2000).

Lehmann-Horn et al., *Voltage-Gated Ion Channels and Hereditary Disease*, Physiological Reviews 79(4):1317-1372 (Oct. 1999).

Lu et al., *Differential expression of two sodium channel subtypes in human brain*, FEBS 303(1):53-58 (May 1992).

Malo et al., *Localization of a putative human brain sodium channel gene (SCN1A) to chromosome band 2q24*, Cytogenet Cell Genet 67:178-186 (1994).

Morgan et al., *β3: An additional auxiliary subunit of the voltage-sensitive sodium channel that modulates channel gating with distinct kinetics*, PNAS 97(5):2308-2313 (Feb. 29, 2000).

Noda et al., *Existence of distinct sodium channel messenger RNAs in rat brain*, Nature 320:188-192 (Mar. 13, 1996).

Noda et al., *Expression of functional sodium channels from cloned cDNA*, Nature 322:826-828 (Aug. 28, 1986).

Oh et al., *Novel splice variants of the voltage-sensitive sodium channel alpha subunit*, NeuroReport 9:1267-1272 (1998).

Peel et al., *Adeno-associated virus vectors: activity and applications in the CNS*, J. of Neuroscience Methods 98:95-104 (2000).

Sindrup et al., *Pharmacologic treatment of pain in polyneuropathy*, Neurology 55:915-920 (2000).

Wallace et al., *Neuronal Sodium-Channel α1-Subunit Mutations in Generalized Epilepsy with Febrile Seizures Plus*, Am. J. Human Genetics 68:859-865 (2001).

Waxman et al., *Voltage-gated sodium channels and the molecular pathogenesis of pain: A review*, J. of Rehab. Res. and Develop. 37:5 1-13 (Sep./Oct. 2000).

Whitaker et al., *Distribution of Voltage-Gated Sodium Channel α-Subunit and β-Subunit mRNAs in Human Hippocampal Formation, Cortex, and Cerebellum* J. of Compar. Neuro. 422:123-139 (2000).

\* cited by examiner

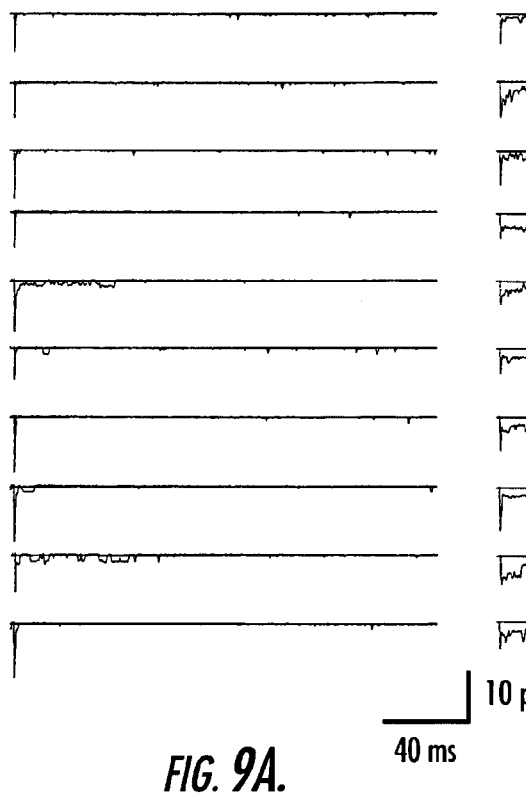
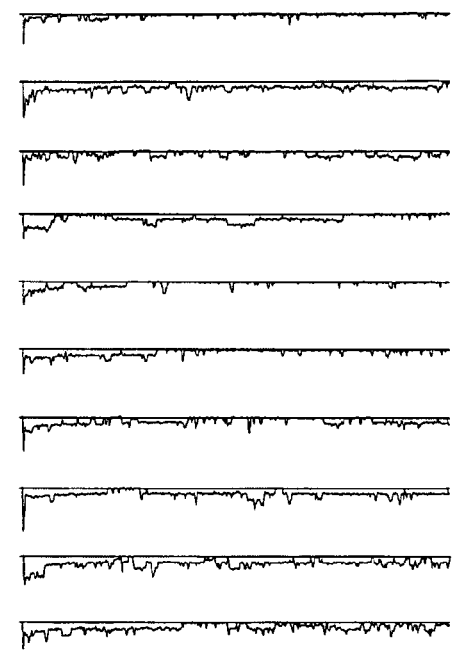
FIG. 9A.    FIG. 9B.
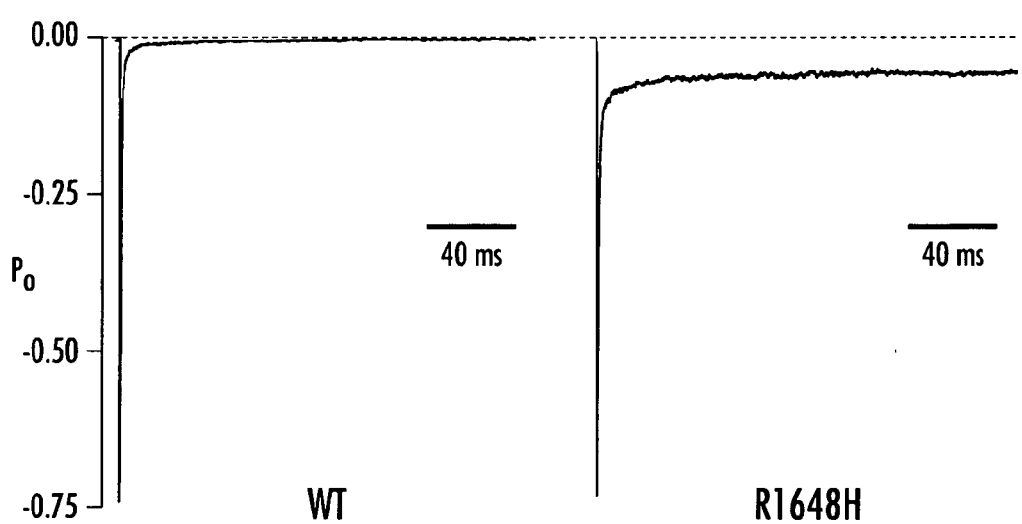
FIG. 9C.

EXPRESSION SYSTEM FOR HUMAN BRAIN-SPECIFIC VOLTAGE-GATED SODIUM CHANNEL, TYPE 1

CROSS REFERENCE TO RELATED APPLICATIONS

This application is based on and claims priority to U.S. Provisional Patent Application Ser. No. 60/359,382, filed Feb. 25, 2002, herein incorporated by reference in its entirety.

GRANT STATEMENT

This work was supported by grant NS32387 from the U.S. National Institute of Health. Thus, the U.S. government has certain rights in the invention.

FIELD OF THE INVENTION

The present invention generally relates to brain-specific voltage-gated sodium channel type 1 α-subunit genes and recombinant expression of the same. More particularly, the present invention provides isolated nucleic acids encoding human sodium channel type 1 α-subunit polypeptides, isolated human sodium channel type 1 α-subunit polypeptides, a heterologous expression system for recombinant expression of human sodium channel type 1 α-subunit polypeptides, methods for identifying modulators of a sodium channel, and uses thereof.

| Table of Abbreviations | |
|---|---|
| CMV | cytomegalovirus |
| COS | monkey cell line |
| CV-1 | monkey kidney cell line |
| EGFP | enhanced green fluorescent protein |
| Fab | antigen-binding antibody fragment |
| FCS | Fluorescence Correlation Spectroscopy |
| Fv | antigen-binding antibody fragment |
| GEFS+ | generalized epilepsy with febrile seizures plus |
| GFP | green fluorescent protein |
| HEK-293 | human embryonic kidney cell line |
| HeLa | human epithelial cell line |
| ORF | open reading frame |
| pCMV-SCN1A | construct encoding SCN1A (e.g. SEQ ID NO:3) under the control of a CMV promoter |
| PCR | polymerase chain reaction |
| PFU | plaque-forming unit |
| RACE | rapid amplification of cDNA ends |
| RT-PCR | reverse transcription - polymerase chain reaction |
| SCN1A | sodium channel type 1 alpha subunit |
| SCN1B | sodium channel beta 1 subunit |
| SCN2B | sodium channel beta 2 subunit |
| SCN3B | sodium channel beta 3 subunit |
| SELDI-TOF | Surface-Enhanced Laser Desorption/Ionization Time-Of-flight Spectroscopy |
| Sf9 | *Spodoptera frugiperda* cell line |
| SMEI | severe myoclonic epilepsy of infancy |
| SPR | surface plasmon resonance |
| tsA201 | human embryonic kidney cell line |
| TTX | tetrodotoxin |

BACKGROUND OF THE INVENTION

Voltage-sensitive ion channels are a class of transmembrane proteins that provide a basis for cellular excitability and the ability to transmit information via ion-generated membrane potentials. In response to changes in membrane potentials, these molecules mediate rapid ion flux through selective channels in a cell membrane. If channel density is high enough, a regenerative depolarization results, which is called an action potential.

The voltage-gated sodium channel is responsible for the generation and propagation of action potentials in most electrically excitable cells, including neurons, heart cells, and muscle. Electrical activity is triggered by depolarization of the membrane, which opens channels through the membrane that are highly selective for sodium ions. Ions are then driven intracellularly through open channels by an electrochemical gradient. Although sodium-based action potentials in different tissues are similar, electrophysiological studies have demonstrated that multiple structurally and functionally distinct sodium channels exist, and numerous genes encoding sodium channels have been cloned. The SCN1A gene belongs to a gene family of voltage-gated sodium channels.

There is a long standing need to diagnose and/or treat pathologies relating to impaired electrical excitability involving sodium channel dysfunction resulting from injury, genetic abnormalities, or disease states. In particular, sodium channel dysfunction is associated with epilepsy, convulsion, pain (including chronic pain), neuronal damage resulting from ischemia, and neuronal degeneration.

To address this need, the present invention provides in one embodiment a method for identifying molecules that specifically bind to a sodium channel and/or regulate sodium channel activity. The method employs a system for heterologous expression of a human sodium channel as disclosed herein.

SUMMARY OF INVENTION

The present invention provides an isolated human SCN1A polypeptide comprising: (a) a polypeptide comprising an amino acid sequence of SEQ ID NO:2; or (b) a polypeptide substantially identical to the polypeptide of SEQ ID NO:2. Also provided is an isolated human SCN1A polypeptide encoded by an isolated SCN1A nucleic acid disclosed herein.

Isolated nucleic adds encoding a recombinantly expressed human SCN1A polypeptide are also provided. A human SCN1A nucleic acid molecule comprises: (a) a nucleotide sequence comprising the nucleotide sequence of SEQ ID NO:1, further comprising one or more mutations, wherein the one or more mutations disrupt regions having a high spontaneous mutation rate; or (b) a nucleotide sequence substantially identical to SEQ ID NO:1, and further comprising one or more mutations, wherein the one or more mutations disrupt regions having a high spontaneous mutation rate. Preferably, a SCN1A nucleic acid that can be recombinantly expressed to produce a SCN1A polypeptide comprises: (a) a nucleic acid molecule comprising a nucleotide sequence of SEQ ID NO:3; or (b) a nucleic acid molecule substantially identical to SEQ ID NO:3, and wherein the nucleic acid molecule comprises a T→C transition at each of nucleotide positions 1206 and 1209 of SEQ ID NO:3.

The present invention further provides nucleic acids comprising the disclosed SCN1A nucleic acids operatively linked to a promoter. Preferably, such nucleic acids further comprise a vector that enables replication in a host cell, whereby a recombinant SCN1A polypeptide is produced. Preferred host cells also include but are not limited to mammalian cells, and more preferably human cells. In one embodiment, the host cells comprise a stable cell line.

Thus, the invention provides a system for heterologous expression of a human SCN1A polypeptide. In a preferred embodiment of the invention, the system comprises: (a) a recombinantly expressed human SCN1A polypeptide; and (b) a host cell comprising the recombinantly expressed human SCN1A polypeptide. Preferably, the recombinantly expressed human SCN1A polypeptide comprises a functional sodium channel.

In another preferred embodiment of the invention, a system for heterologous expression of a functional human SCN1A polypeptide comprises: (a) a construct comprising a nucleic acid molecule encoding a human SCN1A polypeptide operatively linked to a heterologous promoter; and (b) a host cell comprising the construct of (a), wherein the host cell expresses a human SCN1A polypeptide.

A system for heterologous expression of a SCN1A polypeptide can further comprise a host cell that expresses a sodium channel β-subunit polypeptide, preferably sodium channel β1 subunit. Optionally, the sodium channel β-subunit is recombinantly expressed.

Using the disclosed systems for heterologous expression of a SCN1A polypeptide, the present invention further provides a method for producing an antibody that specifically recognizes a sodium channel polypeptide. The method comprises: (a) recombinantly producing a human SCN1A polypeptide; (b) formulating the polypeptide of (a) whereby it is an effective immunogen; (c) administering to an animal the formulation of (b) to generate an immune response in the animal comprising production of antibodies, wherein antibodies are present in the blood serum of the animal; and (d) collecting the blood serum from the animal of (c) comprising antibodies that specifically bind to a sodium channel polypeptide. Also provided are antibodies produced by the method.

An antibody produced by the disclosed methods can be used to detect a sodium channel polypeptide in a sample, the method comprising: (a) obtaining a biological sample comprising peptidic material; (b) contacting the biological sample with an antibody that specifically binds a sodium channel polypeptide and that was produced according to the disclosed methods, wherein the antibody comprises a detectable label; and (c) detecting the detectable label, whereby a sodium channel polypeptide in a sample is detected.

A system for heterologous expression of a SCN1A polypeptide can also be used to identify sodium channel modulators. In one embodiment of the invention the method comprises: (a) providing a heterologous expression system whereby a human SCN1A polypeptide is expressed in a host cell; (b) providing a test substance to the system of (a); (c) assaying a level or quality of sodium channel function in the presence of the test substance; (d) comparing the level or quality of sodium channel function in the presence of the test substance with a control level or quality of sodium channel function; and (e) identifying a test substance as a modulator of a voltage-gated sodium channel function by determining a level or quality of sodium channel function in the presence of the test substance as significantly changed when compared to a control level or quality of sodium channel function.

In another embodiment of the invention, a method for identifying a sodium channel modulator comprises: (a) providing a heterologous expression system whereby a human SCN1A polypeptide is expressed in a host cell; (b) isolating the human SCN1A polypeptide; (c) exposing the isolated human SCN1A polypeptide to one or more test substances; (d) assaying binding of a test substance to the isolated human SCN1A polypeptide; and (e) selecting a candidate substance that demonstrates specific binding to the isolated human SCN1A polypeptide.

Sodium channel modulators, identified using the disclosed methods, can be used to detect a sodium channel polypeptide. The method comprises: (a) obtaining a biological sample comprising peptidic material; (b) contacting the biological sample with a sodium channel modulator, wherein the modulator comprises a detectable label; and (c) detecting the detectable label, whereby a sodium channel polypeptide in a sample is detected.

Also provided are modulators of sodium channel activity that are identified by the disclosed methods. Preferably, a sodium channel modulator of the invention comprises an anticonvulsant activity, an antiepileptic activity, a neuroprotective activity, a pain relief activity, and anesthetic, or combinations thereof.

The present invention further provides methods for modulating sodium channel activity in a subject. Preferably, the subject is a mammalian subject, and more preferably a human subject. Also preferably, the sodium channel activity that is altered in a subject comprises an activity of a human SCN1A polypeptide.

In one embodiment of the invention, a method for modulating sodium channel activity in a subject comprises: (a) preparing a pharmaceutical composition comprising a modulator identified according to the disclosed methods, and a carrier; (b) administering an effective dose of the pharmaceutical composition to a subject, whereby sodium channel activity is altered in the subject. Preferably, the subject is a mammal, and more preferably the subject is a human.

In another embodiment of the invention, a method for modulating sodium channel activity in a subject comprises: (a) preparing a gene therapy construct comprising a nucleotide sequence encoding a human SCN1A polypeptide, or a nucleotide sequence encoding a sodium channel modulator identified by the disclosed methods; and (b) administering the gene therapy construct to a subject, whereby the function of a sodium channel in the subject is modulated.

Accordingly, it is an object of the present invention to provide novel SCN1A nucleic acids and polypeptides, heterologous expression systems whereby a SCN1A polypeptide is expressed, methods and assays employing a heterologous SCN1A expression system, and methods for modulating and detecting a SCN1A polypeptide. This object is achieved in whole or in part by the present invention.

An object of the invention having been stated above, other objects and advantages of the present invention will become apparent to those skilled in the art after a study of the following description of the invention, Figures, and non-limiting Examples.

BRIEF DESCRIPTION OF THE DRAWINGS

FIG. 2A is a recording of whole-cell current (nA) measurements from a cell transfected with pCMV-SCN1A and when clamped at various step potentials as indicated in FIG. 2C. Currents were not normalized to cell capacitance.

FIG. 2B is a recording of whole-cell current (nA) measurements from a cell transfected with pCMV-SCN1A and a plasmid encoding human SCN1B, and when clamped at various step potentials as indicated in FIG. 2C. Currents were not normalized to cell capacitance.

FIG. 3A is a graph plotting normalized $Na^+$ current (pA/pF) as a function of clamp potential (mV). Peak currents were normalized to the cell's capacitance. (●) mean normalized current of 6 cells transfected with SCN1A; (○) mean normalized current of 6 cells co-transfected with SCN1A and SCN1B; error bars, standard error of the mean (SEM). The insert is a diagram of cell potential (mV), when cells were clamped to various step potentials for 20 milliseconds every 5 seconds.

FIG. 3B is a graph depicting normalized $Na^+$ current as a function of prepulse potential (mV). Currents were normalized to the peak current. Transfected cells display steady-state fast inactivation of the $Na^+$ current. (●) mean normalized current of 11 cells transfected with SCN1A; (○) mean normalized current of 16 cells co-transfected with SCN1A and SCN1B; error bars, SEM. The insert is a diagram of cell potential (mV), when cells were clamped to various step potentials for 20 milliseconds every 5 seconds.

FIG. 3C is a graph depicting normalized $Na^+$ current as a function of interpulse duration (milliseconds). Currents were normalized to the peak current measured during the conditioning pulse. Transfected cells display recovery from inactivation. (●) mean normalized current of 11 cells transfected with SCN1A; (○) mean normalized current of 16 cells co-transfected with constructs comprising SCN1A and SCN1B; error bars, SEM. The insert is a diagram of cell potential (mV), when cells were clamped at −10 mV for 500 milliseconds, allowed to recover for t seconds at −120 mV, then stepped to −10 mV for 20 milliseconds; Δt, interpulse duration. Current recorded during the second pulse was normalized to the current measured during the first pulse.

FIG. 4A, raw data; FIG. 4B, IV plot—peak currents were normalized to the cell's capacitance; FIG. 4C, Steady-state inactivation—currents were normalized to the overall peak current; FIG. 4D, recovery from inactivation—currents were normalized to the peak current measured during the conditioning pulse. Data is collected from n cells stemming from multiple transfections. Error bars indicate the standard error of the mean.

FIG. 5A, typical current tracings from a tsA201 cell transiently transfected with WT-SCN1A, hβ1 and hβ2 recorded at various test potentials between −80 and +50 mV (holding potential was −120 mV). FIG. 5B, current-voltage relationship for WT-SCN1A. Whole cell currents were normalized to cell capacitance (n=8 cells). FIG. 5C, Voltage dependence of sodium channel availability and activation. The voltage dependence of sodium channel availability ("steady-state inactivation") was obtained using a standard double pulse protocol indicated as an inset. The membrane potential for half-inactivation was −67.5±2.3 mV, with a slope factor of −6.2±0.3 mV (n=9). The voltage dependence of channel activation curve was estimated by measuring peak sodium current following a variable test potential from a holding potential of −120 mV. The current at each membrane potential was divided by the electrochemical driving force for sodium ions, $V_m - V_{Na}$ ($V_{Na}$ represents the sodium equilibrium potential) and normalized to the maximum sodium conductance. FIG. 5D, time course of recovery from inactivation at −120 mV. The pulse protocol for measuring recovery from inactivation is shown as an inset. The time constants and fractional amplitudes (given in parentheses) are as follows: τ1=6.4±1.3 ms (71.0±3.0%), τ2=263±36 ms (29.0±3.0%), n=9.

FIG. 6D depicts representative WT-SCN1A, R1648H, T875M and W1204R sodium channel recordings in the absence and presence of 10 μM TTX. Sodium current was elicited by a 100 ms depolarization from −120 to −10 mV. TTX-sensitive currents were obtained by digital subtraction of sodium currents recorded before and after TTX. Sodium currents were normalized to their peak values. Zero current level is indicated by a dotted line. The inset shows an expanded Y-axis scale to emphasize the relative proportion of non-inactivating currents.

FIG. 8A, current-voltage relationships of WT-SCN1A (solid circle), R1648H (open diamond), T875M (open triangle) and W1204R (open square)—whole cell currents were normalized to cell capacitance (n=8–19 cells). FIG. 8B, voltage-dependence of fast inactivation time constants for WT and mutant channels. FIG. 8C, voltage dependence of sodium channel availability and activation. The pulse protocol is shown as an inset. The membrane potentials for half-maximal inactivation and slope factors were as follows (values for WT-SCN1A given in FIGS. 5A–5D legend): R1648H, −69.1±2.1 mV and −6.5±0.4 mV, n=10; T875M, −60.7±1.1 mV (p<0.01 vs WT-SCN1A) and −5.9±0.6 mV, n=13; W1204R, −72.0±2.0 mV and −6.9±0.4 mV, n=7. The voltage dependence of channel activation curve was constructed as described in the legend of FIGS. 5A–5D. FIG. 8D, recovery from inactivation assessed with the same pulse protocol shown in FIG. 5D. The time constants and fractional amplitudes (given in parentheses) are as follows (values for WT-SCN1A given in FIGS. 5A–5D legend): R1648H, τ1=3.1±0.2 ms (59.9±3.9%), τ2=257±36 ms (40.1±3.9%), n=9 (p<0.05 for τ1 and fractional amplitudes); T875M, τ1=4.6±0.5 ms (54.8±4.9%), τ2=680±151 ms (45.2±4.9%), n=10 (p<0.05 for τ2 and fractional amplitudes); W1204R, τ1=5.3±0.5 ms (67.5±2.3%), τ2=244±31 ms (32.5±2.3%), n=8.

FIGS. 9A–9C depict single-channel recordings of WT-SCN1A and R1648H. Representative single-channel traces recorded in outside-out membrane patches excised from tsA201 cells transiently transfected with WT-SCN1A (FIG. 9A) or R1648H (FIG. 9B) plus both β1 and β2 subunits. Channel openings are in the downward direction and solid horizontal lines indicate zero-current level. Channel activity was measured for 250 ms at 0 mV from a holding potential of −100 mV. FIG. 9C depicts ensemble average currents for WT-SCN1A and R1648H reconstructed from single channel data. Four independent experiments for each channel allele (100 sweeps per experiment) were averaged. The vertical axis depicts open probability ($P_o$) obtained by dividing the ensemble average current by the unitary current (~1 pA) and the number of channels per patch. The number of channels per patch was calculated by dividing the largest current peak measured during 100 sweeps by the unitary conductance.

BRIEF DESCRIPTION OF SEQUENCES IN THE SEQUENCE LISTING

Figure 1:
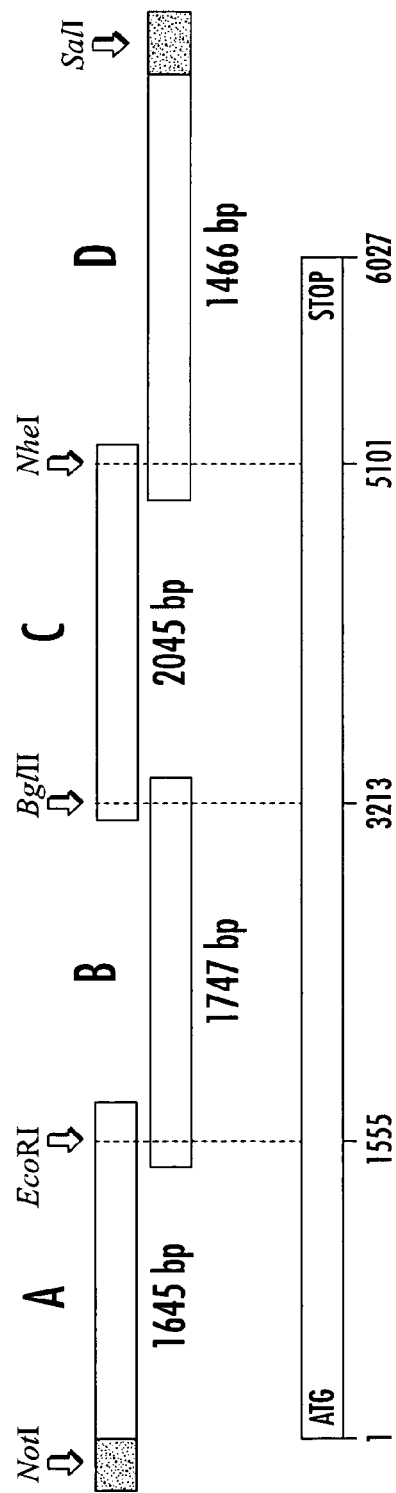
FIG. 1 is a schematic diagram depicting the strategy used to isolate a full-length SCN1A cDNA (SEQ ID NO:1). The lower bar represents the open reading frame (ORF) of SCN1A, beginning at nucleotide 1 as indicated by numbers below the bar. "ATG" indicates the start codon, and "Stop" indicates the stop codon. Bars aligned above the ORF bar represent PCR products comprising partial SCN1A cDNAs. The bar labeled "A" represents a product amplified using primers set forth as SEQ ID NOs:10–11, bar "B" represents a product amplified using primers set forth as SEQ ID NOs: 12–13, bar "C" represents a product amplified using primers set forth as SEQ ID NOs: 14–15, and bar "D" represents a product amplified using primers set forth as SEQ ID NOs: 16–17. Partial cDNA "D" includes sequences comprising 3' untranslated region corresponding to a length of the bar not overlapping with the ORF bar below. Dashed vertical lines indicate the positions of three unique restriction sites (EcoRI, BglII, and NheI) that were used for assembly of the full-length clone. Gray regions of bar A and bar D represent additional sequences comprising restriction sites (NotI and SalI, respectively) to facilitate directional cloning of the full-length SCN1A cDNA. See Example 1.

SEQ ID NOs:1 and 3 are native and modified nucleotide sequences, respectively, that each encode human SCN1A protein as set forth in SEQ ID NO:2.

Even-numbered SEQ ID NOs:4–8 are nucleotide sequences described in Table 1. Odd-numbered SEQ ID NOs:5–9 are amino acid sequences encoded by the immediately preceding nucleotide sequence, e.g. SEQ ID NO:5 is the protein encoded by the nucleotide sequence of SEQ ID NO:4, SEQ ID NO:7 is the protein encoded by the nucleotide sequence of SEQ ID NO:6, etc.

SEQ ID NOs:10–19 are PCR primers and primer subsequences.

SEQ ID NOs: 20–23 are two SCN1A splice variants (cDNAs are SEQ ID NOs:20 and 22; amino acids sequences SEQ ID NOs:21 and 23, respectively). Both variants result from utilization of alternative splice donor sequences contained within exon 11 and produce in frame deletions of 33 and 84 nucleotides from the 3' end of this exon (encoding the cytoplasmic region between domains I and II).

SEQ ID NO:24 is the 33 nucleotide sequence missing in one SCN1A splice variant cDNA (SEQ ID NO: 20).

SEQ ID NO:25 is the 11 amino acid sequence missing in the splice variant protein of SEQ ID NO: 21.

SEQ ID NO:26 is the 84 nucleotide sequence missing in one SCN1A splice variant cDNA (SEQ ID NO: 22).

SEQ ID NO:27 is the 28 amino acid sequence missing in the splice variant protein of SEQ ID NO: 23.

TABLE 1

Sequence Listing Summary

| SEQ ID NO. | description |
| --- | --- |
| 1 | human SCN1A native cDNA |
| 2 | human SCN1A protein |
| 3 | human SCN1A modified cDNA |
| 4 | human SCN1B cDNA |
| 5 | human SCN1B protein |
| 6 | human SCN2B cDNA |
| 7 | human SCN2B protein |
| 8 | human SCN3B cDNA |
| 9 | human SCN3B protein |
| 10 | primer AF |
| 11 | primer AR |
| 12 | primer BF |
| 13 | primer BR |
| 14 | primer CF |
| 15 | primer CR |
| 16 | primer DF |
| 17 | primer DR |
| 18 | forward primer 5' extension |
| 19 | reverse primer 5' extension |
| 20 | SCN1A splice variant cDNA 33N: SCN1AΔn2011–2043 Δn2011–2043 = missing NUCLEOTIDES |
| 21 | SCN1A splice variant protein 33P: SCN1AΔp671–681 (Translation of SCN1AΔn2011–2043) Δp671–681 = missing AMINO ACIDS |
| 22 | SCN1A splice variant cDNA 84N: SCN1AΔn1960–2043 Δn1960–2043 = missing NUCLEOTIDES |
| 23 | 84P: SCN1AΔp654–681 Translation of SCN1AΔn1960–2043 Δp654–681 = missing AMINO ACIDS |
| 24 | Δn33 |
| 25 | Δp11 |
| 26 | Δn84 |
| 27 | Δp28 |

DETAILED DESCRIPTION OF THE INVENTION

I. Definitions

While the following terms are believed to be well understood by one of ordinary skill in the art, the following definitions are set forth to facilitate explanation of the invention.

The terms "naturally occurring" or "native", as used herein to describe a nucleic acid or polypeptide, each refer to a composition that can be found in nature as distinct from being artificially produced or isolated by man. Generally, a native sequence refers to a functional unit, for example, an open reading frame. Thus, a nucleotide or amino acid sequence present in an organism, which can be isolated from a source in nature and which has not been intentionally modified by man in the laboratory, is naturally occurring.

The term "isolated", as used in the context of a nucleic acid or polypeptide, indicates that the nucleic acid or polypeptide exists apart from its native environment and is not a product of nature. An isolated nucleic acid or polypeptide can exist in a purified form or can exist in a non-native environment such as a transgenic host cell.

The term "about", as used herein when referring to a measurable value such as a percentage of sequence identity (e.g., when comparing nucleotide and amino acid sequences as described herein below), a size a length, etc. is meant to encompass variations of ±20% or ±10%, more preferably ±5%, even more preferably ±1%, and still more preferably ±0.1% from the specified amount, as such variations are appropriate to perform the disclosed method.

II. Novel Human SCN1A Nucleic Acids

The present invention provides novel nucleotide sequences encoding a human sodium channel type 1 alpha subunit (SCN1A) polypeptide. The term "SCN1A" is used herein to refer to nucleic acids that encode a sodium channel type 1 alpha subunit polypeptide. The term "SCN1A" also refers to nucleic adds encoding a voltage-gated brain-specific sodium channel. The term "SCN1A" also refers generally to polypeptides encoded by SCN1A nucleic acids, and activities thereof.

Representative methods for cloning and modifying a full-length human SCN1A cDNA are described in the Examples. The novel nucleic acids comprise an isolated and mutagenized SCN1A cDNA (SEQ ID NO:3) that harbors two silent mutations. The mutations comprise T to C transitions at nucleotide positions 1206 and 1209 of a full-length SCN1A cDNA, and are referred to herein as "T1206C" and "T1209C", respectively. The novel nucleic acids can further comprise splice variants, as disclosed in the Examples and in SEQ ID NOs:20–23, and the definitions, sequence comparison, and hybridization conditions set forth herein are equally applicable to the splice variants.

The modified SCN1A cDNA comprises mutations that enable stable replication in vitro. Recombinant, non-mutagenized SCN1A cDNA (SEQ ID NO:1) displayed spontaneous mutagenesis, preventing assembly of full length SCN1A cDNA. A short poly-T region exhibiting spontaneous mutations in the full-length construct was interrupted by the introduction of two silent T to C mutations at ORF positions 1206 and 1209. All full-length constructs were successfully propagated in STBL2 cells (Life Technologies) grown at 30° C. for >48 hours.

Thus, the term "modified SCN1A", as used herein to describe an mutagenized SCN1A that can be recombinantly expressed, refers to isolated nucleic acids of the present invention comprising: (a) a nucleotide sequence comprising the nucleotide sequence of SEQ ID NO:1, further comprising one or more mutations, wherein the one or more mutations retard or even prevent spontaneous mutation; or (b) a nucleotide sequence substantially identical to SEQ ID NO:1, further comprising one or more mutations, wherein the one or more mutations retard or even prevent spontaneous mutation. Preferably, the mutations are silent mutations. More preferably, a SCN1A nucleic acid that can be recombinantly expressed to produce a SCN1A polypeptide comprises: (a) a nucleic acid molecule comprising a nucleotide sequence of SEQ ID NO:3; or (b) a nucleic acid molecule that is substantially identical to SEQ ID NO:3, and wherein the nucleic acid molecule comprises a T to C transition at each of nucleotide positions 1206 and 1209 of SEQ ID NO:3.

The term "modified SCN1A" also encompasses nucleic acids comprising subsequences and elongated sequences of a modified SCN1A nucleic acid, nucleic acids complementary to a modified SCN1A nucleic acid, and RNA molecules corresponding to a modified SCN1A nucleic acid. Also included are chimeric genes and vectors comprising the disclosed modified SCN1A nucleotide sequences. In addition, the term "modified SCN1A nucleic acid" excludes nucleotide sequences created by introducing SCN1A-like mutations into nucleic acids encoding other sodium channel proteins.

The terms "nucleic acid molecule" or "nucleic acid" each refer to deoxyribonucleotides or ribonucleotides and polymers thereof in single-stranded, double-stranded, or triplexed form. Unless specifically limited, the term encompasses nucleic acids containing known analogues of natural nucleotides that have similar properties as the reference natural nucleic acid. The terms "nucleic acid molecule" or "nucleic acid" can also be used in place of "gene", "cDNA", or "mRNA". Nucleic acids can be synthesized, or can be derived from any biological source, including any organism.

The term "substantially identical", as used herein to describe a degree of similarity between nucleotide sequences, refers to two or more sequences that have at least about least 60%, preferably at least about 70%, more preferably at least about 80%, more preferably about 90% to about 99%, still more preferably about 95% to about 99%, and most preferably about 99% nucleotide identity, when compared and aligned for maximum correspondence, as measured using one of the following sequence comparison algorithms (described herein below under the heading "Nucleotide and Amino Acid Sequence Comparisons" or by visual inspection. Preferably, the substantial identity exists in nucleotide sequences of at least about 100 residues, more preferably in nucleotide sequences of at least about 150 residues, and most preferably in nucleotide sequences comprising a full length coding sequence. The term "full length", as used herein to refer to a complete open reading frame encoding a functional SCN1A polypeptide, comprises a nucleotide sequence encoding a peptide having 2009 amino acids (SEQ ID NO:2).

In one aspect, polymorphic sequences can be substantially identical sequences. The term "polymorphic" refers to the occurrence of two or more genetically determined alternative sequences or alleles in a population. An allelic difference can be as small as one base pair.

In another aspect, substantially identical sequences can comprise mutagenized sequences, including sequences comprising silent mutations. A mutation can comprise a single base change.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

A preferred nucleotide sequence employed for hybridization studies or assays includes probe sequences that are complementary to or mimic at least an about 14 to 40 nucleotide sequence of a nucleic acid molecule of the present invention. Preferably, probes comprise 14 to 20 nucleotides, or even longer where desired, such as 30, 40, 50, 60, 100, 200, 300, or 500 nucleotides or up to the full length of any one of SEQ ID NOs:1, 3, 4, 6, and 8. Such fragments can be readily prepared by, for example, chemical synthesis of the fragment, by application of nucleic acid amplification technology, or by introducing selected sequences into recombinant vectors for recombinant production.

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes,* part 1 chapter 2, Elsevier, New York, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook et al., eds (1989) *Molecular Cloning: A Laboratory Manual,* Cold Spring Harbor Laboratory Press, Cold Spring Harbor, N.Y. for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1M $Na^+$ ion, typically about 0.01 to 1M $Na^+$ ion concentration (or other salts) at pH 7.0–8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to identify nucleotide sequences that are substantially identical to reference nucleotide sequences of the present invention: a probe nucleotide sequence preferably hybridizes to a target nucleotide sequence in 7% sodium dodecyl sulfate (SDS), 0.5M $NaPO_4$, 1 mM EDTA at 50° C. followed by washing in 2×SSC, 0.1% SDS at 50° C.; more preferably, a probe and target sequence hybridize in 7% sodium dodecyl sulfate (SDS), 0.5M $NaPO_4$, 1 mM EDTA at 50° C. followed by washing in 1×SSC, 0.1% SDS at 50° C.; more preferably, a probe and target sequence hybridize in 7% sodium dodecyl sulfate (SDS), 0.5M $NaPO_4$, 1 mM EDTA at 50° C. followed by washing in 0.5×SSC, 0.1% SDS at 50° C.; more preferably, a probe and target sequence hybridize in 7% sodium dodecyl sulfate (SDS), 0.5M $NaPO_4$, 1 mM EDTA at 50° C. followed by washing in 0.1×SSC, 0.1% SDS at 50° C.; more preferably, a probe and target sequence hybridize in 7% sodium dodecyl sulfate (SDS), 0.5M $NaPO_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three dimensional structure, or are biologically functional equivalents. These terms are defined further under the heading "SCN1A Polypeptides" herein below. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues. See Batzer et al. (1991) *Nucleic Acids Res* 19:5081; Ohtsuka et al. (1985) *J Biol Chem* 260:2605–2608; Rossolini et al. (1994) *Mol Cell Probes* 8:91–98

The term "subsequence" refers to a sequence of nucleic acids that comprises a part of a longer nucleic acid sequence. An exemplary subsequence is a probe, described herein above, or a primer. The term "primer" as used herein refers to a contiguous sequence comprising about 8 or more deoxyribonucleotides or ribonucleotides, preferably 10–20 nucleotides, and more preferably 20–30 nucleotides of a selected nucleic acid molecule. The primers of the invention encompass oligonucleotides of sufficient length and appropriate sequence so as to provide initiation of polymerization on a nucleic acid molecule of the present invention.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The term "complementary sequences", as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

The term "gene" refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The present invention also encompasses chimeric genes comprising the disclosed SCN1A nucleotide sequences. The term "chimeric gene", as used herein, refers to a promoter region operatively linked to a SCN1A sequence, including a SCN1A cDNA, a SCN1A antisense RNA molecule, a SCN1A RNA molecule having tertiary structure, such as a hairpin structure, or a SCN1A double-stranded RNA molecule.

The term "operatively linked", as used herein, refers to a functional combination between a promoter region and a nucleotide sequence such that the transcription of the nucleotide sequence is controlled and regulated by the promoter region. Techniques for operatively linking a promoter region to a nudeotide sequence are known in the art.

The term "recombinant" generally refers to an isolated nucleic acid that is replicable in a non-native environment. Thus, a recombinant nucleic acid can comprise a non-replicable nucleic acid in combination with additional nucleic acids, for example vector nucleic acids, that enable its replication in a host cell.

The term "vector" is used herein to refer to a nucleic acid molecule having nucleotide sequences that enable its replication in a host cell. A vector can also include nucleotide sequences to permit ligation of nucleotide sequences within the vector, wherein such nucleotide sequences are also replicated in a host cell. Representative vectors include plasmids, cosmids, and viral vectors. A vector can also mediate recombinant production of a SCN1A polypeptide, as described further herein below.

The term "construct", as used herein to describe an expression construct, refers to a vector further comprising a nucleotide sequence operatively inserted with the vector, such that the nucleotide sequence is expressed.

The terms "recombinantly expressed" or "recombinantly produced" are used interchangeably to generally refer to the process by which a polypeptide encoded by a recombinant nucleic acid is produced.

The term "heterologous nucleic acids" refers to a sequence that originates from a source foreign to an intended host cell or, if from the same source, is modified from its original form. Thus, a heterologous nucleic acid in a host cell includes a gene that is endogenous to the particular host cell but has been modified, for example by mutagenesis or by isolation from native cis-regulatory sequences. The term "heterologous nucleic acid" also includes non-naturally occurring multiple copies of a native nucleotide sequence. The term "heterologous nucleic acid" also encompasses a nucleic acid that is incorporated into a host cell's nucleic acids, however at a position wherein such nucleic acids are not ordinarily found. A representative heterologous nucleic acid comprises a recombinant nucleic acid.

The term "heterologous expression system" refers to a host cell comprising a heterologous nucleic acid and the polypeptide encoded by the heterologous nucleic acid. For example, a heterologous expression system can comprise a host cell transfected with a construct comprising a recombinant nucleic acid, or a cell line produced by introduction of heterologous nucleic adds into a host cell genome.

Nucleic acids of the present invention can be cloned, synthesized, recombinantly altered, mutagenized, or combinations thereof. Standard recombinant DNA and molecular cloning techniques used to isolate nucleic acids are known in the art. Exemplary, non-limiting methods are described by site-specific mutagenesis to create base pair changes, deletions, or small insertions are also known in the art as exemplified by publications. See e.g., Sambrook et al. (eds.) (1989) *Molecular Cloning: A Laboratory Manual.* Cold Spring Harbor Laboratory Press, Cold Spring Harbor; Silhavy et al. (1984) *Experiments with Gene Fusions.* Cold Spring Harbor Laboratory, Cold Spring Harbor, N.Y.; Glover & Hames (1995) *DNA Cloning: A Practical Approach,* 2nd ed. IRL Press at Oxford University Press, Oxford/New York; Ausubel (ed.) (1995) *Short Protocols in Molecular Biology,* 3rd ed. Wiley, N.Y.

III. SCN1A Polypeptides

A voltage-gated sodium channel comprises a single polypeptide containing four internal repeats, or homologous domains (I–IV), having similar amino acid sequences. Each domain folds into six predicted transmembrane α-helices or segments: five are hydrophobic segments and one is highly charged with many arginine and lysine residues. This highly charged segment is the fourth transmembrane segment in each domain and is involved in voltage-sensing. The positively charged side chains on the S4 segment are likely to be paired with the negatively charged side chains on the other five segments such that membrane depolarization could shift the position of one helix relative to the other, thereby mediating the opening of the channel.

The present invention provides a SCN1A polypeptide encoded by a modified SCN1A nucleic acid, wherein the modified SCN1A nucleic acid shows improved stability and levels for recombinant gene expression. Thus, the present invention provides a recombinantly expressed and isolated SCN1A polypeptide. The terms "SCN1A polypeptide" and "SCN1A protein" each refer to protein comprising: (a) an amino acid sequence of SEQ ID NO:2; or (2) an amino acid sequence substantially identical to SEQ ID NO:2, as described herein below.

The term "substantially identical", as used herein to describe a level of similarity between SCN1A and a protein substantially identical to SCN1A, refers to a sequence that is at least 85% identical to SEQ ID NO:1 or 3, when compared over the full length of the SCN1A protein. Preferably, a protein substantially identical to SCN1A comprises an amino acid sequence that is 85% to about 90% identical to SEQ ID NO:1 or 3 when compared over the full length of the SCN1A protein, more preferably about 90% to about 95% identical to SEQ ID NO:1 or 3 when compared over the full length of the SCN1A protein, and even more preferably about 95% to about 99% identical to SEQ ID NO:1 or 3 when compared over the full length of the SCN1A protein. The term "full length", as used herein to describe a functional SCN1A polypeptide, comprises an amino acid sequence having 2009 amino acids (SEQ ID NO:2). Methods for determining percent identity are defined herein below under the heading "Nucleotide and Amino Acid Sequence Comparisons".

Substantially identical polypeptides also encompass two or more polypeptides sharing a conserved three-dimensional structure. Computational methods can be used to compare structural representations, and structural models can be generated and easily tuned to identify similarities around important active sites or ligand binding sites. See Saqi et al. (1999) *Bioinformatics* 15:521–522; Barton (1998) *Acta*

*Crystallogr D Biol Crystallogr* 54:1139–1146; Henikoff et al. (2000) *Electrophoresis* 21:1700–1706; Huang et al. (2000) *Pac Symp Biocomput*:230–241.

Substantially identical proteins also include proteins comprising an amino acid sequence comprising amino acids that are functionally equivalent to amino acids of SEQ ID NO:2. The term "functionally equivalent" in the context of amino acid sequences is known in the art and is based on the relative similarity of the amino acid side-chain substituents. See Henikoff & Henikoff (2000) *Adv Protein Chem* 54:73–97. Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape. By this analysis, described further herein below, arginine, lysine, and histidine; alanine, glycine, and serine; and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101 describes that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

The term "substantially identical" also encompasses polypeptides that are biologically functional equivalents. The term "functional" includes activity of an SCN1A polypeptide in allowing $Na^+$ ion flux across a membrane, referred to as permeation. Preferably, the term "functional" also refers to similar kinetics of activation and inactivation of $Na^+$ permeation. Methods for assessing sodium channel function are described herein below.

The present invention also provides functional fragments of a SCN1A polypeptide. Such functional portion need not comprise all or substantially all of the amino acid sequence of a native SCN1A gene product.

The present invention also includes functional polypeptide sequences that are longer sequences than that of a native SCN1A polypeptide. For example, one or more amino acids can be added to the N-terminus or C-terminus of a sodium channel subunit polypeptide. Methods of preparing such proteins are known in the art.

IV. Nucleotide and Amino Acid Sequence Comparisons

The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain biological activity of a gene, gene product, or sequence of interest. The terms "nucleotide sequence substantially similar to SCN1A" and "protein substantially similar SCN1A" are described herein above.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith & Waterman (1981) *Adv Appl Math* 2:482–489, by the homology alignment algorithm of Needleman & Wunsch (1970) *J Mol Biol* 48:443–453, by the search for similarity method of Pearson & Lipman (1988) *Proc Natl Acad Sci USA* 85:2444–2448, by computerized implementations of these algorithms (GAP, BESTFIT, FASTA, and TFASTA in the Wisconsin Genetics Software Package, Genetics Computer Group, Madison, Wis.), or by visual inspection. See generally, Ausubel (ed.) (1995) *Short Protocols in Molecular Biology*, 3rd ed. Wiley, N.Y.

A preferred algorithm for determining percent sequence identity and sequence similarity is the BLAST algorithm, which is described in Altschul et al. (1990) *J Mol Biol* 215:403–410. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff (1992) *Proc Natl Acad Sci U S A* 89:10915–10919.

In addition to calculating percent sequence identity, the BLAST algorithm also performs a statistical analysis of the similarity between two sequences. See e.g., Karlin & Altschul (1993) *Proc Natl Acad Sci U S A* 90:5873–5877. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

V. System for SCN1A Expression

The present invention further provides a system for heterologous expression of a functional human SCN1A polypeptide. Preferably, the recombinantly expressed human SCN1A polypeptide comprises a functional sodium channel. Thus, a recombinantly expressed SCN1A polypeptide preferably displays voltage-gated ion conductance across a lipid bilayer or membrane. Also preferably, a recombinant SCN1A polypeptide shows activation and inactivation kinetics similar to a native SCN1A polypeptide. Example 4 describes representative electrophysiological methods to assess SCN1A function.

In one embodiment of the invention, a system for heterologous expression of a functional human SCN1A polypeptide comprises: (a) a recombinantly expressed SCN1A polypeptide; and (b) a host cell comprising the recombinantly expressed human SCN1A polypeptide.

In another embodiment of the invention, a system for heterologous expression of a functional human SCN1A polypeptide comprises: (a) a vector comprising a nucleic acid molecule encoding a human SCN1A polypeptide operatively linked to a heterologous promoter; and (b) a host cell comprising the vector of (a), wherein the host cell expresses a human SCN1A.

As described herein above, a construct for expression of a SCN1A polypeptide includes a vector and a SCN1A nucleotide sequence, wherein the SCN1A nucleotide sequence is operatively linked to a promoter sequence. Recombinant production of a SCN1A polypeptide can be directed using a constitutive promoter or an inducible promoter. Exemplary promoters include Simian virus 40 early promoter, a long terminal repeat promoter from retrovirus, an actin promoter, a heat shock promoter, and a metallothien protein. Suitable vectors that can be used to express a SCN1A polypeptide include but are not limited to viruses such as vaccinia virus or adenovirus, baculovirus vectors, yeast vectors, bacteriophage vectors (e.g., lambda phage), plasmid and cosmid DNA vectors, transposon-mediated transformation vectors, and derivatives thereof. A construct for recombinant SCN1A expression can also comprise transcription termination signals and sequences required for proper translation of the nucleotide sequence. Addition of such sequences is known to one of skill in the art.

In a preferred embodiment of the invention, a construct for recombinant expression of a SCN1A polypeptide comprises a plasmid vector and a SCN1A nucleic acid, wherein the SCN1A nucleic acid is operatively linked to a CMV promoter. Preferably, the SCN1A nucleic acid comprises: (a) a nucleotide sequence comprising the nucleotide sequence of SEQ ID NO:1, further comprising one or more mutations, wherein the one or more mutations disrupt regions having a high spontaneous mutation rate; or (b) a nucleotide sequence substantially identical to SEQ ID NO:1, further comprising one or more mutations, wherein the one or more mutations disrupt regions having a high spontaneous mutation rate. More preferably, a SCN1A nucleic acid comprises: (a) a nucleic acid molecule comprising a nucleotide sequence of SEQ ID NO:3; or (b) a nucleic acid molecule that is substantially identical to SEQ ID NO:3, and wherein the nucleic acid molecule comprises a T to C transition at each of nucleotide positions 1206 and 1209 of SEQ ID NO:3.

Constructs are transfected into a host cell using a method compatible with the vector employed. Standard transfection methods include electroporation, DEAE-Dextran transfection, calcium phosphate precipitation, liposome-mediated transfection, transposon-mediated transformation, infection using a retrovirus, particle-mediated gene transfer, hypervelocity gene transfer, and combinations thereof.

The term "host cell", as used herein, refers to a cell into which a heterologous nucleic acid molecule has been introduced. Any suitable host cell can be used, including but not limited to eukaryotic hosts such as mammalian cells (e.g., tsA201 cells, HEK-293 cell, HeLa cells, CV-1 cells, COS cells), amphibian cells (e.g., *Xenopus oocytes*), insect cells (e.g., Sf9 cells), as well as prokaryotic hosts such as *E. coli* and *Bacillus subtilis*. A preferred host cell comprises a cell substantially lacking a SCN1A polypeptide. Preferred host cells also include but are not limited to mammalian cells, or more preferably human cells.

A host cell strain can be chosen which modulates the expression of the recombinant sequence, or modifies and processes the gene product in the specific fashion desired. For example, different host cells have characteristic and specific mechanisms for the translational and post-transactional processing and modification (e.g., glycosylation, phosphorylation of proteins). Appropriate cell lines or host systems can be chosen to ensure the desired modification and processing of the foreign protein expressed. For example, expression in a bacterial system can be used to produce a non-glycosylated core protein product, and expression in yeast will produce a glycosylated product.

In a preferred embodiment of the invention, SCN1A is expressed following transient transfection of tsA201 human embryonic kidney cells as described in the Examples.

The present invention further encompasses recombinant expression of the disclosed human SCN1A polypeptide in a stable cell line. Methods for generating a stable cell line are described in the Examples. Thus, transformed cells, tissues, or non-human organisms are understood to encompass not only the end product of a transformation process, but also transgenic progeny or propagated forms thereof.

Optionally, a system for recombinant expression of a SCN1A polypeptide, as disclosed herein, can further comprise one or more sodium channel β-subunit polypeptides. Interaction between a SCN1A polypeptide and a sodium channel β-subunit modulates electrophysiological properties of the channel, for example, by accelerating channel inactivation and shifting the voltage dependence of steady-state inactivation. See Morgan et al. (2000) *Proc Natl Acad Sci U S A* 97:2308–2313; Smith & Goldin (1998) *J Neurosci* 18:811–820; Smith et al. (1998) *J Neurosci* 18:6093–6102; Isom et al. (1992) *Science* 256:839–842.

Thus, nucleic acid molecules that can be used in accordance with the methods of the present invention include sodium channel β-subunit nucleic acids. In particular, nucleotide sequences encoding a SCN1B protein (SEQ ID NO:4) protein, nucleotide sequences encoding a SCN2B protein (SEQ ID NO:6), nucleotide sequences encoding a SCN3B protein (SEQ ID NO:8), and sequences substantially similar to SEQ ID NOs:4, 6, and 8 as defined herein above, can be used to prepare a system for heterologous expression of a functional human SCN1A.

In one embodiment of the invention, a system for heterologous expressing of a SCN1A polypeptide comprises a host cell expressing one or more native sodium channel β-subunits. In another embodiment of the invention, a system for heterologous expression of a SCN1A polypeptide comprises a host cell co-transfected with a construct whereby one or more sodium channel β-subunits are recombinantly expressed.

The present invention further encompasses cryopreservation of cells expression a recombinant SCN1A polypeptide as disclosed herein. Thus, transiently transfected cells and cells of a stable cell line expressing SCN1A can be frozen and stored for later use.

Cryopreservation media generally consists of a base medium, cryopreservative, and a protein source. The cryopreservative and protein protect the cells from the stress of the freeze-thaw process. For s rum-containing medium, a typical cryopreservation medium is prepared as complete medium containing 10% glycerol; complete medium containing 10% DMSO (dimethylsulfoxide), or 50% cell-conditioned medium with 50% fresh medium with 10% glycerol or 10% DMSO. For serum-free medium, typical cryopreservation formulations include 50% cell-conditioned serum free medium with 50% fresh serum-free medium containing 7.5% DMSO; or fresh serum-free medium containing 7.5% DMSO and 10% cell culture grade DMSO. Preferably, a cell suspension comprising about $10^6$ to about $10^7$ cells per ml is mixed with cryopreservation medium.

Cells are combined with cryopreservation medium in a vial or other container suitable for frozen storage, for example NUNC® CRYOTUBES™ (available from Applied Scientific of South San Francisco, Calif., United States of America). Cells can also be aliquotted to wells of a multi-well plate, for example a 96-well plate designed for high-throughput assays, and frozen in plated format.

Cells are preferably cooled from room temperature to a storage temperature at a rate of about –1° C. per minute. The cooling rate can be controlled, for example, by placing vials containing cells in an insulated water-filled reservoir having about 1 liter liquid capacity, and placing such cube in a –70° C. mechanical freezer. Alternatively, the rate of cell cooling can be controlled at about –1° C. per minute by submersing vials in a volume of liquid refrigerant such as an aliphatic alcohol, the volume of liquid refrigerant being more than fifteen times the total volume of cell culture to be frozen, and placing the submersed culture vials in a conventional freezer at a temperature below about –70° C. Commercial devices for freezing cells are also available, for example, the Planer Mini-Freezer R202/200R (Planer Products Ltd. of Great Britain) and the BF-5 Biological Freezer (Union Carbide Corporation of Danbury, Conn., United States of America). Preferably, frozen cells are stored at or below about –70° C. to about –80° C., and more preferably at or below about –130° C.

To obtain the best possible survival of the cells, thawing of the cells must be performed as quickly as possible. Once a vial or other reservoir containing frozen cells is removed from storage, it should be placed directly into a 37° C. water bath and gently shaken until it is completely thawed. If cells are particularly sensitive to cryopreservatives, the cells are centrifuged to remove cryopreservative prior to further growth.

Additional methods for preparation and handling of frozen cells can be found in Freshney (1987) *Culture of Animal Cells: A Manual of Basic Technique*, 2nd ed. A. R. Liss, New York and in U.S. Pat. Nos. 6,176,089; 6,140,123; 5,629,145; and 4,455,842; among other places.

Isolated polypeptides and recombinantly produced polypeptides can be purified and characterized using a variety of standard techniques that are known to the skilled artisan. See e.g., Schröder & Lübke (1965) *The Peptides*. Academic Press, New York; Schneider & Eberle (1993) *Peptides, 1992: Proceedings of the Twenty-Second European Peptide Symposium*, Sep. 13–19, 1992, Interlaken, Switzerland. Escom, Leiden; Bodanszky (1993) *Principles of Peptide Synthesis*, 2nd rev. ed. Springer-Verlag, Berlin; New York; Ausubel (ed.) (1995) *Short Protocols in Molecular Biology*, 3rd ed. Wiley, N.Y.

VI. SCN1A Antibodies

In another aspect of the invention, a method is provided for producing an antibody that specifically binds a human SCN1A polypeptide. According to the method, a full-length recombinant SCN1A polypeptide is formulated so that it can be used as an effective immunogen, and used to immunize an animal so as to generate an immune response in the animal. The immune response is characterized by the production of antibodies that can be collected from the blood serum of the animal. The present invention also provides antibodies produced by the disclosed methods.

The term "antibody" indicates an immunoglobulin protein, or functional portion thereof, including a polyclonal antibody, a monoclonal antibody, a chimeric antibody, a hybrid antibody, a single chain antibody, a mutagenized antibody, a humanized antibody, and antibody fragments that comprise an antigen binding site (e.g., Fab and Fv antibody fragments). In a preferred embodiment, an antibody of the invention is a monoclonal antibody. Thus, the present invention also encompasses antibodies and cell lines that produce monoclonal antibodies as described herein.

The term "specifically binds", when used to describe binding of an antibody to a human SCN1A polypeptide, refers to binding only to a SCN1A polypeptide in a heterogeneous mixture of other polypeptides.

The phases "substantially lack binding" or "substantially no binding", as used herein to describe binding of an antibody to a control polypeptide or sample, refers to a level of binding that encompasses non-specific or background binding, but does not include specific binding.

Techniques for preparing and characterizing antibodies are known in the art. See e.g., Harlow & Lane (1988) *Antibodies: A Laboratory Manual*, Cold Spring Harbor Laboratory Press, Cold Spring Harbor, N.Y. and U.S. Pat. Nos. 4,196,265; 4,946,778; 5,091,513; 5,132,405; 5,260,203; 5,677,427; 5,892,019; 5,985,279; 6,054,561.

SCN1A antibodies prepared as disclosed herein can be used in methods known in the art relating to the localization and activity of SCN1A polypeptides, e.g., for cloning of nucleic acids encoding a SCN1A polypeptide, immunopurification of a SCN1A polypeptide, imaging a SCN1A polypeptide in a biological sample, and measuring levels of a SCN1A polypeptide in appropriate biological samples. To perform such methods, an antibody of the present invention can further comprise a detectable label, including but not limited to a radioactive label, a fluorescent label, an epitope label, and a label that can be detected in vivo. Methods for selection of a label suitable for a particular detection technique, and methods for conjugating to or otherwise associating a detectable label with an antibody are known to one of skill in the art.

VII. Methods for Detecting a SCN1A Polypeptide

Also provided is a method for detecting a human SCN1A polypeptide. The disclosed methods for detecting SCN1A can be used to determine altered levels of gene expression that are associated with disorders and disease states, including but not limited to conditions of pain or seizure.

In one embodiment, the method involves performing an immunochemical reaction with an antibody that specifically recognizes a human SCN1A polypeptide, wherein the antibody was prepared according to a method of the present invention for producing such an antibody. Thus, the method comprises: (a) obtaining a biological sample comprising peptidic material; (b) contacting the biological sample with an antibody that specifically binds a SCN1A polypeptide and that was produced according to the disclosed methods, wherein the antibody comprises a detectable label; and (c) detecting the detectable label, whereby a sodium channel polypeptide in a sample is detected.

Techniques for detecting such antibody-antigen conjugates or complexes are known in the art and include but are not limited to centrifugation, affinity chromatography and other immunochemical methods. See e.g., Manson (1992) *Immunochemical Protocols.* Humana Press, Totowa, N.J.; Ishikawa (1999) *Ultrasensitive and Rapid Enzyme Immunoassay.* Elsevier, Amsterdam; New York; Law (1996) *Immunoassay: A Practical Guide.* Taylor & Francis, London/Bristol, Pennsylvania; Chan (1996) *Immunoassay Automation: An Updated Guide to Systems.* Academic Press, San Diego; Liddell & Weeks (1995) *Antibody Technology.* Bios Scientific Publishers, Oxford, United Kingdom; Masseyeff et al. (1993) *Methods of Immunological Analysis.* VCH Verlagsgesellschaft/VCH Publishers, Weinheim, Federal Republic of Germany/New York; Walker & Rapley (1993) *Molecular and Antibody Probes in Diagnosis.* Wiley, Chichester, N.Y.; Wyckoff et al. (1985) *Diffraction Methods for Biological Macromolecules.* Academic Press, Orlando, Fla.; and references cited therein.

In another embodiment, a modulator that shows specific binding to a human SCN1A polypeptide is used to detect a sodium channel. Analogous to detection of a SCN1A polypeptide using an antibody, the method comprises: (a) obtaining a biological sample comprising peptidic material; (b) contacting the biological sample with a modulator of a sodium channel type 1 α-subunit polypeptide, wherein the modulator comprises a detectable label; and (c) detecting the detectable label, whereby a human sodium channel type 1 α-subunit polypeptide in a sample is detected. Alternatively, a detection method can comprise detection of specific binding of a modulator to a peptidic sample. Representative techniques for assaying specific binding are described herein below under the heading "Assays of SCN1A Binding and Activity".

VIII. Assays of SCN1A Binding and Activity

The present invention further discloses assays to determine binding to a SCN1A polypeptide or modulation of SCN1A activity. Each of the assays employs a system for heterologous expression of a SCN1A polypeptide, as disclosed herein above, or an isolated SCN1A polypeptide produced in such a system. The present invention also provides sodium channel modulators identified using the disclosed methods.

The method for identifying a SCN1A modulator comprises: (a) providing a heterologous expression system whereby a human SCN1A polypeptide is expressed in a host cell; (b) providing a test substance to the system of (a); (c) assaying a level or quality of SCN1A function in the presence of the test substance; (d) comparing the level or the quality of SCN1A function in the presence of the test substance with a control level or quality of SCN1A function; and (e) identifying a test substance as a modulator of a SCN1A function by determining a level or quality of SCN1A function in the presence of the test substance as significantly changed relative to a control level or quality of SCN1A function.

The term "modulate" means an increase, decrease, or other alteration of any or all chemical and biological activities or properties of a SCN1A polypeptide, preferably a human SCN1A polypeptide. Thus, the method for identifying modulators involves assaying a level or quality of SCN1A function.

In one embodiment of the invention, assaying SCN1A activity comprises determining a level of SCN1A expression or presence using the detection methods described herein above.

In a preferred embodiment of the invention, assaying SCN1A activity comprises assaying electrophysiological or pharmacological properties of a recombinantly expressed SCN1A polypeptide. A representative level of SCN1A activity can thus comprise an amount of ion conductance, a peak level of ion conductance, or an amount of binding, measurable as described herein below. A representative quality of SCN1A activity can comprise, for example, kinetic features of SCN1A channel opening and/or closing, single-channel conductance level, and pharmacological profile of a SCN1A polypeptide. Representative methods for determining levels and qualities of SCN1A function are described in the Examples, e.g. Example 4.

A control level or quality of SCN1A activity refers to a level or quality of wild type SCN1A activity. A system for heterologous expression of a SCN1A polypeptide comprising SEQ ID NO:2 establishes a control level or quality of SCN1A activity as a level or quality of activity in the absence of a test substance. When evaluating the function of a mutant SCN1A polypeptide, a control level or quality of SCN1A activity comprises a level or quality of activity of a non-mutated SCN1A polypeptide set forth as SEQ ID NO:2.

The term "significantly changed", as used herein to refer to an altered level or activity of a SCN1A polypeptide, refers to a quantified change in a measurable quality that is larger than the margin of error inherent in the measurement technique, preferably an increase or decrease by about 2-fold or greater relative to a control measurement, more preferably an increase or decrease by about 5-fold or greater, and most preferably an increase or decrease by about 10-fold or greater.

Modulators identified by the disclosed methods can comprise agonists and antagonists. As used herein, the term "agonist" means a substance that synergizes or potentiates the biological activity of a SCN1A polypeptide. As used herein, the term "antagonist" refers to a substance that blocks or mitigates the biological activity of a SCN1A polypeptide. A modulator can also comprise a ligand or a substance that specifically binds to a SCN1A polypeptide. Activity and binding assays for the determination of a SCN1A modulator can be performed in vitro or in vivo.

In one embodiment of the invention, such assays are useful for the identification of SCN1A modulators that can be developed for the treatment and/or diagnosis of SCN1A-related disorders, as described further herein below under the heading "Therapeutic Methods."

In another embodiment of the invention, assays using a recombinant SCN1A polypeptide can be performed for the purpose of prescreening bioactive agents, wherein an interaction between the agent and SCN1A is undesirable. Thus, drugs intended for administration to a subject for the treatment of a non-SCN1A-related disorder, agricultural agents, food preservatives, etc. can be tested for SCN1A modulating activity that can result in undesirable side effects. For example, DDT (a mixture comprising p,p'-DDT [dichlorodiphenyl trichloroethane]; 2,2-bis (p-chlorophenyl)-1,1,1-trichloroethane)), DDT analogs, and other pyrethroid insecticides are potent enhancers of insect sodium channel conductance. These substances can also cause substantial human toxicity by sodium channel regulation as in insects. As another example, antiarrhythmic agents and local anesthetics can have adverse effects linked to sodium channel blockade. See e.g., Caron & Libersa (1997) *Drug Saf* 17:8–36. The disclosed assays and methods enable prescreening of bioactive agents under development to identify deleterious effects of sodium channel regulation.

In still another embodiment of the invention, an assay disclosed herein can be used to characterize a mutant sodium channel, such as that responsible for generalized epilepsy with febrile seizures plus (GEFS+). GEFS+ is an autosomal dominant disorder characterized by febrile seizures in children and afebrile seizures in adults. For example, a system for heterologous expression of a sodium channel can comprise co-expression of a SCN1A polypeptide and a SCN1B polypeptide, wherein the SCN1B polypeptide harbors a cysteine to tryptophan conversion at amino acid residue 121 (C121W) that is genetically linked to GEFS+ (Wallace et al., 1998). Similarly, a mutant sodium channel can be expressed by employing a polypepide that is substantially similar to SCN1A, wherein the nucleotide sequence encoding a polypeptide substantially similar to SCN1A comprises: (a) mutations that enable genetic stability and recombinant expression as disclosed herein; and (b) additional mutations relevant to SCN1A-related disorders. For example, for the study of a mutant sodium channel linked to GEFS+, a recombinant SCN1A polypeptide can comprise a T875M mutation or a R1648H mutation, each associated with GEFS+ (Escayg et al., 2000; Escayg et al., 2001). Recombinant expression of mutated sodium channels will permit further analysis of the disease-related channels.

Preliminary efforts to examine physiological properties of sodium channels bearing GEFS+ mutations have employed sodium channel α-subunits other than human SCN1A. Co-expression of human SCN1B bearing a C121W mutation and a rat SCN1A polypeptide demonstrated a slight slowing of sodium channel fast inactivation (Wallace et al., 1998). Another strategy employed recombinant expression of human SCN4A, the skeletal muscle voltage-gated sodium channel, wherein the nucleotide sequence encoding SCN4A was mutated at residues homologous to the mutated amino acids observed in GEFS+ patients. These studies demonstrated an acceleration of recovery from fast inactivation for SCN4A comprising a mutation homologous to T685M in SCN1A (Alekov et al., 2000). SCN4A polypeptides comprising a mutation homologous to T875M in SCN1A showed surprisingly different effects on channel physiology, including enhanced inactivation and defects in channel activation (Alekov et al., 2001). Similarly, Spampanato et al. studied the functional effects of two epilepsy-associated mutations using a recombinant rat SCN1A heterologously expressed in *Xenopus oocytes* and reported subtle changes in inactivation properties of the sodium channel (Spampanato et al., 2001). Although these observations have been extrapolated to assumptions of human SCN1A function, a dear demonstration of human SCN1A function has not been accomplished. Thus, the present invention provides, for the first time, a recombinant human SCN1A polypeptide that can be used for such analysis, as disclosed in the Examples, e.g. Examples 5, 6, and 7. The assays disclosed herein can thus facilitate the development of genotype specific treatments for epilepsy.

VIII.A. Test Substances

A potential modulator assayed using the methods of the present invention comprises a candidate substance. As used herein, the terms "candidate substance" and "test substance" are used interchangeably, and each refers to a substance that is suspected to interact with a SCN1A polypeptide, including any synthetic, recombinant, or natural product or composition. A test substance suspected to interact with a polypeptide can be subsequently evaluated for such an interaction. A test substance can comprise a peptide, an oligomer, a nucleic acid (e.g., an aptamer), a small molecule (e.g., a chemical compound), an antibody or fragment thereof, a nucleic acid-protein fusion, any other affinity agent, and combinations thereof. A candidate substance to be tested can be a purified molecule, a homogenous sample, or a mixture of molecules or compounds.

The term "small molecule" as used herein refers to a compound, for example an organic compound, with a molecular weight of less than about 1,000 daltons, more preferably less than about 750 daltons, still more preferably less than about 600 daltons, and still more preferably less than about 500 daltons. A small molecule also preferably has a computed log octanol-water partition coefficient in the range of about −4 to about +14, more preferably in the range of about −2 to about +7.5.

A test substance can additionally comprise a carbohydrate, a vitamin or derivative thereof, a hormone, a neurotransmitter, a virus or receptor binding domain thereof, an opsin or rhodopsin, an odorant, a pheromone, a toxin, a growth factor, a platelet activation factor, a neuroactive peptide, or a neurohormone.

In accordance with the present invention there is also provided a rapid and high throughput screening method that relies on the methods described herein below. This screening method comprises separately contacting a SCN1A polypeptide with a plurality of test substances. In such a screening method the plurality of target substances preferably comprises more than about $10^4$ samples, or more preferably comprises more than about $10^5$ samples, and still more preferably more than about $10^6$ samples.

Test substances can be obtained or prepared as a library. As used herein, the term "library" means a collection of molecules. A library can contain a few or a large number of different molecules, varying from about ten molecules to several billion molecules or more. A molecule can comprise a naturally occurring molecule, a recombinant molecule, or a synthetic molecule. A plurality of test substances in a library can be assayed simultaneously. Optionally, test substances derived from different libraries can be pooled for simultaneous evaluation.

Representative libraries include but are not limited to a peptide library (U.S. Pat. Nos. 6,156,511, 6,107,059, 5,922,545, and 5,223,409), an oligomer library (U.S. Pat. Nos. 5,650,489 and 5,858,670), an aptamer library (U.S. Pat. No. 6,180,348 and 5,756,291), a small molecule library (U.S. Pat. Nos. 6,168,912 and 5,738,996), a library of antibodies or antibody fragments (U.S. Pat. Nos. 6,174,708, 6,057,098, 5,922,254, 5,840,479, 5,780,225, 5,702,892, and 5,667,988), a library of nucleic acid-protein fusions (U.S. Pat. No. 6,214,553), and a library of any other affinity agent that can potentially bind to a SCN1A polypeptide (e.g., U.S. Pat. Nos. 5,948,635, 5,747,334, and 5,498,538).

A library can comprise a random collection of molecules. Alternatively, a library can comprise a collection of molecules having a bias for a particular sequence, structure, or conformation. See e.g., U.S. Pat. Nos. 5,264,563 and 5,824,483. Methods for preparing libraries containing diverse populations of various types of molecules are known in the art, for example as described in U.S. patents cited herein above. Numerous libraries are also commercially available.

VIII.B. Functional Assays

In a preferred embodiment of the invention, a SCN1A modulator is identified by assessing a biological activity of a recombinantly expressed SCN1A polypeptide. Representative methods for determining a sodium channel activity include but are not limited to a whole-cell patch clamp assay, an ion influx assay, and a cell morphology or cell viability assay, each described briefly herein below.

In accordance with the method, cells expressing SCN1A can be provided in the form of a kit useful for performing an assay of SCN1A function. Thus, cells can be frozen as described herein above and transported while frozen to others for performance of an assay. For example, in one embodiment of the invention, a test kit is provided for detecting a SCN1A modulator, the kit comprising: (a) frozen cells transfected with DNA encoding full-length SCN1A; and (b) a medium for growing the cells. Optionally, cells used in the assay also express one or more sodium channel β subunits, preferably SCN1B (SEQ ID NO:5), SCN2B (SEQ ID NO:7), or SCN3B (SEQ ID NO:9).

Preferably, a cell used in such an assay comprises a cell that is substantially devoid of native SCN1A and polypeptides substantially similar to SCN1A. A preferred cell comprises a mammalian cell, more preferably a human cell, even more preferably a tsA201 human embryonic kidney cell. In one embodiment, a cell used in the assay comprises a stable cell line that recombinantly expresses SCN1A, as described in the Examples, e.g. Example 4. Alternatively, a cell used in the assay can transiently express a functional brain-specific voltage-gated sodium channel α subunit type I polypeptide as described in the Examples, e.g. Example 3.

The term "substantially devoid of", as used herein to describe a host cell or a control cell, refers to a quality of having a level of native SCN1A, a level of a polypeptide substantially similar to SCN1A, or a level of activity thereof, comprising a background level. The term "background level" encompasses non-specific measurements of expression or activity that are typically detected in a cell free of SCN1A and free of polypeptides substantially similar to SCN1A.

Also preferably, all assays employing cells expressing recombinant SCN1A additionally employ control cells that are substantially devoid of native SCN1A and polypeptides substantially similar to SCN1A. When using transiently transfected cells, a control cell can comprise, for example, an untransfected host cell. When using a stable cell line expressing SCN1A, a control cell can comprise, for example, a parent cell line used to derive the SCN1A-expressing cell line.

Assays of SCN1A activity that employ transiently transfected cells preferably include a marker that distinguishes transfected cells from non-transfected cells. The term "marker" refers to any detectable molecule that can be used to distinguish a cell that recombinantly expresses SCN1A from a cell that does not recombinantly express SCN1A. Preferably, a marker is encoded by or otherwise associated with a construct for SCN1A expression, such that cells are simultaneously transfected with a nucleic acid molecule encoding SCN1A and the marker. Representative detectable molecules that are useful as markers include but are not limited to a heterologous nucleic acid, a polypeptide encoded by a transfected construct (e.g., an enzyme or a fluorescent polypeptide), a binding protein, and an antigen.

A marker comprising a heterologous nucleic acid includes nucleic acids encoding a SCN1A polypeptide. Such nucleic acids can be detected, for example, using an RH-PCR assay. See Chiang (1998) *J Chromatogr A* 806:209–218, and references cited therein.

Examples of enzymes useful as markers are phosphatases (such as acid or alkaline phosphatase), β-galactosidase, urease, glucose oxidase, carbonic anhydrase, acetylcholinesterase, glucoamylase, maleate dehydrogenase, glucose-6-phosphate dehydrogenase, β-glucosidase, proteases, pyruvate decarboxylase, esterases, luciferase, alcohol dehydrogenase, or peroxidases (such as horseradish peroxidase). A marker comprising an enzyme can be detected based on activity of the enzyme. Thus, a substrate is b added to catalyze a reaction the end product of which is detectable, for example using spectrophotometer, a luminometer, or a fluorimeter. Substrates for reaction by the above-mentioned enzymes, and that produce a detectable reaction product, are known to one of skill in the art.

A preferred marker comprises an encoded polypeptide that can be detected in the absence of an added substrate. Representative polypeptides that can be detected directly include GFP and EGFP. Common research equipment has been developed to perform high-throughput detection of fluorescence, for example GFP or EGFP fluorescence, including instruments from GSI Lumonics (Watertown, Mass., United States of America), Amersham Pharmacia Biotech/Molecular Dynamics (Sunnyvale, Calif., United States of America), Applied Precision Inc. (Issauah, Wash., United States of America), and Genomic Solutions Inc. (Ann Arbor, Mich., United States of America). Most of the commercial systems use some form of scanning technology with photomultiplier tube detection.

A marker can also comprise an epitope, for example a binding protein or an antigen, which can be detected by providing a detectably labeled ligand or antibody, respectively. A detectable label comprises an enzyme or directly detectable label as described herein above. For example, avidin and streptavidin are representative binding proteins that each specifically bind biotin. Antigens useful as markers include any antigen associated with the construct encoding SCN1A, including recombinantly produced SCN1A and an antigen of the vector comprising SCN1A nucleic acids (e.g., in the case of a viral vector, a viral coat protein). Methods for immunodetection are described herein above.

Whole-Cell Patch Clamp. In a preferred embodiment of the invention, SCN1A activity is determined using a whole-cell patch clamp technique, which enables measurement of macroscopic sodium currents. Example 4 describes whole-cell voltage clamp measurements of SCN1A recombinantly expressed in human embryonic kidney cells. Any heterologous host cell can be used for patch clamp analysis, including but not limited to PC12 cells (D'Arcangelo et al., 1993), *Xenopus oocytes* (Stuhmer et al., 1987; Taglialatela et al., 1992; Ji et al., 1999), Chinese hamster ovary (CHO) cells (Dupere et al., 1999), HEK-293 human kidney cells (Sabirov et al., 1999), and Sf9 insect cells (Yamashita et al., 1999). For selective study of Na+ currents mediated by recombinant expression of a SCN1A polypeptide, a host cell is preferably free of endogenous voltage-gated sodium channels.

A voltage clamp assay of the present invention can also comprise determining sodium channel activity in the presence of a test substance and a known sodium channel modulator. For example, the method can comprise: (a) providing an expression system, whereby a functional SCN1A polypeptide is expressed; (b) adding a persistent sodium channel activator to the expression system, whereby sodium conductance is elicited; (c) adding a test substance to the expression system; and (d) observing a suppression of the conductance in the presence of the persistent activator and the test substance, whereby an inhibitor of SCN1A is determined. See U.S. Pat. No. 6,174,690. Optionally, the persistent activator and test substance can be provided to the functional expression simultaneously. Similarly, an assay for determining a SCN1A activator can comprise steps (a)–(d) above with the exception that an enhancement of conductance is observed in the presence of the persistent activator and the test substance.

Ion Flux Assay. A candidate substance can be tested for its ability to modulate a brain-specific voltage-gated sodium channel by determining the movement of ion tracers through the channel. Representative labeled sodium ions that can be used to assay channel conductance include but are not limited to $^{22}$Na (Catterall et al., 1981) and the less toxic $^{14}$C guanidinium ion (Reith, 1990). Briefly, aliquots of a cell suspension comprising cells expressing a recombinant SCN1A polypeptide are incubated for 10 minutes at 37° C. in the presence of channel openers (typically, 100 μM veratridine) and test substances in a total volume of 100 μM (0.20–0.25 mg protein). Ion flux is initiated by the addition of hepes/tris solution also containing 4 mM guanidine HCl (final) and 1000 dpm/nmol $^{14}$C guanidine. The reaction is continued for 30 seconds and is stopped by the addition of ice-cold incubation buffer, followed by rapid filtration under vacuum over a glass microfibre filter (grade GF/C, 1.2 μm available from Whatman, Inc. of Clifton, N.J.). The filters are washed rapidly with ice-cold incubation buffer and radioactivity is determined by scintillation counting. Non-specific uptake is determined in parallel by including 10 μM tetrodotoxin during the preincubation and uptake periods.

An ion flux assay can further comprise contacting a cell expressing SCN1A with a test substance and a known SCN1A modulator, as described herein above as a variant patch clamp assay. For example, substantial ion flux is observed in the presence of a persistent sodium channel activator, and a reduction of flux following subsequent application of a test substance indicates an antagonist activity of the test substance. Similarly, observation of enhanced ion flux of an already activated SCN1A following application of a test substance indicates an agonist activity of the test substance.

Cell Morphology/Viability Assay. Sodium channel modulators can also be identified by assaying cellular effects of sodium blockade (Kogure et al., 1988). The assay uses a fixed concentration of the sodium channel-activator veratridine in the presence of ouabain, an inhibitor of Na+/K+ ATPase. The combined effect of these agents is an enhanced sodium influx, leading to altered cell morphology, subsequent decrease in cell viability and ultimate cell lysis. Tetrodotoxin, saxitoxin, and related toxins that block sodium channels antagonize this effect, essentially "rescuing" the cells in a dose-dependent manner. This phenomenon provides the basis of a sensitive in vitro bioassay for Na$^+$ channel toxins. Scoring of this assay can be accomplished using a microplate reader for automated determinations of absorbances of toxin-treated cells which were stained with crystal violet, as described by Jellett et al. (1992) *Toxicon* 30:1143–1156.

To perform the assay, wells containing cells expressing a recombinant SCN1A polypeptide are inoculated with test substance and then with ouabain/veratridine, incubated, and subsequently rinsed. Aft rerinsing, the wells are fixed and stained with crystal violet. The processed plates are then dried, and the stained cells are digested in acetic acid. Finally, the plates are read for absorbance of crystal violet in each well, with the absorbance being directly related to the amount of test substance originally present. Modulators identified using this assay are sodium channel blockers.

This assay exploits the difference in adherence to the culture well of cells treated only with ouabain/veratridine and cells treated with a sodium channel blocker. The former cells exhibit diminished adherence to the culture well, associated with swelling and lysis, and are readily removed by rinsing, whereas the latter cells which are protected from the effects of ouabain/veratridine, retain substrate adherence. Thus, cells affected only by ouabain/veratridine lose adherence and are removed during rinsing, while cells inoculated with a sodium channel blocker remain in the well.

Cell viability can also be assessed by providing a substrate for mitochondrial dehydrogenase, wherein metabolism of the substrate by living cells can be detected calorimetrically. Representative indicators include 3-(4,5-dimethylthiazole-2-yl)-2,5-diphenyl tetrazolium bromide (MTT), 2,3-bis(2-methoxy-4-nitro-5-sulfophenyl)-2H-tetrazolium-5-carboxanilide inner salt (XTT) (available from Sigma of St. Louis, Mo.), and methylene blue. MTT and XTT are metabolized only in living cells to produce blue and orange formazan products, respectively. Methylene blue is decolorized by dehydrogenase activity of living cells. See U.S. Pat. No. 5,858,687.

Cell Growth Assay. A related assay measures SCN1A activity by observing cell growth. High levels of sodium channel expression are correlated with cell growth. Conversely, sodium channel inhibitors effectively retard cell growth (Abdul & Hoosein, 2001). Thus, cell growth can be used as an indicator of SCN1A activity. A cell growth assay includes the steps of: (a) incubating, under conditions permitting cell amplification, cells expressing a recombinant SCN1A polypeptide, the cells comprising a marker of cell amplification, with a test substance; and (b) after a period of time sufficient to permit cell amplification, determining the presence or absence of amplification of cells containing the marker relative to cells not containing the marker.

When transiently transfected cells are used, a mixture of transfected and nontransfected cells will typically be present in step (a). When a test substance is added to the mixture, its ability to act as a SCN1A modulator is determined in terms of its ability to confer a competitive advantage on the transfected cells in the mixture that are expressing SCN1A, relative to the non-transfected cells which do not express SCN1A. Thus, if the test substance is an SCN1A agonist, the transfected cells in the mixture will be preferentially amplified in response to the agonist, in comparison with nontransfected cells. The transfected cells are distinguishable from the nontransfected cells in the mixed population by the presence of a marker in the transfected cells. When the test substance is an antagonist, the action can be determined similarly, but in reverse, i.e., the cells containing the marker will be at a competitive disadvantage relative to the untransfected cells, the population of which will expand at a greater rate than the transfected cells. For identification of SCN1A antagonists, a growth assay is preferably conducted in the presence of an agonist, and the observed effect is a decrease in the amplification response brought about by the presence of the agonist alone. See also U.S. Pat. Nos. 5,912,132 and 5,707,798.

The method can also be performed using a stable cell line that expressed a recombinant SCN1A polypeptide. In this case, cell growth of SCN1A-expressing cells in the presence is compared to cell growth of control cells that are substantially devoid of a SCN1A polypeptide.

VIII.C. Conformational Assay

The present invention also provides a method for identifying a SCN1A modulator that relies on a conformational change of a SCN1A polypeptide when bound by or otherwise interacting with a SCN1A modulator.

Application of circular dichroism to solutions of macromolecules reveals the conformational states of these macromolecules. The technique can distinguish random coil, alpha helix, and beta chain conformational states. The secondary structure of a rat sodium channel α-subunit has been determined by circular dichroism as a conformationally flexible polypeptide that contains mostly β-sheet and random coil which fold into a conformation comprising about 65% α-helix (Elmer et al., 1985; Oiki et al., 1990). Provision of a sodium channel antagonist results in a sharp helical transition near body temperature. Addition of a sodium channel agonist alters the temperature-dependent helix transition such that it is observed only at more elevated temperatures. See U.S. Pat. Nos. 5,776,859 and 5,780,242.

To identify modulators of SCN1A, circular dichroism analysis can be performed using recombinantly expressed SCN1A. SCN1A polypeptide is purified, for example by ion exchange and size exclusion chromatography, and mixed with a test substance. The mixture is subjected to circular dichroism at a wave length of 222 nM wave length. The transition of molar ellipticity is compared with a control SCN1A polypeptide that has not been exposed to the test substance. Alpha helical content, as measured at 222 nm, is used to monitor the effect of temperature change on SCN1A conformation. The different conformational state of a sodium channel in the absence of a modulator when compared to a conformational state in the presence of an antagonist, an agonist, or a combination thereof, can thus be used to identify a SCN1A modulator.

VIII.D. Binding Assays

In another embodiment, a method for identification of a sodium channel modulator comprises determining specific binding of a test substance to a SCN1A polypeptide. The term "binding" refers to an affinity between two molecules. The term "binding" also encompasses a quality or state of mutual action such that an activity of one protein or compound on another protein is inhibitory (in the case of an antagonist) or enhancing (in the case of an agonist).

The phrase "specifically binds", when referring to the binding capacity of a candidate modulator, refers to a binding reaction which is determinative of the presence of the protein in a heterogeneous population of proteins and other biological materials. The binding of a modulator to a SCN1A polypeptide can be considered specific if the binding affinity is about $1 \times 10^4$ $M^{-1}$ to about $1 \times 10^6$ $M^{-1}$ or greater. The phrase "specifically binds" also refers to saturable binding. To demonstrate saturable binding of a test substance to a SCN1A polypeptide, Scatchard analysis can be carried out as described, for example, by Mak et al. (1989) *J Biol Chem* 264:21613–21618.

The phases "substantially lack binding" or "substantially no binding", as used herein to describe binding of a modulator to a control polypeptide or sample, refers to a level of binding that encompasses non-specific or background binding, but does not include specific binding.

Several techniques can be used to detect interactions between a SCN1A polypeptide and a test substance without employing a known competitive modulator. Representative methods include, but are not limited to, Fluorescence Correlation Spectroscopy, Surface-Enhanced Laser Desorption/Ionization Time-Of-flight Spectroscopy, and Biacore technology, each technique described herein below. These methods are amenable to automated, high-throughput screening.

Fluorescence Correlation Spectroscopy. Fluorescence Correlation Spectroscopy (FCS) measures the average diffusion rate of a fluorescent molecule within a small sample volume (Magde et al., 1972; Maiti et al., 1997). The sample size can be as low as $10^3$ fluorescent molecules and the sample volume as low as the cytoplasm of a single bacterium. The diffusion rate is a function of the mass of the molecule and decreases as the mass increases. FCS can therefore be applied to polypeptide-ligand interaction analysis by measuring the change in mass and therefore in diffusion rate of a molecule upon binding. In a typical experiment, the target to be analyzed (e.g., a SCN1A polypeptide) is expressed as a recombinant polypeptide with a sequence tag, such as a poly-histidine sequence, inserted at the N-terminus or C-terminus. The expression is mediated in a host cell, such as *E. coli,* yeast, *Xenopus oocytes,* or mammalian cells. The polypeptide is purified using chromatographic methods. For example, the poly-histidine tag can be used to bind the expressed polypeptide to a metal chelate column such as $Ni^{2+}$ chelated on iminodiacetic acid agarose. The polypeptide is then labeled with a fluorescent tag such as carboxytetramethylrhodamine or BODIPY™ reagent (available from Molecular Probes of Eugene, Oreg.). The polypeptide is then exposed in solution to the potential ligand, and its diffusion rate is determined by FCS using instrumentation available from Carl Zeiss, Inc. (Thornwood, N.Y.). Ligand binding is determined by changes in the diffusion rate of the polypeptide.

Surface-Enhanced Laser Desorption/Ionization. Surface-Enhanced Laser Desorption/Ionization (SELDI) was developed by Hutchens & Yip (1993) *Rapid Commun Mass Spectrom* 7:576–580. When coupled to a time-of-flight mass spectrometer (TOF), SELDI provides a technique to rapidly analyze molecules retained on a chip. It can be applied to ligand-protein interaction analysis by covalently binding the target protein, or portion thereof, on the chip and analyzing by mass spectrometry the small molecules that bind to this protein (Worrall et al., 1998). In a typical experiment, a target polypeptide (e.g., a SCN1A polypeptide) is recombinantly expressed and purified. The target polypeptide is bound to a SELDI chip either by utilizing a poly-histidine tag or by other interaction such as ion exchange or hydrophobic interaction. A chip thus prepared is then exposed to the potential ligand via, for example, a delivery system able to pipet the ligands in a sequential manner (autosampler). The chip is then washed in solutions of increasing stringency, for example a series of washes with buffer solutions containing an increasing ionic strength. After each wash, the bound material is analyzed by submitting the chip to SELDI-TOF. Ligands that specifically bind a target polypeptide are identified by the stringency of the wash needed to elute them.

Biacore. Biacore relies on changes in the refractive index at the surface layer upon binding of a ligand to a target polypeptide (e.g., a SCN1A polypeptide) immobilized on the layer. In this system, a collection of small ligands is injected sequentially in a 2-5 microliter cell, wherein the target polypeptide is immobilized within the cell. Binding is detected by surface plasmon resonance (SPR) by recording laser light refracting from the surface. In general, the refractive index change for a given change of mass concentration at the surface layer is practically the same for all proteins and peptides, allowing a single method to be applicable for any protein (Liedberg et al., 1983; Malmquist, 1993). In a typical experiment, a target protein is recombinantly expressed, purified, and bound to a Biacore chip. Binding can be facilitated by utilizing a poly-histidine tag or by other interaction such as ion exchange or hydrophobic interaction. A chip thus prepared is then exposed to one or more potential ligands via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics of on rate and off rate allows the discrimination between non-specific and specific interaction. See also Homola et al. (1999) *Sensors and Actuators* 54:3–15 and references therein.

VIII.E. Rational Design

The knowledge of the structure a native human brain-specific voltage-gated sodium channel a subunit polypeptide provides an approach for rational design of modulators and diagnostic agents. In brief, the structure of a human SCN1A polypeptide can be determined by X-ray crystallography and/or by computational algorithms that generate three-dimensional representations. See Saqi et al. (1999) *Bioinformatics* 15:521–522; Huang et al. (2000) *Pac Symp Biocomput*:230–241; and PCT International Publication No. WO 99/26966. Alternatively, a working model of a human SCN1A polypeptide structure can be derived by homology modeling (Maalouf et al., 1998). Computer models can further predict binding of a protein structure to various substrate molecules that can be synthesized and tested using the assays described herein above. Additional compound design techniques are described in U.S. Pat. Nos. 5,834,228 and 5,872,011.

In general, a SCN1A polypeptide is a membrane protein, and can be purified in soluble form using detergents or other suitable amphiphillic molecules. The resulting SCN1A polypeptide is in sufficient purity and concentration for crystallization. The purified SCN1A polypeptide preferably runs as a single band under reducing or non-reducing polyacrylamide gel electrophoresis (PAGE). The purified SCN1A polypeptide is can be crystallized under varying conditions of at least one of the following: pH, buffer type, buffer concentration, salt type, polymer type, polymer concentration, other precipitating ligands and concentration of purified and cleaved SCN1A. Methods for generation of a crystalline polypeptide are known in the art and can be reasonably adapted for determination of a SCN1A polypeptide as disclosed herein. See e.g., Deisenhofer et al. (1984) *J Mol Biol* 180:385–398; Weiss et al. (1990) *FEBS Lett* 267:268–272; or the methods provided in a commercial kit, such as the CRYSTAL SCREEN™ kit (available from Hampton Research of Riverside, Calif.).

A crystallized SCN1A polypeptide is tested for functional activity and differently sized and shaped crystals are further tested for suitability in X-ray diffraction. Generally, larger crystals provide better crystallography than smaller crystals, and thicker crystals provide better crystallography than thinner crystals. Preferably, SCN1A crystals range in size from 0.1–1.5 mm. These crystals diffract X-rays to at least 10 Å resolution, such as 1.5–10.0 Å or any range of value therein, such as 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 or 3, with 3.5 Å or less being preferred for the highest resolution.

IX. Therapeutic Methods

The present invention further provides methods for modulation of sodium channel activity in a subject. Modulation can comprise a change in activity of any sodium channel α-subunit. More preferably, the sodium channel activity that is altered in a subject comprises an activity of a human SCN1A polypeptide, as defined herein above.

In one embodiment of the invention, a method for modulating sodium channel function in a subject comprises: (a) preparing a composition, comprising a modulator identified according to the disclosed methods, and a pharmaceutically acceptable carrier, (b) administering an effective dose of the pharmaceutical composition to a subject, whereby sodium channel activity is altered in the subject.

In another embodiment of the invention, a method for modulating sodium channel activity in a subject comprises: (a) preparing a gene therapy vector having a nucleotide sequence encoding a human sodium channel type 1 α-subunit polypeptide, or a nucleotide sequence encoding a nucleic acid molecule, peptide, or protein that modulates a human sodium channel type 1 α-subunit polypeptide; and (b) administering the gene therapy vector to a subject, whereby the function of a sodium channel in the subject is modulated.

SCN1A modulators identified using the compositions and methods disclosed herein are useful as drugs for treatment of sodium channel-related disorders. The term "drug" as used herein refers to any substance having biological or detectable activity, including a therapeutic agent, a diagnostic agent, or a combination thereof. Preferably, SCN1A modulators display a biological activity including but not limited to anticonvulsant activity, antiepileptic activity, local anesthesia or other pain relief, neuroprotection, and combinations thereof, as described herein below.

In one embodiment of the invention, a SCN1A antagonist can be used to treat pain due to trauma or pathology involving the nervous system. Following injury to the nervous system, spinal sensory neurons that produce nociceptive signals become hyperexcitable, generating spontaneous action potentials or abnormal high-frequency activity that contributes to chronic pain. Voltage-gated sodium channel α-subunits are principal mediators of pain pathophysiology (Eglen et al., 1999; Gold, 1999; McCleskey & Gold, 1999; Porreca et al., 1999; Waxman et al., 1999b; Waxman et al., 1999a; Sindrup & Jensen, 2000). Thus, a substance that antagonizes sodium channel function can comprise a drug for pain relief. A sodium channel antagonist can also be used as a local anesthetic. See e.g., Duch et al. (1998) *Toxicol Lett* 100–101:255–263.

Many antiepileptic drugs effective in control of partial and generalized toni-clonic seizures are use- and voltage-dependent blockers of sodium channels. See e.g., Coulter (1997) *J Child Neurol* 12 Suppl 1:S2–9. Thus antagonists of SCN1A can be useful for the treatment of GEFS+, as described herein above. Severe myoclonic epilepsy of infancy (SMEI) is another disorder characterized by generalized tonic, clonic, and tonic-clonic seizures that are initially induced by fever and subsequently occur in the absence of fever. Patients with SMEI show developmental stagnation, including ataxia and delayed speech development. Mutations in SCN1A are also linked to severe SMEI (Claes et al., 2001), and thus antagonists of SCN1A can be used to impede SMEI progression.

SCN1A antagonists can also be used as neuroprotective agents following ischemia. Neuroprotection refers to an ameliorative effect of neuronal injury following cessation or severely reduced blood flow, for example as in stroke or cardiac arrest. Sodium channel blockers can show neuroprotective effects, possibly by inhibition of electrical depolarization and glutamate release (Squire et al., 1995; Hickenbottom & Grotta, 1998).

In another embodiment of the invention, antagonists of SCN1A can be used for cancer therapy, alone or in combination with other anticancer therapies (e.g., chemotherapy, radiation). SCN1A expression is detected in human prostrate cancer cell lines. Levels of SCN1A expression are further elevated in metastatic cell lines, implicating a role for SCN1A in cancer metastasis (Diss et al., 2001). Thus, antagonism of SCN1A expression and/or activity can be useful for development of anticancer therapies.

In another embodiment of the invention, agonists of SCN1A function can be used to treat pathologies resulting from low levels of expression of SCN1A and/or low levels of SCN1A activity. Alternatively, a construct encoding recombinant SCN1A as disclosed herein can be used to replace diminished or lost sodium channel function. For example, sodium channel expression is reduced in cases of severe neuronal impairment, suggesting that stimulation of sodium channel expression or function can inhibit further dysfunction. See e.g., Stoll & Galdzicki (1996) *Int J Dev Neurosci* 14:749–760. Sodium channel expression is also down-regulated in some responses to injury, and thus elevation of sodium channel expression or function can also be used to ameliorate pain. See Waxman et al. (2000) *J Rehabil Res Dev* 37:517–528, and references cited therein.

Modulators of SCN1A activity identified as disclosed herein can also be useful for modulation of other sodium channel alpha subunits, for example any one of SCN2A, SCN2A2, SCN3A, SCN4A, SCN5A, SCN6A, SCN7A, SCN8A, SCN9A, SCN10A, SCN11A, and combinations thereof. See Lehmann-Horn & Jurkat-Rott (1999) *Physiol Rev* 79:1317–1372, and references cited therein.

Thus, modulators of SCN1A activity can be used for the treatment of disorders relating to misregulation of voltage-gated sodium channel alpha subunit activity including but not limited to paralysis (e.g., hyperkalemic periodic paralysis), paramyotonia congenita, potassium-aggravated myotonia, long Q-T syndrome 3, motor endplate disease, ataxia, diseases of the gastrointestinal tract due to dysfunction of the enteric nervous system (e.g., colitis, ileitis, inflammatory bowel syndrome); diseases of the cardiovascular system (e.g., hypertension and congestive heart failure); diseases of the genitourinary tract involving sympathetic and parasympathetic innervation (e.g., benign prostrate hyperplasia, impotence); diseases of the neuromuscular system (e.g., muscular dystrophy, multiple sclerosis, epilepsy).

IX.A. Preparation of a Composition

The present invention also provides a method for preparing a composition comprising a SCN1A modulator or a recombinantly expressed SCN1A polypeptide. Such a composition can comprise a drug carrier and can be formulated in any manner suitable for administration to a subject. Optionally, the composition can further comprise a targeting ligand to facilitate delivery to a site in need of treatment.

Drug Carriers. Any suitable drug delivery vehicle or carrier can be used, including but not limited to a gene therapy vector (e.g., a viral vector or a plasmid), a microcapsule, for example a microsphere (U.S. Pat. Nos. 5,871,778 and 5,690,954) or a nanosphere (U.S. Pat. Nos. 6,207,195 and 6,177,088), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman, 1997) and U.S. Pat. Nos. 4,551,482, 5,714,166, 5,510,103, 5,490,840, and 5,855,900), and a polysome (U.S. Pat. No. 5,922,545).

Gene Therapy Constructs. A gene therapy construct of the present invention can comprise: (a) a gene therapy vector; and (b) a nucleic acid molecule encoding a nucleic acid, peptide, or polypeptide that modulates SCN1A activity, wherein the nucleic acid encoding segment is operatively linked to a promoter.

A gene therapy construct of the present invention can also comprise: (a) a gene therapy vector; and (b) a nucleic acid molecule encoding a SCN1A polypeptide operatively linked to a promoter. Preferably, a gene therapy construct is prepared as described herein for recombinant expression of a SCN1A polypeptide. Thus, a gene therapy construct of the invention preferably comprises: (a) a nucleotide sequence comprising the nucleotide sequence of SEQ ID NO:1, further comprising one or more mutations, wherein the one or more mutations disrupt regions having a high spontaneous mutation rate; or (b) a nucleotide sequence substantially identical to SEQ ID NO:1, further comprising one or more mutations, wherein the one or more mutations disrupt regions having a high spontaneous mutation rate. Preferably, a SCN1A nucleic acid that can be recombinantly expressed comprises: (a) a nucleic acid molecule comprising a nucleotide sequence of SEQ ID NO:3; or (b) a nucleic acid molecule that is substantially identical to SEQ ID NO:3, and wherein the nucleic acid molecule comprises a T to C transition at each of nucleotide positions 1206 and 1209 of SEQ ID NO:3.

A gene therapy construct for widespread central nervous system expression of a heterologous nucleic acid can employ a platelet-derived growth factor (PDGF) β-chain promoter (Games et al., 1995). For neuron-specific expression, useful promoters include a neuron-specific enolase (NSE) promoter (Forss-Petter et al., 1990; Peel et al., 1997; Klein et al., 1998) and hybrid cytomegalovirus promoters (CMV), for example a CMV/human β-globin hybrid promoter (Mandel et al., 1998) and a CMV/chicken β-actin promoter (Niwa et al., 1991; Dhillon et al., 1999). A glial acidic fibrillary (GFAP) promoter can be used to direct heterologous expression in glia and a subset of neurons (Games et al., 1995). The GFAP promoter is further activated following injury and thus can be useful for gene expression in response to trauma. A myelin basic protein promoter can be used for expression in oligodendrocytes (Ikenaka & Kagawa, 1995; Chen et al., 1998; Chen et al., 1999).

A gene therapy construct of the present invention can also employ an inducible promoter. For example, a tetracycline responsive promoter has been used effectively to regulate transgene expression in rat brain (Mitchell & Habermann, 1999). Other inducible promoters include hormone-inducible promoters (No et al., 1996; Abruzzese et al., 1999; Burcin et al., 1999), radiation-inducible promoters, such as those employing the Egr-1 promoter or NF-□B promoter (Weichselbaum et al., 1991; Weichselbaum et al., 1994), and heat-inducible promoters (Madio et al., 1998; Gerner et al., 2000; Vekris et al., 2000).

A gene therapy construct can comprise any suitable vector, including but not limited to viruses, plasmids, water-oil emulsions, polyethylene imines, dendrimers, micelles, microcapsules, liposomes, and cationic lipids. Where appropriate, two or more types of vectors can be used together. For example, a plasmid vector can be used in conjunction with liposomes. See e.g., U.S. Pat. No. 5,928,944.

Targeting Ligands. The term "target cell" as used herein refers to a cell intended to be treated by a therapeutic agent. A target cell is preferably a cell in a subject in need of therapeutic treatment. For example, a target cell can comprise a cell having abnormal sodium channel activity.

As desired, compositions of the present invention can include a targeting or homing molecule that facilitates delivery of a drug comprising a SCN1A modulator to an intended in vivo site. A targeting molecule can comprise, for example, a ligand that shows specific affinity for a target molecule in the target tissue. See U.S. Pat. Nos. 6,068,829 and 6,232,287. A targeting molecule can also comprise a structural design that mediates tissue-specific localization. For example, extended polymeric molecules can be conjugated to drugs to mediate tumor localization (U.S. Pat. No. 5,762,909).

Antibodies, peptides, or other ligands can be coupled to drugs or drug carriers using methods known in the art, including but not limited to carbodiimide conjugation, esterification, sodium periodate oxidation followed by reductive alkylation, and glutaraldehyde crosslinking. See Goldman et al. (1997) *Cancer Res* 57:1447–1451; Cheng (1996) *Hum Gene Ther* 7:275–282; Neri et al. (1997) *Nat Biotechnol* 15:1271–1275; Nabel (1997), *Current Protocols in Human Genetics*. John Wiley & Sons, New York, Vol. on CD-ROM; Park et al. (1997) *Adv Pharmacol* 40:399–435; Pasqualini et al. (1997) *Nat Biotechnol* 15:542–546; Bauminger & Wilchek (1980) *Methods Enzymol* 70:151–159; U.S. Pat. No. 6,071,890; and European Patent No. 0 439 095.

Formulation. A composition of the present invention preferably comprises a pharmaceutically acceptable carrier. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some preferred ingredients are sodium dodecyl sulfate (SDS), for example in the range of about 0.1 to about 10 mg/ml, preferably about 2.0 mg/ml; and/or mannitol or another sugar, for example in the range of 10 to 100 mg/ml, preferably about 30 mg/ml; and/or phosphate-buffered saline (PBS). Any other agents conventional in the art having regard to the type of formulation in question can be used.

The therapeutic regimens and compositions of the invention can be used with additional adjuvants or biological response modifiers including, but not limited to, the cytokines IFN-α, IFN-γ, IL2, IL4, IL6, TNF, or other cytokine affecting immune cells.

IX.B. Administration

Suitable methods for administering a drug of the present invention to a subject include but are not limited to systemic administration, parenteral administration (including intravascular, intramuscular, intraarterial administration), oral delivery, subcutaneous administration, inhalation, intratracheal installation, surgical implantation, transdermal delivery, local injection, and hyper-velocity injection/bombardment. Where applicable, continuous infusion can enhance drug accumulation at a target site (e.g., U.S. Pat. No. 6,180,082).

The particular mode of drug administration of the present invention depends on various factors, including but not limited to the vector and/or drug carrier employed, the severity of the condition, and mechanisms for metabolism or removal of the drug from its site of administration.

The administration method can further include treatments for enhancing drug delivery. For example, electromagnetic waves or ultrasonic radiation can be used to enhance drug delivery in solid tumors (U.S. Pat. No. 6,165,440). Heating of the particles or movement of the particles in response to ultrasonic waves results in perforation of tumor blood vessels, microconvection in the interstitium, and perforation of cancer cell membranes, thereby facilitating movement of intravascularly administered drugs to tumor cells. See also, U.S. Pat. No. 6,234,990. Other methods include ionotophoresis (U.S. Pat. Nos. 6,001,088; 5,499,971), electroporation (U.S. Pat. No. 6,041,253), electromagnetic field generation by ultra-wide band short pulses (U.S. Pat. No. 6,261,831), and hormone treatment (U.S. Pat. No. 5,962,667).

The administration method can also include treatments for drug release or drug activation. For example, a composition comprising a therapeutic agent conjugated to a drug carrier or targeting molecule via a selectively hydrolyzable bond can be released by local provision of a hydrolyzing agent (U.S. Pat. No. 5,762,918). In the case of a gene therapy construct, gene expression of a therapeutic polypeptide or therapeutic oligonucleotide can be regulated using an inducible promoter. Thus an administration method can further comprise a method for induction of a gene therapy construct.

The administration method employed can include any treatment that augments drug efficacy.

The term "subject" as used herein refers to any invertebrate or vertebrate species. The methods of the present invention are particularly useful in the treatment and diagnosis of warm-blooded vertebrates. Thus, the invention concerns mammals and birds. More particularly, contemplated is the treatment and/or diagnosis of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

In a preferred embodiment of the invention, a subject comprises a mammal, or more preferably a human.

IX.C. Dose

For therapeutic applications, a therapeutically effective amount of a composition of the invention is administered to a subject. A "therapeutically effective amount" is an amount of the therapeutic composition sufficient to produce a measurable biological response (for example, but not limited to, a change in sodium ion current, an antiepileptic response, an anticonvulsant response, an anesthetic effect, and a neuroprotective response). Actual dosage levels of active ingredients in a therapeutic composition of the invention can be varied so as to administer an amount of the active compound(s) that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For administration of therapeutic compositions comprising a small molecule, conventional methods of extrapolating human dosage based on doses administered to a murine animal model can be carried out using the conversion factor for converting the mouse dosage to human dosage: Dose Human per kg=Dose Mouse per kg×12 (Freireich et al., 1966). Drug doses can also given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al. (1966) *Cancer Chemother Rep* 50:219–244. Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/sq m. See also U.S. Pat. Nos. 5,326,902 and 5,234,933, and PCT International Publication No. WO 93/25521.

For local administration of viral vectors, previous clinical studies have demonstrated that up to $10^{13}$ pfu of virus can be injected with minimal toxicity. In human patients, $1 \times 10^9 – 1 \times 10^{13}$ pfu are routinely used. See Habib et al. (1999) *Human Gene Therapy* 12:2019–2034. To determine an appropriate dose within this range, preliminary treatments can begin with $1 \times 10^9$ pfu, and the dose level can be escalated in the absence of dose-limiting toxicity. Toxicity can be assessed using criteria set forth by the National Cancer Institute and is reasonably defined as any grade 4 toxicity or any grade 3 toxicity persisting more than 1 week. Dose is also modified to maximize SCN1A expression.

For additional guidance regarding dose, see Berkow et al. (1997) *The Merck Manual of Medical Information*, Home ed. Merck Research Laboratories, Whitehouse Station, N.J.; Goodman et al. (1996) *Goodman & Gilman's the Pharmacological Basis of Therapeutics*, 9th ed. McGraw-Hill Health Professions Division, New York; Ebadi (1998) *CRC Desk Reference of Clinical Pharmacology*. CRC Press, Boca Raton, Fla.; Katzung (2001) *Basic & Clinical Pharmacology*, 8th ed. Lange Medical Books/McGraw-Hill Medical Pub. Division, New York; Remington et al. (1975) *Remington's Pharmaceutical Sciences*, 15th ed. Mack Pub. Co., Easton, Pa.; Speight et al. (1997) *Avery's Drug Treatment: A Guide to the Properties, Choice, Therapeutic Use and Economic Value of Drugs in Disease Management*, 4th ed. Adis International, Auckland/Philadelphia; Duch et al. (1998) *Toxicol Lett* 100–101:255–263.

EXAMPLES

The following Examples have been included to illustrate modes of the invention. Certain aspects of the following Examples are described in terms of techniques and procedures found or contemplated by the present co-inventors to work well in the practice of the invention. These Examples illustrate standard laboratory practices of the co-inventors. In light of the present disclosure and the general level of skill in the art, those of skill will appreciate that the following Examples are intended to be exemplary only and that numerous changes, modifications, and alterations can be employed without departing from the scope of the invention.

Example 1

Cloning of Human SCN1A cDNA

A 6030 base pair nucleic acid segment comprising a complete coding region of human SCN1A was isolated and is set forth as SEQ ID NO:3. FIG. 1 depicts the construction of a complete coding region based on four overlapping partial cDNAs.

For amplification of SCN1A sequences, publicly available genomic sequence available from the National Center for Biotechnology Information was used to design primers (SEQ ID NOs:10–17) corresponding to putative SCN1A sequence. To enhance ligation efficiency, forward and reverse primers included 5' terminal sequences (SEQ ID NOs:18 and 19, respectively) that enhance generation of A-overhangs by Taq polymerase. Primers also included restriction enzymes sites to facilitate assembly of the overlapping partial cDNAs.

Reverse-transcriptase polymerase chain reaction (RT-PCR) was performed using human cerebral cDNA as template (Clontech of Palo Alto, Calif., United States of America). Amplified PCR products were directly cloned into the PCR®2.1-TOPO® vector and transformed into ONE SHOT® TOP10 cells according to the TOPO-TA® cloning system (INVITROGEN™ Life Technologies, Inc. of Carlsbad, Calif., United States of America). Transformed cells were grown on Luria Broth (LB) plates supplemented with 50 µg/ml kanamycin at 37° C. overnight. Individual colonies were used to innoculate 2-ml cultures (LB plus 50 µg/ml kanamycin), which were also grown at 37° C. overnight. Plasmid DNA was isolated using a QIAPREP® 8 Turbo miniprep kit (Qiagen of Valencia, Calif., United States of America).

The nucleotide sequence of cloned PCR products was confirmed by restriction enzyme fingerprinting and automated fluorescent DNA sequence analysis. Polymerase errors were repaired by site-directed mutagenesis or by subcloning wild type fragments from other partial clones.

Two silent mutations (T1206C and T1209C) were introduced to disrupt a short poly-T repeat region that exhibited a high rate of spontaneous mutation. The mutated SCN1A variant is set forth as SEQ ID NO:3. This clone was propagated at 30° C. in STBL2™ high efficiency competent cells (INVITROGEN™ Life Technologies, Inc. of Carlsbad, Calif., United States of America) to suppress additional mutation.

The four overlapping SCN1A partial cDNAs were digested using restriction enzymes and sequentially ligated into the SalI and NotI sites of the mammalian expression plasmid PCMV-SCRIPT™ (Stratagene of La Jolla, Calif., United States of America). Ligation products were propagated in STBL2™ high efficiency competent cells (INVITROGEN™ Life Technologies, Inc. of Carlsbad, Calif., United States of America). Transformed cells were selected using lowered antibiotic concentration (LB plates plus 25 µg/ml kanamycin) at 30° C. for at least 30 hours. Cultures for plasmid isolation used individual colonies to innoculate terrific broth plus 25 µg/ml kanamycin.

Full-length SCN1A cDNA constructs were analyzed by enzyme fingerprinting and automated fluorescent DNA sequence analysis. The construct comprising the full-length SCN1A cDNA is designated and referred to herein as "pCMV-SCN1A."

Example 2

Transient Recombinant Expression of a Human SCN1A Polypeptide

SCN1A was transiently expressed in tsA201 human embryonic kidney cells. Cells were grown in FALCON® 6-cm plastic tissue culture dishes (available from Applied Scientific of South San Francisco, Calif., United States of America) containing 3 ml Dubelco's Modified Eagle Medium (DMEM available from INVITROGEN™ Life Technologies, Inc. of Carlsbad, Calif., United States of America) supplemented with 10% fetal bovine serum, 1% glutamine, and 1% penicillin and streptomycin. Transfections were performed using 5 µg of pCMV-SCN1A and SUPERFECT® transfection reagent (Qiagen of Valencia, Calif., United States of America). A plasmid encoding EGFP (e.g., GenBank Accession No. U55762) was co-transfected as a reporter to select transfected cells for physiological experiments. Optionally, constructs encoding human sodium channel β1 (SEQ ID NOs:4–5), human sodium channel β2 (SEQ ID NOs:6–7), or a combination thereof, were co-transfected with pCMV-SCN1A.

Cells were incubated for at least 24 hours prior to the next passage and before electrophysiology experiments. Transfected cells were suitable for assays described herein for at least 2–3 days following transfection.

To elaborate, mammalian cells (tsA201) were raised in 6-cm plastic dishes (Falcon Cat. # 35 3004) containing 3 ml Dubelco's Modified Eagle Medium ("DMEM", Life Technologies, Cat. # 11965-084) supplemented with 10% fetal bovine serum, 1% glutamine, and 1% penicillin/streptomycin. A water-jacket incubator provided humid conditions in a 5% $CO_2$ atmosphere at 37° C. The cells were passed every three days at 80% confluency up to passage 16, where a new cell line was started. Generally, 5 µg of Maxiprep DNA were used according to the Qiagen SUPERFECT® protocol (Cat. # 301305) at a transfectant concentration of 6 µl per microgram DNA. Plasmids containing sodium channel subunits β1 and β2 and transfections markers CD8 and GFP, respectively, were co-transfected with 500 ng DNA each. Cells were incubated over night and, when necessary, passed 1:10 at least 24 hours before the experiment.

Example 3

Preparation of a Stable Cell Line Expressing a Recombinant Human SCN1A Polypeptide To create a cell line stably expressing SCN1a, HEK-293 human embryonic kidney cells are transfected with pCMV-SCN1a using SUPERFECT® transfection reagent (Qiagen of Valencia, Calif., United States of America). Beginning at 24 hours after transfection, cells are exposed continuously to media containing the aminoglycoside antibiotic G418 (400 µg/ml) to eliminate non-transfected cells. About 2 weeks later, G418-resistant colonies are selected using cloning rings, expanded in 24-well plates, and assayed for sodium currents using whole-cell patch clamp recording (Example 4). Cell lines stably expressing SCN1A polypeptides are maintained using continuous G418 selection and tested frequently (e.g., using electrophysiological assays or any other appropriate assay) to demonstrate SCN1A expression.

Example 4

Electrophysiological Assays to Demonstrate a Functional SCN1A Polypeptide

Cells were dissociated with trypsin/EDTA (INVITROGEN™ Life Technologies, Inc. of Carlsbad, Calif., United States of America). Pre-warmed supplemented DMEM was added to the dissociated cells, and the cells were immediately transferred into a microscope acquisition chamber. In the chamber, the cells were superfused with 310 mmol/kg of Tyrode's solution (145 mM NaCl, 4 mM KCl, 1.8 mM $CaCl_2$, 1 mM $MgCl_2$, 10 mM HEPES, pH 7.35) at room temperature for at least 1 hour.

Physiological analysis was performed using an OLYMPUS® IX50 inverted fluorescence microscope (Olympus Optical Co. Ltd. of Tokyo, Japan) equipped with a micromanipulator (Burleigh Instruments, Inc. of Victor, N.Y., United States of America. Cells expressing SCN1A (prepared as described in Example 2) were selected for data acquisition based on co-expression of EGFP. Currents were measured in whole-cell mode using an AXOPATCH™ 200 amplifier with a CV-201 headstage and PCLAMP® software (all available from Axon Instruments, Inc. of Union City, Calif., United States of America).

Borosilicate pipettes (outer diameter 1.2 mm, inner diameter 0.94 mm, available from Warner Instrument Corp. of Hamden, Conn., United States of America) were pulled and fire polished to 1 MΩ to 1.5 MΩ using a pipette puller (model P-97 available from Sutter Instruments of Novato, Calif.) and a NARASHIGE™ microforge (model MF-830 available from Micro Instruments of Oxford, United Kingdom). The pH of the internal pipette solution (10 mM NaF, 110 mM CsF, 20 mM CsCl, 2 mM EGTA, and 10 mM HEPES) was matched to the pH of the bath solution and diluted 10% with water to prevent osmotic swelling.

Data acquisition was started after stabilization of the leak current (typically 10 minutes after establishing the whole-cell patch clamp). Cells were tested for current using a simple 20-millisecond test pulse to 0 mV from a holding potential of −120 mV. Cells generating less than −0.8 nA or more than −6.0 nA were excluded. All data were corrected for the pipette junction potential, the pipette capacitance, and the whole-cell capacitance, using the internal AXO-PATCH™ amplifier (available from Axon Instruments, Inc. of Union City, Calif., United States of America) compensation. A BESSEL™ low-pass filter (SDL, Inc. of San Jose, Calif., United States of America) at 5 kHz was used at all times.

To elaborate, cells were dissociated with 37° C. trypsin/EDTA (Life Technologies, Cat. # 25200-056). After adding pre-warmed supplemented DMEM 12:1, the cells were allowed to recover at 37° C. for at least 30 min. Following the addition of 3 µl of CD8 antibody-covered beads (DYNABEADS® M-450, Dynal ASA, Oslo, Norway, Cat. # 111.07) the cells were transferred into the microscope's acquisition chamber, where they were superfused with room-temperature Tyrode's solution (in mM: NaCl 145, KCl 4, $CaCl_2$ 1.8, $MgCl_2$ 1, HEPES 10, pH 7.35, 310 mmol/kg) for at least 10 min prior to acquisition. All experiments were performed on an Olympus IX50 inverted fluorescence microscope equipped with Burleigh micromanipulators CS 5000. Isolated, small to medium-sized, greenly fluorescent cells with at least two beads were selected for data acquisition. Currents were Measured in whole-cell mode using an AXO-PATCH™ 200/200B with CV-201/203BU headstage and the pCLAMP software package (Axon Instruments). Borosilicate pipettes (outer diameter (O.D.) 1.2 mm, inner diameter (I.D.) 0.94 mm, Warner Instrument Corp. Cat. # GC120TF-7.5) were pulled and fire polished to 0.8–1.5 MΩ (P-97, Sutter Instruments and Micro Forge MF-830, Narashige, respectively). The internal pipette solution (in mM: NaF 10, CsF 110, CsCl 20, EGTA 2, HEPES 10) was matched in pH and osmolality to the bath solution.

Data acquisition was started after stabilization of the leak current, which usually took about 5 min. Cells were tested for current using a simple 20-msec test pulse to 0 mV from a holding potential of −120 mV. While most cells showed peak currents between −1 to −2 nA, diverging results were encountered frequently. To avoid falsification of the data by intrinsic voltage-sensitive $Na^+$ currents or by inadequately voltage-clamped cells, cells generating less than −0.8 nA or more than −6 nA, respectively, were excluded. All data were corrected for the pipette junction potential, as well as the pipette and the whole-cell capacitance, using the internal AXOPATCH™ compensation. A lowpass BESSEL™ filter at 5 kHz was used at all times.

Leak was subtracted using software. Cells displaying leaks exceeding 5% of the peak current measured during a test pulse were excluded from the data pool.

Whole-cell capacitive currents were assessed after adjusting for pipette capacitance by integrating the transient current elicited by a 10-mV voltage step from −120 mV to −110 mV filtered at 10 kHz.

Figure 2A:
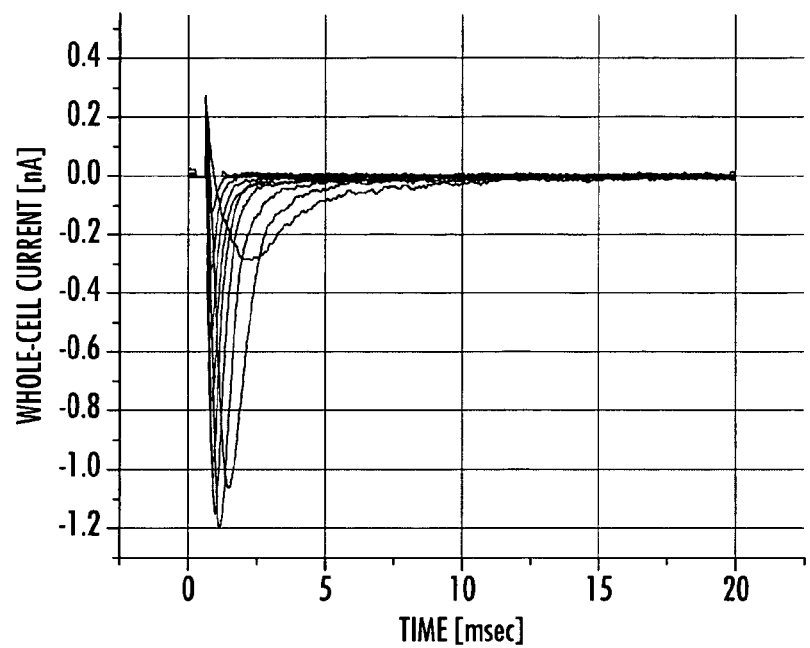
FIGS. 2A–2B are raw physiological recordings obtained from recombinant cells expressing SCN1A, performed as described in Example 4.
Figure 2B:
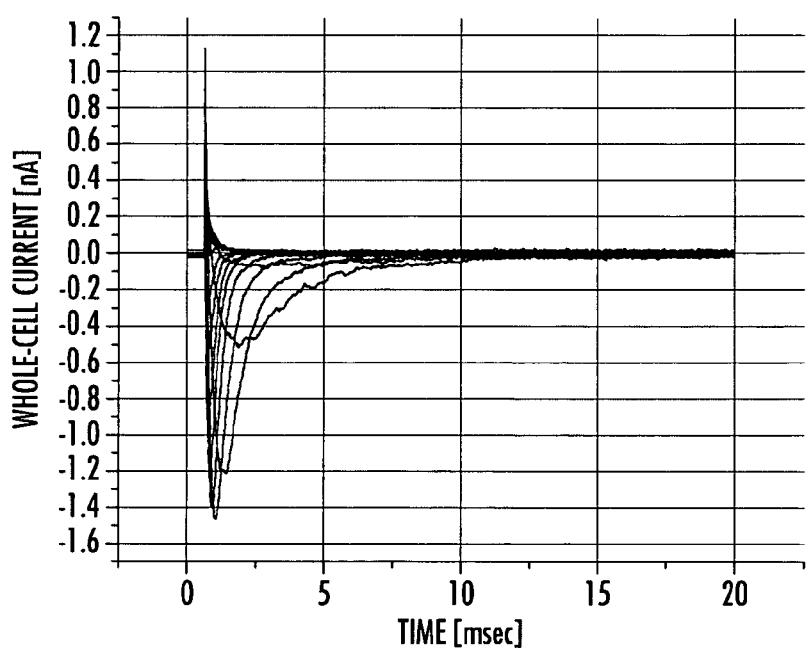
Figure 2C:
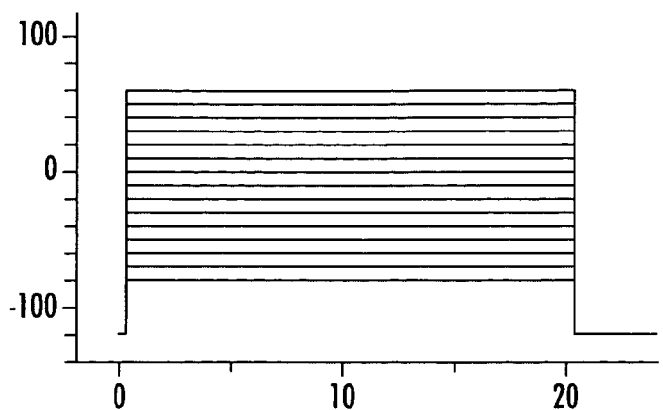
FIG. 2C is a recording of potential (mV) of cells as in FIGS. 2A–2B. Cells were clamped to various step potentials for 20 milliseconds every 5 seconds.
Figure 3A:
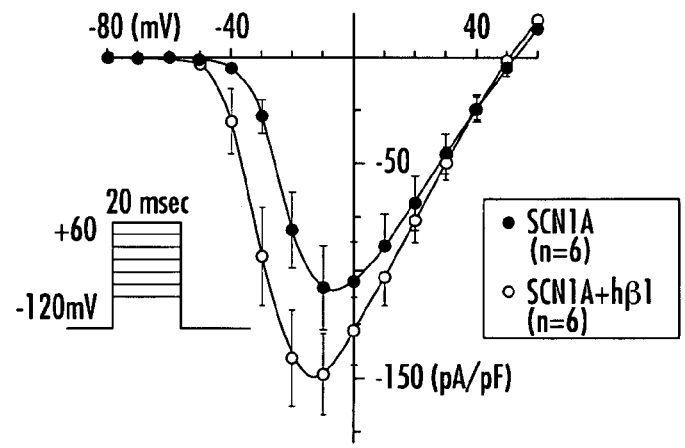
FIGS. 3A–3C present electrophysiological data obtained from recombinant cells expressing SCN1A performed as described in Example 4. Whole-cell currents were acquired at least 24 hours after transfection.
Figure 3B:
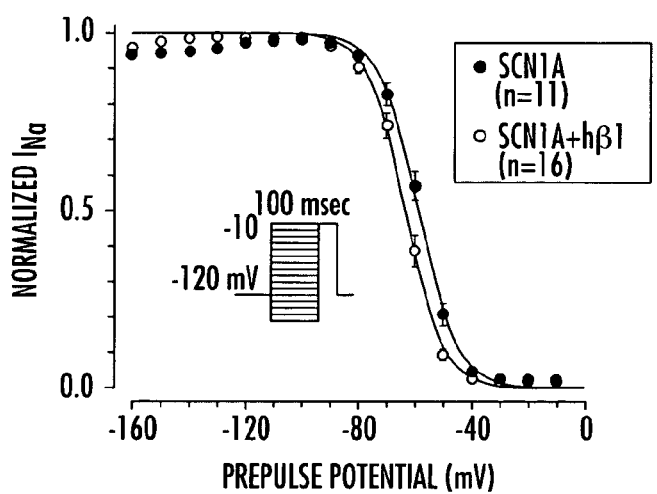
Figure 3C:
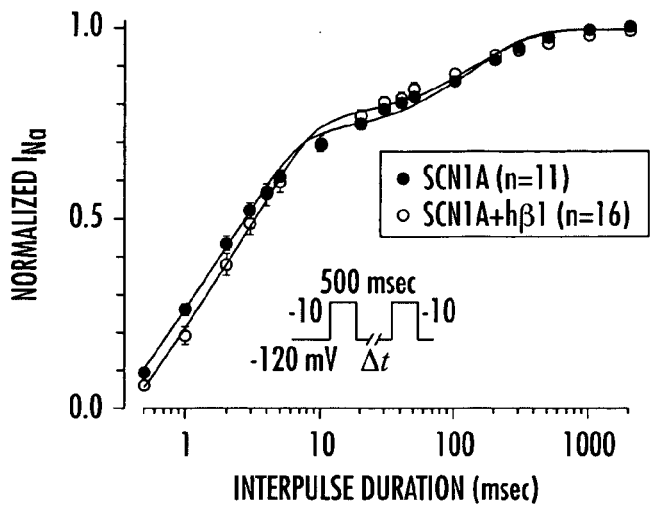
Figure 4A:
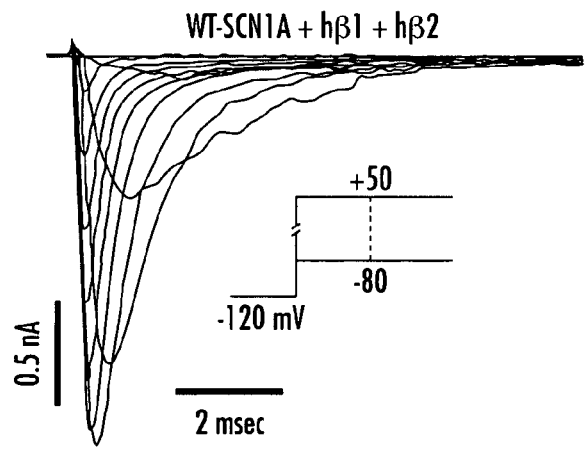
FIGS. 4A–4D depict electrophysiological data from mammalian tsA201 cells transfected with pCMV-Scrip™ containing full-length SCN1A. Sodium channel subunits $\beta_1$ and $\beta_2$ w¯r¯ co-transfected at a ratio of 5:1 to the α subunit in bicistronic IRES vectors containing the CD8 gene and the GFP gene, respectively, as a marker. Whole-cell currents were acquired 24 hrs+ after transfection. Pulse protocols are inserted into the individual panels.
Figure 4B:
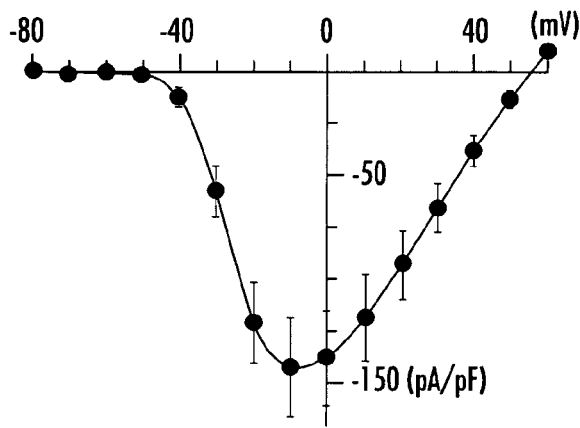
Figure 4C:
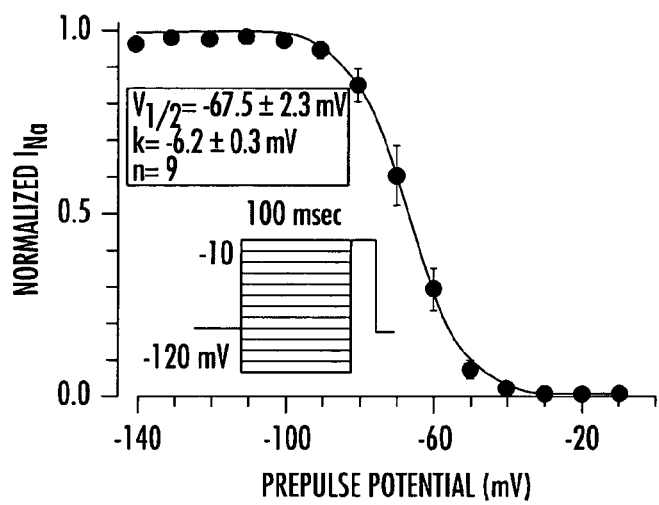
Figure 4D:
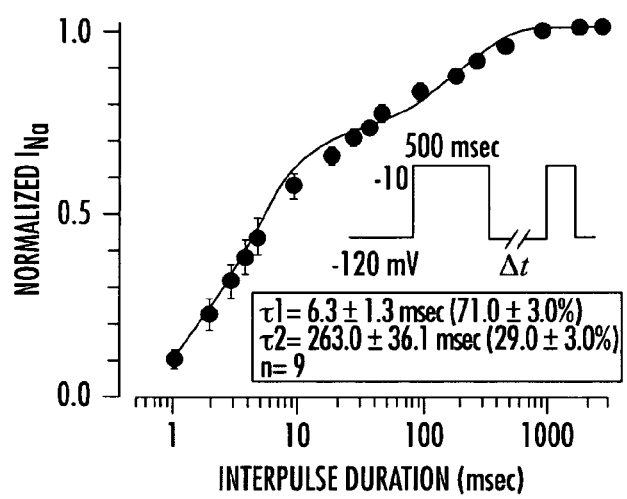

FIGS. 2A–2C illustrate representative whole-cell SCN1A currents in the presence and absence of SCN1B. Rapidly activating and inactivating inward currents are observed that resemble typical voltage-gated sodium channels. FIGS. 3A–3C illustrate the analysis of the current-voltage relationship, voltage-dependence of steady-state inactivation, and the time course of recovery from inactivation. FIGS. 4A–4D illustrate electrophysiological data from mammalian tsA201 cells transfected with pCMV-SCRIPT™ containing full-length SCN1A.

Example 5

Cloning and Functional Expression of Human SCN1A

The complete coding region (6030 bp) of human SCN1A (designated NaV1.1 by some in the art, see e.g. Goldin, A. L. et al. Neuron 28:365–368 (2000)) with 873 bp of the 3′-untranslated region was deduced from publicly available genomic sequence and isolated as four overlapping cDNAs using reverse-transcriptase polymerase chain reaction (RT-PCR) cloning as defined in Methods.

Two splice variants were also identified through sequencing of independently isolated cDNAs and are presented herein as SEQ ID NOs:20 and 22 (amino acids sequences SEQ ID NOs:21 and 23, respectively). Both variants result from utilization of alternative splice donor sequences contained within exon 11 and produce in frame deletions of 33 and 84 nucleotides from the 3′ end of this exon (encoding the cytoplasmic region between domains I and II).

In one SCN1A splice variant cDNA (SEQ ID NO: 20; −33N; SCN1AΔn2011–2043) the following 33 nucleotides were missing (Δn33): GTG ATA ATA GAT AAG CCA GCT ACT GAT GAC AAT (SEQ ID NO: 24). To obtain WT SCN1A sequence, insert the above 33 nucleotides (Δn33) into SEQ ID NO: 20 with the first G of Δn33 being position 2011. In the corresponding SCN1A splice variant protein (SEQ ID NO: 21) the following amino acid residues are missing (Δp11): VIIDKPATDDN (SEQ ID NO: 25). To obtain WT SCN1A sequence, insert the above 11 amino acids (Δp11) into SEQ ID NO: 21 with valine (V) of Δp11 being position 671.

In another SCN1A splice variant cDNA (SEQ ID NO: 22; −84N; SCN1AΔn1960–2043) the following 84 nucleotides were missing (Δn84): GTT GGT GGA CCT TCA GTT CCT ACA TCG CCT GTT GGA CAG CTT CTG CCA GAG GTG ATA ATA GAT AAG CCA GCT ACT GAT GAC AAT (SEQ ID NO:26). To obtain WT SCN1A sequence, insert the above 84 nucleotides (Δn84) into SEQ ID NO: 22 with the first G of Δn84 being position 1960. In the corresponding protein (SEQ ID NO: 23; −84P; SCN1AΔp654–681) the following amino acid residues are missing (Δp28): VGGPSVPTSPVGQLLPEVIIDKPATDDN (SEQ ID NO: 27). To obtain WT-SCN1A sequence, insert the above 28 amino acids (Δp28) into SEQ ID NO: 23 with valine (V) of Δp28 being position 654.

The assembled SCN1A cDNA (non-variant form) in a mammalian expression plasmid was transiently transfected into tsA201 cells along with plasmids encoding the human β1 and β2 sodium channel subunits coupled with distinct reporter genes (CD8 antigen and green fluorescent protein, respectively). Transfected cells expressing both reporters and exhibiting inward sodium currents were used for electrophysiological recording experiments.

Figure 5A:
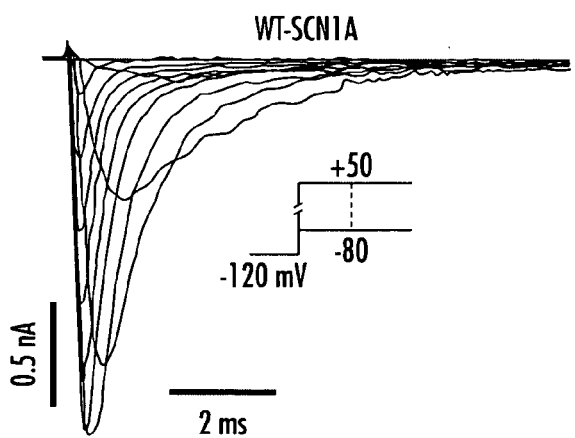
FIGS. 5A–5D depict functional characterization of WT-SCN1A in tsA-201 cells.
Figure 5B:
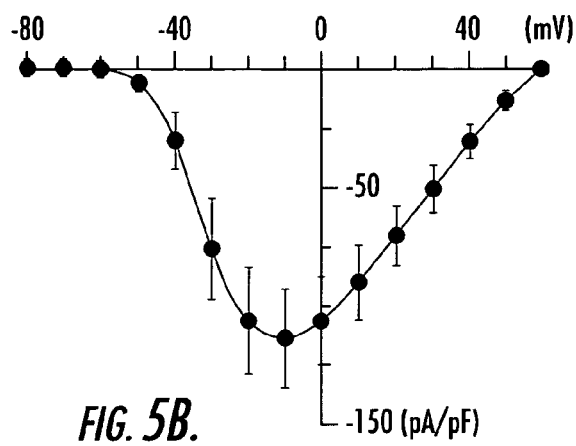
Figure 5C:
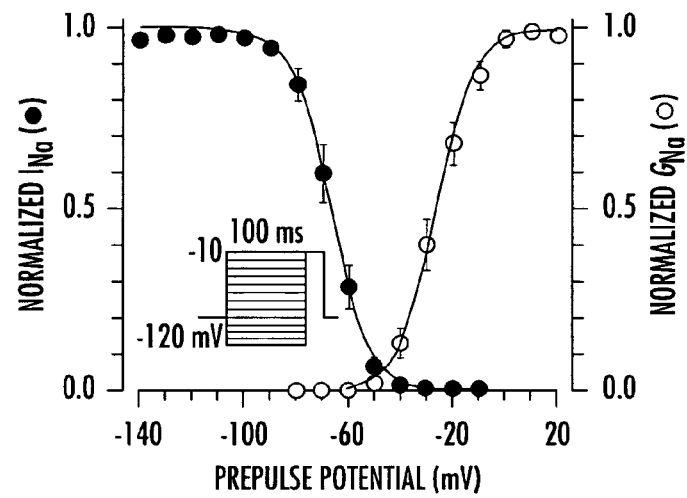
Figure 5D:
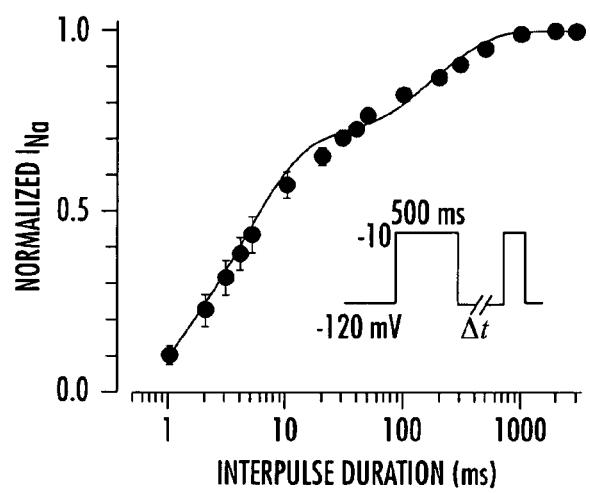

FIGS. 5A–5D illustrate the biophysical behavior of recombinant wild-type (WT) SCN1A co-expressed with human β1 and β2 subunits. Rapidly activating and inactivating, voltage dependent inward currents were observed in response to depolarizing test potentials and were generally robust (typical peak current amplitude range 1–5 nA, FIG. 5A). In the absence of the accessory β subunits, SCN1A expression was not consistent. Endogenous inward currents larger than 0.2 nA were never observed in non-transfected cells. Peak activation of sodium current occurs at −10 mV (FIG. 5B) and the expressed currents were highly tetrodotoxin (TTX) sensitive. Voltage-dependent channel availability and activation were half-maximal at −67.5±2.3 and −26.4±2.3 mV, respectively (FIG. 5C). Recovery from inactivation following a 500 msec depolarization exhibited two exponential components (FIG. 5D) with a predominant fast (time constant, $\tau_f$=6.4±1.3 ms, 71±3%) and smaller slow component ($\tau_s$=263±36 ms, 29±3%). All of these properties are consistent with voltage-gated sodium channels and closely resemble native human neuronal sodium channel activities that have been described in various tissue preparations. Reckziegel, G., et al., *J Physiol* (London) 509 (Pt 1):139–150 (1998); Sah, D. W., *J Neurophysiol.* 74:1889–1899 (1995).

Example 6

Epilepsy-Associated SCN1A Mutants Disrupt Inactivation

Figure 6A:
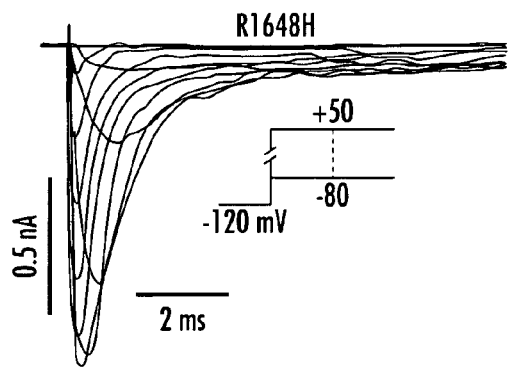
FIGS. 6A–6D depict whole-cell recordings of mutant SCN1A channels. Typical current tracings from transiently transfected tsA201 cells expressing SCN1A mutants R1648H (FIG. 6A), T875M (FIG. 6B) and W1204R (FIG. 6C) recorded at various test potentials between −80 and +50 mV (holding potential was −120 mV). All experiments were performed with co-expressed hβ1 and hβ2.
Figure 6B:
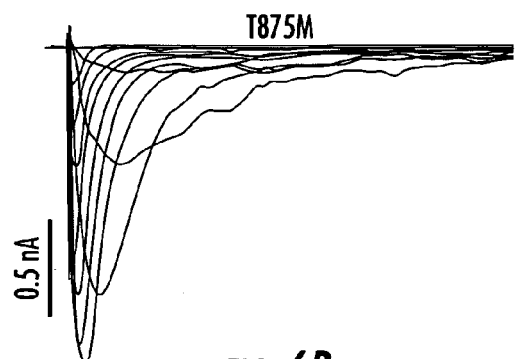
Figure 6C:
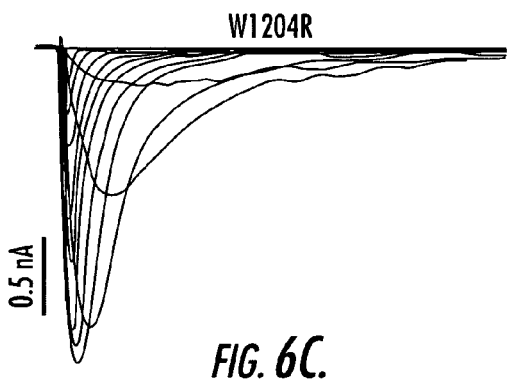
Figure 6D:
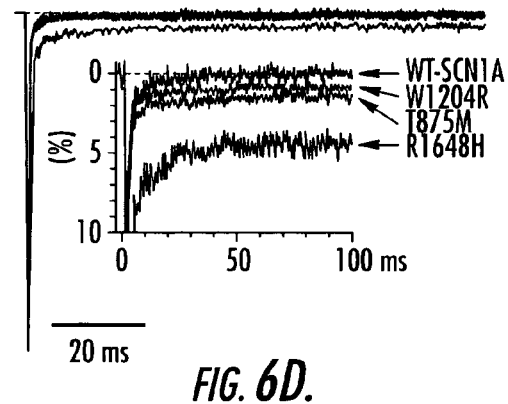

The biophysical properties of three GEFS+ mutants using were examined using the recombinant human SCN1A sodium channel. FIGS. 6A–6C illustrate typical whole-cell records obtained from cells expressing T875M, W1204R or R1648H. All three mutants exhibit robust, rapidly activating and inactivating inward currents in response to a series of test depolarizations. However, close examination of all recordings reveals the presence of non-inactivating inward current in the mutants that was not observed in WT-SCN1A. This non-inactivating current was evident during longer test depolarization (100 milliseconds (ms)) and could be reversibly and completely blocked by the application of 10 µM TTX excluding a leak current (FIG. 6D). The size of the non-inactivating current varied among the mutants, but was largest in R1648H expressing cells (WT-SCN1A, 0.2±0.1%, n=4; R1648H, 4.2±0.6%, n=5, p<0.0005 versus WT-SCN1A; T875M, 1.5±0.2%, n=4, p<0.001 versus WT-SCN1A; W1204R, 0.9±0.2%, n=8, p<0.01 versus WT-SCN1A). This disturbance in fast inactivation associated with GEFS+ mutants was not previously observed when similar mutations where examined in the human SCN4A sodium channel (Spampanato, J., et al. 2001; Alekov, A., et al., 2000, or the rat SCN1A ortholog (Spampanato, J., et al. 2001), suggesting that species and isoform related variables may be important for revealing this critical feature of the mutant sodium channel phenotype. Furthermore, the absence of persistent sodium currents in the work reported by Spampanato et al. (2001) may relate to abnormal inactivation properties commonly observed for recombinant neuronal and muscle sodium channels expressed in *Xenopus oocytes* (Krafte et al., 1990; Moorman et al., 1990; Zhou et al., 1991).

Figure 7:
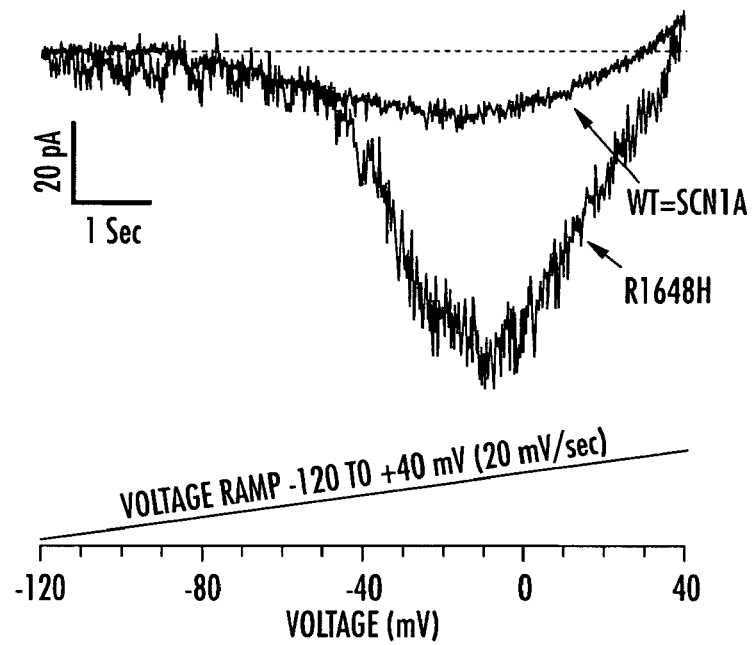
FIG. 7 depicts responses of WT-SCN1A and R1648H to ramp depolarization. Cells were initially voltage clamped to a holding potential of −120 to assure all sodium channels were available. The membrane potential was slowly ramped from −120 mV to +40 mV over 8 seconds (s) (20 mV/s). Traces represent TTX-sensitive currents obtained by digital subtraction of sodium currents recorded before and after TTX (10 μM) addition. The dashed line indicates the zero current level. A representative experiment is illustrated (the peak transient sodium currents were −3.6 nA for WT-SCN1A and −3.2 nA for R1648H). Similar experimental results were observed in four cells for WT-SCN1A and five cells for R1648H.

A characteristic displayed by non-inactivating sodium channels is the inappropriate activation of inward current during a slow depolarization. This feature was demonstrated by comparing the responses of WT-SCN1A to R1648H using the voltage-ramp protocol illustrated in FIG. 7. Slow membrane depolarization triggered a significantly larger inward current in cells expressing R1648H than in WTSCN1A-expressing cells (maximal ramp current divided by the peak transient current×100 (mean±SEM): WTSCN1A, 0.3±0.08%; n=6 versus R1648H, 1.9±0.2%; n=5, p<0.0001).

Figure 8A:
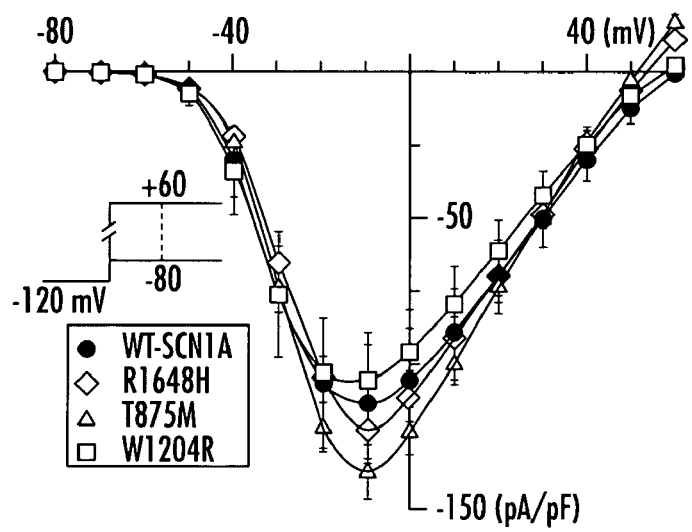
FIGS. 8A–8D depict biophysical characterization of mutant SCN1A channels.
Figure 8B:
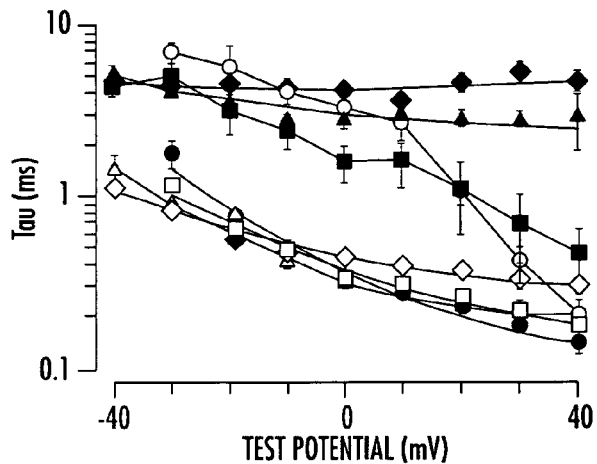
Figure 8C:
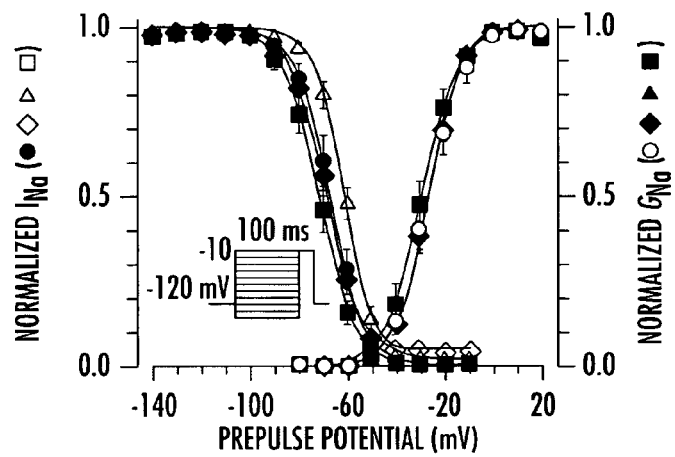
Figure 8D:
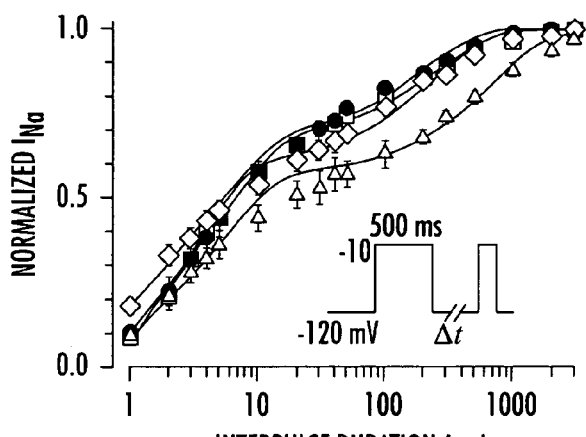

Mutant sodium channels expressed similar current density as WT-SCN1A (FIG. 8A) but exhibited quantitative differences in the voltage-dependence of inactivation (FIG. 8B). Mutant channels generally exhibit less steep voltage-dependence of inactivation especially affecting the slow component. Other biophysical properties of the mutant sodium channels grossly resembled those of WT-SCN1A except for a significant depolarizing shift in the voltage-dependence of channel availability exhibited by T875M, a significant hyperpolarizing shift of channel activation observed for W1204R (FIG. 8C), and an apparent enhancement of the slow component of recovery from inactivation observed for T875M and R1648H (FIG. 8D). Overall, the most consistent defect observed for all three mutant sodium channels is the presence of a non-inactivating current component.

Example 7

Single Channel Analysis

Sodium currents were recorded in excised outside-out patches from cells expressing either WT-SCN1A or the R1648H mutant to resolve single channel behavior. FIGS. 9A–9C illustrate representative patch clamp records from the two conditions. Wild-type sodium channels exhibit predominantly early short-lived (<1 ms) openings followed by infrequent late openings and rare short bursts of re-openings. By contrast, mutant sodium channels exhibit a much higher probability of late openings occurring throughout 250 ms test depolarizations. Multiple late openings were seen in all sweeps recorded from mutant sodium channels and therefore this behavior was not due to an intermittent ("modal") gating defect.

Estimated single-channel conductance at the examined test potential was not different between alleles (WT-SCN1A, patches from cells expressing WT-SCN1A 16.6±0.7 pS (n=7) versus R1648H, 17.3±0.5 pS (n=5); test potential was 0 mV). Ensemble average currents generated from about 400 individual sweeps (FIG. 9C) closely resembled the whole-cell data presented in FIGS. 5A–5D and 6A–6D. These data indicate a significant inactivation defect present in R1648H channels that explains the disturbance in sodium channel behavior observed in whole-cell recordings (FIG. 6D).

Discussion of Examples 5–7

Examples 5–7 extensively investigated the biophysical properties of three distinct GEFS+ associated mutations using a recombinant human SCN1A co-expressed heterologously in cultured mammalian calls with both human β1 and β2 accessory subunits.

Because all essential molecular elements necessary for assembly of human neuronal sodium channels (Catterall, 1992) were provided, the experiments of these Examples have a high likelihood of revealing the true functional defect responsible for this disease. Using this approach, potential concerns regarding the molecular context of previous characterizations of GEFS+ mutations in nonhuman or non-neuronal sodium channels expressed in the absence of one or both β subunits (Alekov et al., 2000, 2001; Spampanato et al., 2001) were circumvented.

These data demonstrate a clear defect in fast inactivation exhibited by GEFS+ mutations R1648H, T875M and W1204R. The observation of a significant persistent non-inactivating current component in the mutants indicates that a common gain-of-function defect in channel gating is responsible for seizure susceptibility in this syndrome. This observation is reminiscent of the channel dysfunction associated with two other human sodium channelopathies: hyperkalemic periodic paralysis and the congenital long QT syndrome. Mutations in genes encoding the muscle sodium channel (SCN4A) (Cannon, S. C., 2000) or the cardiac sodium channel (SCN5A) (Bennett et al., 1995) have been demonstrated to cause defects in fast inactivation manifesting as a small but significant non-inactivating late sodium current.

Interestingly, at the tissue level, this type of channel dysfunction could result in increased excitability such as myotonia in skeletal muscle and ventricular arrhythmias in heart. However in muscle, persistent depolarization of the sarcolemma can also cause widespread inactivation of normal sodium channels leading to excitation failure and paralysis (Cannon et al., 1993). These data provide an important new insight into the pathomechanism of sodium channel dysfunction in epilepsy. It appears that a small non-inactivating inward current will facilitate neuronal hyperexcitability because of a reduced threshold for action potential firing and based on the prediction that action potentials will be prolonged causing increased potassium efflux during repolarization. Increased extracellular potassium will favor further membrane depolarization of the active neuron as well as neighboring fibers, an ephaptic phenomenon that could predispose to hypersynchronous activation of neuronal clusters (Jefferys, J. G., 1995; Dudek et al., 1998). It also appears that this vicious cycle of hyperexcitability and potassium induced depolarization will eventually cause sufficient membrane depolarization to engage slower forms of sodium channel inactivation and inexcitability. This latter phenomenon might explain the transient nature of most seizures in this and other settings.

The variable magnitude of non-inactivating current that was observed for the three distinct GEFS+ mutations can potentially correlate with the severity of the phenotype although genotype-phenotype relationships are difficult to construct reliably at this point from the small number of affected families so far reported. Other biophysical disturbances were also observed in the SCN1A mutants but none were exhibited uniformly by all alleles. These additional functional defects can also help explain subtle phenotypic differences between individuals carrying different mutations.

Genetic modifiers and environmental factors are also likely to impact substantially on disease expression. Individuals with GEFS+ appear to have an intrinsic seizure-prone substrate that can be triggered by fever and other unidentified non-febrile factors. Scheffer, I. E. & Berkovic, S. F., 1997; Singh et al. 1999. Fever appears to be an important nongenetic factor in the triggering of seizures in GEFS+. However, differences in temperature sensitivity between WT and mutant SCN1A alleles were not specifically examined. For a variety of technical reasons including increased thermal noise, excessively rapid gating kinetics and channel rundown, recordings of voltage-gated sodium channels at physiological temperatures are not reliable. Also, seizure susceptibility in GEFS+ is not strictly linked to fever, and most forms of febrile seizures occur in the absence of known sodium channel lesions.

Like in many forms of epilepsy, GEFS+ patients exhibit multiple types of seizures including partial and generalized forms. Scheffer, I. E. & Berkovic, S. F., 1997; Singh et al. 1999; Sugawara et al. 2001; Abou-Khalil, et al., 2001. It is not likely that the common sodium channel defect observed in our studies explains this pleomorphism. Rather it appears that the underlying sodium channel dysfunction predisposes to seizures early in life accompanied by neuronal injury that evokes pathological structural changes (e.g. mossy fiber sprouting) and chronically reduced seizure threshold (McCormick, D. A. & Contreras, D., 2001).

Epileptogenesis in GEFS+ could therefore be preventable by early pharmacological interventions that specifically target the underlying sodium channel dysfunction.

Methods Employed in Examples

Molecular cloning of human SCN1A cDNA. The human SCN1A open-reading frame (ORF) was predicted by comparing the orthologous rat coding sequence (NCBI accession number $NM_{13}030875$) to human genomic sequence using the program BLASTN, publicly available through the National Center for Biotechnology Information website. Twenty-six exons were identified, ordered and assembled into a 6030 bp ORF and 873 bp 3'-untranslated region (3'-UTR). Based on this prediction, four sets of PCR primers (AF: 5' - GTTTCTTGCGGCCGCATGGAGCAAA-CAGTGCTTGTACCA - 3', AR: 5' - GTGTCTTTCCCT-TCAATGGAGAAGCGA - 3', BF: 5' - GTTTCTTCTG-GTGGGGAAGAGAAAG - 3', BR: 5' - GTGTCTTCTATACCACTTGTAGTTCCATTTA - 3', CF: 5' - GTTTCTTTATGTCCAATCATACAGCAGA - 3', CR: 5' - GTGTCTTGGCTTACTGTTGAGAATGGG - 3', DF: 5' - GTTTCTTACGCCATTATTATTTTACCA - 3', DR: 5' - GTGTCTTGTCGACTCAAGGTCATCTCCCCTTTA - 3') (SEQ ID NOS 10–17, respectively) were designed to generate overlapping SCN1A cDNAs. Human cerebral cortex cDNA (Clontech, Palo Alto, Calif., United States of America) was used as template during hot start PCR performed in 50 µl reactions at 94° C. for 5 minutes (min) followed by 35 cycles of 94° C. for 1 min, 51–57° C. for 1 min, and 72° C. for 3–4 min and a final cycle at 72° C. for 5 min. Some reactions required the addition of 10% (v/v) Q solution (Qiagen, Valencia, Calif., United States of America). To enhance amplification fidelity, all reactions were performed using a combination of Taq and Pwol (20% v/v; Roche, Indiapolis, United States of America) polymerases.

Reaction products were gel extracted then cloned into pCR2.1-TOPO (Invitrogen, Carlsbad, Calif., United States of America), and selectively grown in TOP10 INVaF' (Invitrogen) or STBL2 cells (Life Technologies, Grand Island, N.Y., United States of America). Plasmid DNA was isolated with standard techniques, confirmed by restriction fingerprinting and sequenced using automated fluorescent dye terminator chemistry. Polymerase errors were repaired by site-directed mutagenesis or by subcloning fragments from other clones. A full-length cDNA was assembled in the mammalian expression vector pCMV-Script (Stratagene, La Jolla, Calif., United States of America) and re-sequenced completely. A short poly-T region exhibiting a high spontaneous mutation rate in the full-length construct was interrupted by the introduction of two silent T to C mutations at ORF positions 1206 and 1209. All full-length constructs were propagated in STBL2 cells grown at 30° C. for >48 hours.

Mutagenesis. SCN1A mutants T875M, W1204R, and R1648H were named according to the single letter code indicating the amino acid exchange and its position with respect to the starting methionine. Mutants were generated by PCR based site-directed mutagenesis. Successful introduction of the mutations was monitored by digestion at engineered silent restriction sites and all mutant cDNAs were re-sequenced fully before use in experiments.

Cell Culture and Transfection. Human tsA201 cells, a HEK-293 derivative stably transfected with the SV40 large T antigen, were grown in Dulbecco's modified Eagle medium (DMEM) supplemented with 10% fetal bovine serum (FBS, ATLANTA Biologicals, Norcross, Ga., United States of America), 2 mM L-glutamine, and penicillin (50 units/ml)-streptomycin (50 μg/ml) in a humidified 5% CO2 atmosphere at 37° C. Only cells from passage ≦3 were used.

Expression of SCN1A, β1 and β2 was achieved by transient plasmid transfection using the Qiagen SUPERFECT® reagent. Approximately 6 μg of total DNA was transfected in a plasmid mass ratio of a :β1:β2=10:1:1. The human voltage-gated sodium channel auxiliary subunits hβ1 and hβ2 were cloned into plasmids (Clontech, Palo Alto, Calif., United States of America) containing the marker genes CD8 (pCD8-IRES-hβ1) or GFP (pGFP-IRES-hβ2) along with an internal ribosome entry site. Cells were passaged 24 hours after transfection and incubated 24 hours before their use in electrophysiology experiments. Transfected cells were dissociated by brief exposure to trypsin/EDTA, resuspended in supplemented DMEM medium, and allowed to recover for about 30 min at 37° C. in 5% $CO_2$. CD8 antibody-covered microbeads (DYNABEADS® M-450 CD8, Dynal, Norway) suspended in 200 μl DMEM were added to the cell suspension and gently shaken. In order to allow for patch-excision in single-channel studies, tsA201 cells were plated on glass coverslips and pre-treated with CELLTAK® cell adhesive (Collaborative Biomedical Products, Bedford, Mass., United States of America). Only cells positive for CD8 antigen and GFP fluorescence were used for electrophysiological studies. Non-transfected cells were used as negative controls.

Electrophysiology and data analysis. Dissociated cells were placed into a recording chamber on the stage of an inverted microscope with epifluorescence capability. After allowing the cells to settle for 10 minutes, sodium currents were recorded in the whole-cell and excised, outside-out patch configurations of the patch-clamp technique (Hamill, O. P. et al., *Pflügers Arch* 391:85–100 (1981)) using AXOPATCH™ 200A and 200B amplifiers (Axon Instruments Inc., Union City, Calif., United States of America). Bath solution (containing in mM: NaCl 145, KCl 4, $CaCl_2$ 1.8, $MgCl_2$ 1, HEPES 10, pH 7.35, 310 mOsmol/kg) was continuously exchanged by a gravity-driven perfusion system. The pipette solution (in mM: NaF 10, CsF 110, CsCl 20, EGTA 2, HEPES 10, pH 7.35, 310 mOsmol/kg) was matched in pH and osmolality to the bath solution. Patch pipettes were pulled from borosilicate glass (World Precision Instruments, Inc., Sarasota, Fla., United States of America) with a multistage P-97 Flaming-Brown micropipette puller (Sutter Instruments Co., San Rafael, Calif., United States of America) and fire-polished (Micro Forge MF 830, Naras hige, Japan). Patch pipettes for single-channel studies were coated with SYLGARD™ 184 (Dow Corning Corp., Midland, Mich., United States of America).

Pipette resistance was 0.8–1.5 MΩ for whole-cell and about 4 MΩ for single-channel experiments. Cells were allowed to stabilize for 10 minutes after establishment of the whole-cell configuration before currents were measured. Recordings from cells exhibiting peak current amplitudes less than 0.8 nA were excluded from analysis to avoid the potential for endogenous channel contamination. Cells exhibiting very large whole-cell currents were also excluded if voltage control was compromised. Whole-cell capacitance was assessed by integrating the capitative transient elicited by a 10 mV voltage step from −120 mV to −110 mV with 10 kHz filtering. As a reference electrode, a 2% agar-bridge with composition similar to the bath solution was utilized. Whole-cell currents were acquired at 20–50 kHz and filtered at 5 kHz. Single-channel current traces were acquired at 10 kHz and filtered at 1 kHz.

Channel behavior was examined over a range of test potentials (see figure insets for pulse protocols). Each voltage step was followed by a 5-second pulse at −120 mV. Pulse generation, data collection and analyses were done with CLAMPEX™ 7.0 (Axon Instruments, Inc.), EXCEL™ 97 (Microsoft, Seattle, Wash., United States of America), Origin 6.0 (MICROCAL™, Northampton, Mass., United States of America), and SIGMA PLOT™ 2000 (SPSS Science, Chicago, Ill., United States of America) software. Current-voltage relationships were constructed by plotting the peak current against the test potential.

Steady-state inactivation was analyzed by a two-pulse protocol, where the peak current measured during the test pulse was normalized to the prepulse peak current and plotted as open probability vs prepulse potential. Data were fitted to a two-state Boltzmann equation:

$$f(x) = \frac{1-C}{e^{(x-V_{1/2})/k}} + C,$$

where $V_{1/2}$ is the voltage where 50% of the channels are inactivated, k is the slope factor of inactivation, and C is the steady-state asymptote.

Time constants (τ) of inactivation were derived from the current decay fitted to a single or a double exponential function:

$$f(t) = \sum_{i=1}^{n} A_i \cdot e^{-(t-K)/\tau_i} + C,$$

where t is the time, A is the fraction of channels inactivating with time constant τi ($\tau_f$ and $\tau_s$ represent fast and slow time constants, respectively), and K is the manually selected point of onset of exponential macroscopic current decay.

Voltage dependence of activation data was derived from calculating the conductances seen in current/voltage relationship recordings using the formula:

$$G(V) = \frac{I(V)}{V - E_{rev}},$$

where I(V) is the peak raw current at the damping potential V, and $E_{rev}$ is the estimated reversal potential.

Conductances were normalized to the maximal conductance between −80 and +20 mV and fitted to the two-state Boltzmann equation:

$$f(x) = \frac{-1}{e^{(x-V_{1/2})/k}} + 1,$$

where $V_{1/2}$ is the voltage at which half-maximal activation occurs and k describes the slope of the fit.

Recovery from inactivation was also examined by a two-pulse protocol. The peak current amplitude during the test pulse was plotted as fractional recovery against the recovery period by normalizing to the maximum current during the conditioning, followed by fitting to a single or a double exponential function:

$$f(t) = \sum_{i=1}^{n} A_i (1 - e^{-t/\tau_i}),$$

where t is time, and $A_i$ describes the fraction of channels recovering with $\tau_i$ ($\tau_f$ and $\tau_s$ represent fast and slow time constants, respectively).

All experiments were performed a room temperature. Data are shown as means ± S.E.M with the number of experiments provided as n in the figure legends. Statistical comparisons were done with the Student's t-test and differences were considered significant at the $p<0.05$ level (denoted in the figures by *).

REFERENCES

The references listed below as well as all references cited in the specification are incorporated herein by reference to the extent that they supplement, explain, provide a background for or teach methodology, techniques and/or compositions employed herein.

Abou-Khalil, B. et al. Partial epilepsy and generalized epilepsy with febrile seizures plus and a novel SCN1A mutation. Neurology 57, 2265–2272. 2001.

Abdul M & Hoosein N (2001) Inhibition by anticonvulsants of prostate-specific antigen and interleukin-6 secretion by human prostate cancer cells. Anticancer Res 21:2045–2048.

Abruzzese R V, Godin D, Burcin M, Mehta V, French M, Li Y, O'Malley B W & Nordstrom J L (1999) Ligand-dependent regulation of plasmid-based transgene expression in vivo. Hum Gene Ther 10:1499–1507.

Alekov A, Rahman M M, Mitrovic N, Lehmann-Horn F & Lerche H (2000) A sodium channel mutation causing epilepsy in man exhibits subtle defects in fast inactivation and activation in vitro. J Physiol (London) 529 Pt 3:533–539.

Alekov A K, Rahman M M, Mitrovic N. Lehmann-Horn F & Lerche H (2001) Enhanced inactivation and acceleration of activation of the sodium channel associated with epilepsy in man. Eur J Neurosci 13:2171–2176.

Altschul S F, Gish W, Miller W. Myers E W & Lipman D J (1990) Basic local alignment search tool. J Mol Biol 215:403–410.

Ausubel F, ed (1995) Short Protocols in Molecular Biology, 3rd ed. Wiley, N.Y.

Barton G J (1998) Protein sequence alignment techniques. Acta Crystallogr D Biol Crystallogr 54:1139–1146.

Batzer M A, Carlton J E & Deininger P L (1991) Enhanced evolutionary PCR using oligonucleotides with inosine at the 3'-terminus. Nucleic Acids Res 19:5081.

Bauminger S & Wilchek M (1980) The use of carbodiimides in the preparation of immunizing conjugates. Methods Enzymol 70:151–159.

Bennett, P. B., Yazawa, K., Makita N. & George, A. L., Jr. Molecular mechanism for an inherited cardiac arrhythmia. Nature 376, 683–685 (1995).

Berkow R, Beers M H & Fletcher A J (1997) The Merck Manual of Medical Information, Home ed. Merck Research Laboratories, Whitehouse Station, N.J.

Blundell T L & Johnson L N (1976) Protein Crystallography. Academic Press, New York.

Bodanszky M (1993) Principles of Peptide Synthesis, 2nd rev. ed. Springer-Verlag, Berlin; New York.

Burcin M M, Schiedner G, Kochanek S, Tsai S Y & O'Malley B W (1999) Adenovirus-mediated regulable target gene expression in vivo. Proc Natl Acad Sci U S A 96:355–360.

Cannon, S. C. Spectrum of sodium channel disturbances in the nondystrophic myotonias and periodic paralyses. Kidney Int. 57, 772–779 (2000).

Cannon, S. C., Brown, R. H., Jr. & Corey, D. P. Theoretical reconstruction of myotonia and paralysis caused by incomplete inactivation of sodium channels. Biophys J 65, 270–288 (1993).

Caron J & Libersa C (1997) Adverse effects of class I antiarrhythmic drugs. Drug Saf 17:8–36.

Catterall, W. A. Cellular and molecular biology of voltage-gated sodium channels. Physiologic Rev 72, S15–S48 (1992))

Catterall W A, Morrow C S, Daly J W & Brown G B (1981) Binding of batrachotoxinin A 20-alpha-benzoate to a receptor site associated with sodium channels in synaptic nerve ending particles. J Biol Chem 256:8922–8927.

Chan D W (1996) Immunoassay Automation: A Practical Guide. Academic Press, San Diego.

Chang L T (1983) A method for attenuation correction in radionuclide computed tomography. IEEE Trans Nucl Sci NS-25:638–643.

Chen H, McCarty D M, Bruce A T & Suzuki K (1998) Gene transfer and expression in oligodendrocytes under the control of myelin basic protein transcriptional control region mediated by adeno-associated virus. Gene Ther 5:50–58.

Chen H, McCarty D M, Bruce A T & Suzuki K (1999) Oligodendrocyte-specific gene expression in mouse brain: use of a myelin-forming cell type-specific promoter in an adeno-associated virus. J Neurosci Res 55:504–513.

Chiang L W (1998) Detection of gene expression in single neurons by patch-clamp and single-cell reverse transcriptase polymerase chain reaction. J Chromatogr A 806:209–218.

Claes L, Del-Favero J, Ceulemans B, Lagae L, Van Broeckhoven C & De Jonghe P (2001) De novo mutations in the sodium-channel gene SCN1A cause severe myoclonic epilepsy of infancy. Am J Hum Genet 68:1327–1332.

Coulter D A (1997) Antiepileptic drug cellular mechanisms of action: where does lamotrigine fit in? J Child Neurol 12 Suppl 1:S2–9.

D'Arcangelo G. Paradiso K, Shepherd D, Brehm P, Halegoua S & Mandel G (1993) Neuronal growth factor regulation of two different sodium channel types through distinct signal transduction pathways. J Cell Biol 122: 915–921.

Deisenhofer J, Epp O, Miki K. Huber R & Michel H (1984) X-ray structure analysis of a membrane protein complex. Electron density map at 3 A resolution and a model of the chromophores of the photosynthetic reaction center from Rhodopseudomonas viridis. J Mol Biol 180:385–398.

Deuschle U, Meyer W K & Thiesen H J (1995) Tetracycline-reversible silencing of eukaryotic promoters. *Mol Cell Biol* 15:1907–1914.

Dhillon H, Minter R, Topping D, Prima V, Moldawer L & Muzyczka N (1999) Long-term correction of obesity using centrally delivered rAAV encoding anorexigenic cytokines. *Am Soc Gene Ther Abstr* 2:45a.

Diss J K, Archer S N, Hirano J, Fraser S P & Djamgoz M B (2001) Expression profiles of voltage-gated Na(+) channel alpha-subunit genes in rat and human prostate cancer cell lines. *Prostate* 48:165–178.

Duch D S, Rehberg B & Vysotskaya T N (1998) Volatile anesthetics significantly suppress central and peripheral mammalian sodium channels. *Toxicol Lett* 100–101:255–263.

Dupere J R, Dale T J, Starkey S J & Xie X (1999) The anticonvulsant BW534U87 depresses epileptiform activity in rat hippocampal slices by an adenosine-dependent mechanism and through inhibition of voltage-gated Na+ channels. *Br J Pharmacol* 128:1011–1020.

Ebadi M S (1998) *CRC Desk Reference of Clinical Pharmacology.* CRC Press, Boca Raton.

Eglen R M, Hunter J C & Dray A (1999) Ions in the fire: recent ion-channel research and approaches to pain therapy. *Trends Pharmacol Sci* 20:337–342.

Elmer L W, O'Brien B J, Nutter T J & Angelides K J (1985) Physicochemical characterization of the alpha-peptide of the sodium channel from rat brain. *Biochemistry* 24:8128–8137.

Escayg A, Heils A, MacDonald B T, Haug K, Sander T & Meisler M H (2001) A novel SCN1A mutation associated with generalized epilepsy with febrile seizures plus—and prevalence of variants in patients with epilepsy. *Am J Hum Genet* 68:866–873.

Escayg A, MacDonald B T, Meisler M H, Baulac S, Huberfeld G, An-Gourfinkel I, Brice A, LeGuern E, Moulard B. Chaigne D, Buresi C & Malafosse A (2000) Mutations of SCN1A, encoding a neuronal sodium channel, in two families with GEFS+2. *Nat Genet* 24:343–345.

European Patent No. 0 439 095

Forss-Petter S, Danielson P E, Catsicas S, Battenberg E, Price J, Nerenberg M & Sutcliffe J G (1990) Transgenic mice expressing beta-galactosidase in mature neurons under neuron-specific enolase promoter control. *Neuron* 5:187–197.

Freireich E J, Gehan E A, Rail D P, Schmidt L H & Skipper H E (1966) Quantitative comparison of toxicity of anticancer agents in mouse, rat, hamster, dog, monkey, and man. *Cancer Chemother Rep* 50:219–244.

Freshney R I (1987) *Culture of Animal Cells: A Manual of Basic Technique,* 2nd ed. A. R. Liss, New York.

Games D, Adams D, Alessandrini R, Barbour R, Berthelette P, Blackwell C, Carr T, Clemens J, Donaldson T, Gillespie F & et al. (1995) Alzheimer-type neuropathology in transgenic mice overexpressing V717F beta-amyloid precursor protein. *Nature* 373:523–527.

Gerner E W, Hersh E M, Pennington M, Tsang T C, Harris D, Vasanwala F & Brailey J (2000) Heat-inducible vectors for use in gene therapy. *Int J Hyperthermia* 16:171–181.

Glover D M & Hames B D (1995) *DNA Cloning: A Practical Approach,* 2nd ed. IRL Press at Oxford University Press, Oxford/New York.

Gold M S (1999) Tetrodotoxin-resistant Na+ currents and inflammatory hyperalgesia. *Proc Natl Acad Sci U S A* 96:7645–7649.

Goldman C K, Rogers B E, Douglas J T, Sosnowski B A, Ying W, Siegal G P, Baird A, Campain J A & Curiel D T (1997) Targeted gene delivery to Kaposi's sarcoma cells via the fibroblast growth factor receptor. *Cancer Res* 57:1447–1451.

Goodman L S, Gilman A, Hardman J G, Gilman A G & Limbird L E (1996) *Goodman & Gilman's the Pharmacological Basis of Therapeutics,* 9th ed. McGraw-Hill Health Professions Division, New York.

Gossen M, Freundlieb S, Bender G, Muller G, Hillen W & Bujard H (1995) Transcriptional activation by tetracyclines in mammalian cells. *Science* 268:1766–1769.

Henikoff J G, Pietrokovski S, McCallum C M & Henikoff S (2000) Blocks-based methods for detecting protein homology. *Electrophoresis* 21:1700–1706.

Henikoff S & Henikoff J G (1992) Amino acid substitution matrices from protein blocks. *Proc Natl Acad Sci U S A* 89:10915–10919.

Hickenbottom S L & Grotta J (1998) Neuroprotective therapy. *Semin Neurol* 18:485–492.

Homola J, Yee S & Gauglitz G (1999) Surface plasmon resnoance sensors: review. *Sensors and Actuators* 54:3–15.

Huang C C, Novak W R, Babbitt P C, Jewett A I, Ferrin T E & Klein T E (2000) Integrated tools for structural and sequence alignment and analysis. *Pac Symp Biocomput:* 230–241.

Hutchens & Yip (1993) *Rapid Communications in Mass Spectroscopy* 7:576–580.

Ikenaka K & Kagawa T (1995) Transgenic systems in studying myelin gene expression. *Dev Neurosci* 17:127–136.

Ishikawa E (1999) *Ultrasensitive and rapid enzyme immunoassay.* Elsevier, Amsterdam/New York.

Isom L L, De Jongh K S, Patton D E, Reber B F, Offord J, Charbonneau H, Walsh K, Goldin A L & Catterall W A (1992) Primary structure and functional expression of the beta 1 subunit of the rat brain sodium channel. *Science* 256:839–842.

Jellett J F, Marks L J, Stewart J E, Dorey M L, Watson-Wright W & Lawrence J F (1992) Paralytic shellfish poison (saxitoxin family) bioassays: automated endpoint determination and standardization of the in vitro tissue culture bioassay, and comparison with the standard mouse bioassay. *Toxicon* 30:1143–1156.

Ji H L, Fuller C M & Benos D J (1999) Peptide inhibition of constitutively activated epithelial Na(+) channels expressed in *Xenopus oocytes. J Biol Chem* 274:37693–37704.

Karlin S & Altschul S F (1993) Applications and statistics for multiple high-scoring segments in molecular sequences. *Proc Natl Acad Sci U S A* 90:5873–5877.

Katzung B G (2001) *Basic & Clinical Pharmacology,* 8th ed. Lange Medical Books/McGraw-Hill Medical Pub. Division, New York.

Klein R L, Meyer E M, Peel A L, Zolotukhin S, Meyers C, Muzyczka N & King M A (1998) Neuron-specific transduction in the rat septohippocampal or nigrostriatal pathway by recombinant adeno-associated virus vectors. *Exp Neurol* 150:183–194.

Kogure K, Tamplin M L, Simidu U & Colwell R R (1988) A tissue culture assay for tetrodotoxin, saxitoxin and related toxins. *Toxicon* 26:191–197.

Kyte J & Doolittle R F (1982) A simple method for displaying the hydropathic character of a protein. *J Mol Biol* 157:105–132.

Law B (1996) *Immunoassay: A Practical Guide.* Taylor & Francis, London/Bristol, Pennsylvania.

Lehmann-Horn F & Jurkat-Roff K (1999) Voltage-gated ion channels and hereditary disease. *Physiol Rev* 79:1317–1372.

Liddell E & Weeks I (1995) Antibody Technology. Bios Scientific Publishers, Oxford, United Kingdom.

Liedberg B, Nylander C & Lundstrom I (1983) Surface plasmon resonance for gas detection and biosensing. *Sensors and Actuators* 4:299–304.

Maalouf G J, Xu W, Smith T F & Mohr S C (1998) Homology model for the ligand-binding domain of the human estrogen receptor. *J Biomol Struct Dyn* 15:841–851.

Madio D P, van Gelderen P, DesPres D, Olson A W, de Zwart J A, Fawcett T W, Holbrook N J, Mandel M & Moonen C T (1998) On the feasibility of MRI-guided focused ultrasound for local induction of gene expression. *J Magn Reson Imaging* 8:101–104.

Magde D, Elsen E & Webb W (1972) Thermodynamic fluctuations in a reacting system: measurement by fluorescence correlation spectroscopy. *Physical Review Letters* 29:705–708.

Maiti S, Haupts U & Webb W W (1997) Fluorescence correlation spectroscopy: diagnostics for sparse molecules. *Proc Natl Acad Sci U S A* 94:11753–11757.

Mak P, McDonnell D P, Weigel N L, Schrader W T & O'Malley B W (1989) Expression of functional chicken oviduct progesterone receptors in yeast (*Saccharomyces cerevisiae*). *J Biol Chem* 264:21613–21618.

Mandel R J, Rendahl K G, Spratt S K, Snyder R O, Cohen L K & Leff S E (1998) Characterization of intrastriatal recombinant adeno-associated virus-mediated gene transfer of human tyrosine hydroxylase and human GTP-cyclohydrolase I in a rat model of Parkinson's disease. *J Neurosci* 18:4271–4284.

Manson M M (1992) *Immunochemical Protocols*. Humana Press, Totowa, N.J.

Masseyeff R F. Albert W H W & Staines N (1993) *Methods of Immunological analysis*. VCH Verlagsgesellschaft/ VCH Publishers, Weinheim, Federal Republic of Germany/New York.

McCleskey E W & Gold M S (1999) Ion channels of nociception. *Annu Rev Physiol* 61:835–856.

McPherson (1982) *The Preparation and Analysis of Protein Crystals*. John Wiley, New York.

Mitchell P H & Habermann B (1999) Rethinking physiologic stability: touch and intracranial pressure. *Biol Res Nurs* 1:12–19.

Morgan K, Stevens E B, Shah B, Cox P J, Dixon A K, Lee K, Pinnock R D, Hughes J, Richardson P J, Mizuguchi K & Jackson A P (2000) beta 3: an additional auxiliary subunit of the voltage-sensitive sodium channel that modulates channel gating with distinct kinetics. *Proc Natl Acad Sci U S A* 97:2308–2313.

Nabel G (1997) Vectors for Gene Therapy. In: *Current Protocols in Human Genetics*. John Wiley & Sons, New York.

Needleman S B & Wunsch C D (1970) A general method applicable to the search for similarities in the amino acid sequence of two proteins. *J Mol Biol* 48:443–453.

Neri D, Carnemolla B, Nissim A, Leprini A, Querze G, Balza E, Pini A, Tarli L, Halin C, Neri P, Zardi L & Winter G (1997) Targeting by affinity-matured recombinant antibody fragments of an angiogenesis associated fibronectin isoform. *Nat Biotechnol* 15:1271–1275.

Niwa H, Yamamura K & Miyazaki J (1991) Efficient selection for high-expression transfectants with a novel eukaryotic vector. *Gene* 108:193–199.

No D, Yao T P & Evans R M (1996) Ecdysone-inducible gene expression in mammalian cells and transgenic mice. *Proc Natl Acad Sci U S A* 93:3346–3351.

Ohtsuka E, Matsuki S, Ikehara M, Takahashi Y & Matsubara K (1985) An alternative approach to deoxyoligonucleotides as hybridization probes by insertion of deoxyinosine at ambiguous codon positions. *J Biol Chem* 260:2605–2608.

Oiki S, Madison V & Montal M (1990) Bundles of amphipathic transmembrane alpha-helices as a structural motif for ion-conducting channel proteins: studies on sodium channels and acetylcholine receptors. *Proteins* 8:226–236.

Oxender D L & Fox C F (1987) *Protein Enqineering*. Liss, New York.

Park J W, Hong K, Kirpotin D B, Papahadjopoulos D & Benz C C (1997) Immunoliposomes for cancer treatment. *Adv Pharmacol* 40:399–435.

Pasqualini R, Koivunen E & Ruoslahti E (1997) Alpha v integrins as receptors for tumor targeting by circulating ligands. *Nat Biotechnol* 15:542–546.

Pearson W R & Lipman D J (1988) Improved tools for biological sequence comparison. *Proc Natl Acad Sci U S A* 85:2444–2448.

Peel A L, Zolotukhin S, Schrimsher G W, Muzyczka N & Reier P J (1997) Efficient transduction of green fluorescent protein in spinal cord neurons using adeno-associated virus vectors containing cell type-specific promoters. *Gene Ther* 4:16–24.

Porreca F, Lai J, Bian D, Wegert S, Ossipov M H, Eglen R M, Kassotakis L, Novakovic S, Rabert D K, Sangameswaran L & Hunter J C (1999) A comparison of the potential role of the tetrodotoxin-insensitive sodium channels, PN3/SNS and NaN/SNS2, in rat models of chronic pain. *Proc Natl Acad Sci U S A* 96:7640–7644.

Reith M E (1990) [14C]guanidinium ion influx into Na+ channel preparations from mouse cerebral cortex. *Eur J Pharmacol* 188:33–41.

Remington J P, Osol A, Anderson J T, Hoover J E & Skolaut M W (1975) *Remington's Pharmaceutical Sciences*, 15th ed. Mack Pub. Co., Easton, Pa.

Rossolini G M, Cresti S, Ingianni A, Cattani P, Riccio M L & Satta G (1994) Use of deoxyinosine-containing primers vs degenerate primers for polymerase chain reaction based on ambiguous sequence information. *Mol Cell Probes* 8:91–98.

Sabirov R Z, Azimov R R, Ando-Akatsuka Y, Miyoshi T & Okada Y (1999) Na(+) sensitivity of ROMK1 K(+) channel: role of the Na(+)/H(+) antiporter. *J Membr Biol* 172:67–76.

Sambrook et al. eds (1989) *Molecular Cloning: A Laboratory Manual*. Cold Spring Harbor Laboratory Press, Cold Spring Harbor.

Saqi M A, Wild D L & Hartshorn M J (1999) Protein analyst—a distributed object environment for protein sequence and structure analysis. *Bioinformatics* 15:521–522.

Schneider C H & Eberle A N (1993) *Peptides. 1992: Proceedings of the Twenty-Second European Peptide Symposium*, Sep. 13–19, 1992. Interlaken, Switzerland. Escom, Leiden.

Schröder E & Lübke K (1965) *The Peptides*. Academic Press, New York.

Silhavy T J, Berman M L, Enquist L W & Cold Spring Harbor Laboratory. (1984) *Experiments with Gene Fusions*. Cold Spring Harbor Laboratory, Cold Spring Harbor, N.Y.

Sindrup S H & Jensen T S (2000) Pharmacologic treatment of pain in polyneuropathy. *Neurology* 55:915–920.

Smith M R, Smith R D, Plummer N W, Meisler M H & Goldin A L (1998) Functional analysis of the mouse Scn8a sodium channel. *J Neurosci* 18:6093–6102.

Smith R D & Goldin A L (1998) Functional analysis of the rat I sodium channel in *Xenopus oocytes*. *J Neurosci* 18:811–820.

Smith T F & Waterman M (1981) Comparison of Biosequences. *Adv Appl Math* 2:482–489.

Spampanato, J., Escayg, A., Meisler, M. H., and Goldin, A. L. (2001). Functional effects of two voltage-gated sodium channel mutations that cause generalized epilepsy with febrile seizures plus type 2. J. Neurosci. 21, 7481–7490.

Speight T M, Holford N H G & Avery G S (1997) *Avery's Drug Treatment: A Guide to the Properties, Choice, Therapeutic Use and Economic Value of Drugs in Disease Management,* 4th ed. Adis International, Auckland/Philadelphia.

Squire I B, Lees K R, Pryse-Phillips W, Kertesz A & Bamford J (1995) Efficacy and tolerability of lifarizine in acute ischemic stroke. A pilot study. Lifarizine Study Group. *Ann N Y Acad Sci* 765:317–318.

Stoll J & Galdzicki Z (1996) Reduced expression of voltage-gated sodium channels in neurons cultured from trisomy 16 mouse hippocampus. *Int J Dev Neurosci* 14:749–760.

Stuhmer W, Methfessel C, Sakmann B, Noda M & Numa S (1987) Patch clamp characterization of sodium channels expressed from rat brain cDNA. *Eur Biophys J* 14:131–138.

Taglialatela M, Toro L & Stefani E (1992) Novel voltage clamp to record small, fast currents from ion channels expressed in *Xenopus oocytes*. *Biophys J* 61:78–82.

Tijssen (1993) *Laboratory Techniques in Biochemistry and Molecular Biology-Hybridization with Nucleic Acid Probes.* Elsevier, N.Y.

U.S. Pat. No. 4,196,265
U.S. Pat. No. 4,455,842
U.S. Pat. No. 4,551,482
U.S. Pat. No. 4,554,101
U.S. Pat. No. 4,946,778
U.S. Pat. No. 5,091,513
U.S. Pat. No. 5,132,405
U.S. Pat. No. 5,223,409
U.S. Pat. No. 5,234,933
U.S. Pat. No. 5,260,203
U.S. Pat. No. 5,264,563
U.S. Pat. No. 5,326,902
U.S. Pat. No. 5,490,840
U.S. Pat. No. 5,498,538
U.S. Pat. No. 5,499,971
U.S. Pat. No. 5,510,103
U.S. Pat. No. 5,574,172
U.S. Pat. No. 5,629,145
U.S. Pat. No. 5,650,489
U.S. Pat. No. 5,651,991
U.S. Pat. No. 5,677,427
U.S. Pat. No. 5,667,988
U.S. Pat. No. 5,688,931
U.S. Pat. No. 5,690,954
U.S. Pat. No. 5,702,892
U.S. Pat. No. 5,707,798
U.S. Pat. No. 5,714,166
U.S. Pat. No. 5,738,996
U.S. Pat. No. 5,747,334
U.S. Pat. No. 5,756,291
U.S. Pat. No. 5,762,918
U.S. Pat. No. 5,762,909
U.S. Pat. No. 5,786,387
U.S. Pat. No. 5,780,225
U.S. Pat. No. 5,824,483
U.S. Pat. No. 5,834,228
U.S. Pat. No. 5,840,479
U.S. Pat. No. 5,855,900
U.S. Pat. No. 5,858,410
U.S. Pat. No. 5,858,670
U.S. Pat. No. 5,871,778
U.S. Pat. No. 5,872,011
U.S. Pat. No. 5,892,019
U.S. Pat. No. 5,912,132
U.S. Pat. No. 5,922,254
U.S. Pat. No. 5,922,545
U.S. Pat. No. 5,922,356
U.S. Pat. No. 5,948,635
U.S. Pat. No. 5,962,667
U.S. Pat. No. 5,985,279
U.S. Pat. No. 5,994,392
U.S. Pat. No. 6,001,088
U.S. Pat. No. 6,041,253
U.S. Pat. No. 6,054,561
U.S. Pat. No. 6,057,098
U.S. Pat. No. 6,068,829
U.S. Pat. No. 6,071,890
U.S. Pat. No. 6,106,866
U.S. Pat. No. 6,107,059
U.S. Pat. No. 6,127,339
U.S. Pat. No. 6,140,123
U.S. Pat. No. 6,156,511
U.S. Pat. No. 6,165,440
U.S. Pat. No. 6,168,912
U.S. Pat. No. 6,174,708
U.S. Pat. No. 6,174,690
U.S. Pat. No. 6,176,089
U.S. Pat. No. 6,177,088
U.S. Pat. No. 6,180,082
U.S. Pat. No. 6,180,348
U.S. Pat. No. 6,207,195
U.S. Pat. No. 6,214,553
U.S. Pat. No. 6,232,287
U.S. Pat. No. 6,234,990
U.S. Pat. No. 6,261,831

Vekris A, Maurange C, Moonen C, Mazurier F, De Verneuil H, Canioni P & Voisin P (2000) Control of transgene expression using local hyperthermia in combination with a heat-sensitive promoter. *J Gene Med* 2:89–96.

Walker M R & Rapley R (1993) *Molecular and Antibody Probes in Diagnosis.* Wiley, Chichester, N.Y.

Wallace R H, Wang D W, Singh R, Scheffer I E, George A L, Jr., Phillips H A, Saar K, Reis A, Johnson E W, Sutherland G R, Berkovic S F & Mulley J C (1998) Febrile seizures and generalized epilepsy associated with a mutation in the Na+-channel beta1 subunit gene SCN1B. *Nat Genet* 19:366–370.

Waxman S G, Dib-Hajj S, Cummins T R & Black J A (1999a) Sodium channels and pain. *Proc Natl Acad Sci U S A* 96:7635–7639.

Waxman S G, Cummins T R, Dib-Hajj S D & Black J A (2000) Voltage-gated sodium channels and the molecular pathogenesis of pain: a review. *J Rehabil Res Dev* 37:517–528.

Waxman S G, Cummins T R, Dib-Hajj S, Fjell J & Black J A (1999b) Sodium channels, excitability of primary sensory neurons, and the molecular basis of pain. *Muscle Nerve* 22:1177–1187.

Weichselbaum R R, Hallahan D, Fuks Z & Kufe D (1994) Radiation induction of immediate early genes: effectors of the radiation-stress response. *Int J Radiat Oncol Biol Phys* 30:229–234.

Weichselbaum R R, Hallahan D E, Sukhatme V, Dritschilo A, Sherman M L & Kufe D W (1991) Biological consequences of gene regulation after ionizing radiation exposure. *J Natl Cancer Inst* 83:480–484.

Weiss M S, Wacker T, Weckesser J, Welte W & Schulz G E (1990) The three-dimensional structure of porin from *Rhodobacter capsulatus* at 3 A resolution. *FEBS Lett* 267:268–272.

WO 93/25521

WO 99/26966

Worrall T A, Cotter R J & Woods A S (1998) Purification of contaminated peptides and proteins on synthetic membrane surfaces for matrix-assisted laser desorption/ionization mass spectrometry. *Anal Chem* 70:750–756.

Wyckoff H W, Hirs C H W & Timasheff S N (1985) *Diffraction Methods for Biological Macromolecules.* Academic Press, Orlando, Fla.

Yamashita M, Ikemoto Y, Nielsen M & Yano T (1999) Effects of isoflurane and hexafluorodiethyl ether on human recombinant GABA(A) receptors expressed in Sf9 cells. *Eur J Pharmacol* 378:223–231.

Dudek, F. E., Yasumura, T. & Rash, J. E. 'Non-synaptic' mechanisms in seizures and epileptogenesis. *Cell Biol Int.* 22, 793–805 (1998).

Hamill, O. P., Marty, A., Neher, E., Sakmann, B. & Sigworth, F. J. Improved patchclamptechniques for high-resolution current recording from cells and cell-free membrane patches. *Pflügers Arch* 391, 85–100 (1981).

Jefferys, J. G. Nonsynaptic modulation of neuronal activity in the brain: electric currents and extracellular ions. *Physiol Rev.* 75, 689–723 (1995).

McCormick, D. A. & Contreras, D. On the cellular and network bases of epileptic seizures. *Annu. Rev. Physiol* 63, 815–846 (2001).

Reckziegel, G., Beck, H., Schramm, J., Elger, C. E. & Urban, B. W. Electrophysiological characterization of Na+ currents in acutely isolated human hippocampal dentate granule cells. *J Physiol* (London) 509 (Pt 1), 139–150 (1998).

Sah, D. W. Human fetal central neurons in culture: vol. *J Neurophysiol.* 74, 1889–1899 (1995).

Scheffer, I. E. & Berkovic, S. F. Generalized epilepsy with febrile seizures plus. A genetic disorder with heterogeneous clinical phenotypes. *Brain* 120 (Pt 3), 479–490 (1997).

Shin, C. & McNamara, J. O. Mechanism of epilepsy. *Annu. Rev. Med* 45, 379–389 (1994)

Singh, R., Scheffer, I. E., Crossland, K. & Berkovic, S. F. Generalized epilepsy with febrile seizures plus: a common childhood-onset genetic epilepsy syndrome. *Ann. Neurol.* 45, 75–81 (1999).

Spampanato, J., Escayg, A., Meisler, M. H. & Goldin, A. L. Functional effects of two voltage-gated sodium channel mutations that cause generalized epilepsy with febrile seizures plus type 2. *J Neurosci* 21, 7481–7490 (2001).

It will be understood that various details of the invention can be changed without departing from the scope of the invention. Furthermore, the foregoing description is for the purpose of illustration only, and not for the purpose of limitation—the invention being defined by the claims appended hereto.

---

What is claimed is:

1. An isolated and modified human sodium channel type 1 alpha subunit (SCN1A) nucleic acid molecule comprising:
   (a) a nucleotide sequence comprising the nucleotide sequence of SEQ ID NO:1 comprising one or more mutations within nucleotides 1203–1209; or
   (b) a nucleotide sequence at least about 95% identical to SEQ ID NO:1, and further comprising one or more mutations within nucleotide positions corresponding to nucleotides 1203–1209 of SEQ ID NO:1
   wherein the nucleotide sequences of (a) and (b) encode an SCN1A voltage-gated sodium channel polypeptide that regulates $Na^+$ ion membrane permeation.

2. An isolated and modified human sodium channel type 1 alpha subunit (SCN1A) nucleic acid molecule comprising:
   (a) a nucleic acid molecule comprising a nucleotide sequence of SEQ ID NO:3; or
   (b) a nucleic acid molecule at least about 95% identical to SEQ ID NO:3, and wherein the nucleic acid molecule comprises a T to C transition at each of the nucleotide positions corresponding to nucleotides 1206 and 1209 of SEQ ID NO:3 and encodes an SCN1A voltage-gated sodium channel polypeptide that regulates $Na^+$ ion membrane permeation.

3. An isolated host cell for heterologous expression of a human sodium channel type 1 alpha subunit (SCN1A) polypeptide, the host cell comprising:
   (a) a polypeptide encoded by a nucleic acid molecule comprising a nucleotide sequence of SEQ ID NO:1 comprising one or more mutations within nucleotides 1203–1209; or
   (b) a polypeptide encoded by a nucleic acid molecule at least about 95% identical to SEQ ID NO:1 and further comprising one or more mutations within nucleotide positions corresponding to nucleotides 1203–1209 of SEQ ID NO:1 wherein the polypeptides of (a) and (b) each comprise an SCN1A voltage-gated sodium channel polypeptide that regulates Na⁺ ion membrane permeation.

4. An isolated host cell for heterologous expression of a human sodium channel type 1 alpha subunit (SCN1A) polypeptide, the host cell comprising:
(a) a polypeptide encoded by a nucleic acid molecule comprising a nucleotide sequence of SEQ ID NO:3; or
(b) a polypeptide that regulates Na⁺ ion membrane permeation, which is encoded by a nucleic acid molecule at least about 95% identical to SEQ ID NO:3, and wherein the nucleic acid molecule comprises a T to C transition at each of the nucleotide positions corresponding to nucleotides 1206 and 1209 of SEQ ID NO:3.

5. The host cell of claim 3 or 4, wherein the host cell comprises a mammalian cell.

6. The host cell of claim 5, wherein the mammalian cell comprises a human cell.

7. The host cell of claim 3 or 4, wherein the host cell is from a stable cell line.

8. The host cell of claim 3 or 4, further comprising a human sodium channel β-subunit, wherein the sodium channel β-subunit is expressed in the host cell.

9. The host cell of claim 8, wherein the human sodium channel β-subunit comprises a recombinantly expressed human sodium channel β-subunit.

10. The host cell of claim 8, wherein the human sodium channel β-subunit comprises human sodium channel type 1 beta subunit (SCN1B).

11. The host cell of claim 8, further comprising at least one other human sodium channel β-subunit, wherein the at least one other sodium channel β-subunit is expressed in the host cell.

12. The host cell of claim 11, wherein the at least one other human sodium channel β-subunit comprises human sodium channel type 2 beta subunit (SCN2B).

13. An isolated host cell for heterologous expression of a recombinant human sodium channel type 1 alpha subunit (SCN1A) polypeptide, the host cell comprising a construct comprising:
(a) a nucleotide sequence comprising the nucleotide sequence of SEQ ID NO:1 that comprises one or more mutations within nucleotides 1203–1209; or
(b) a nucleotide sequence at least about 95% identical to SEQ ID NO:1, and further comprising one or more mutations within nucleotide positions corresponding to nucleotides 1203–1209 of SEQ ID NO:1
wherein the nucleotide sequences of (a) and (b) encode an SCN1A voltage-gated sodium channel polypeptide that regulates Na⁺ ion membrane permeation.

14. An isolated host cell for heterologous expression of a recombinant human sodium channel type 1 alpha subunit (SCN1A) polypeptide, the host cell comprising a construct comprising:
(a) a nucleic acid molecule comprising a nucleotide sequence of SEQ ID NO:3; or
(b) a nucleic acid molecule at least about 95% identical to SEQ ID NO:3, and wherein the nucleic acid molecule comprises a T to C transition at each of the nucleotide positions corresponding to nucleotides 1206 and 1209 of SEQ ID NO:3 and encodes an SCN1A voltage-gated sodium channel polypeptide that regulates Na⁺ ion membrane permeation.

15. The host cell of claim 13 or 14, wherein the host cell comprises a mammalian cell.

16. The host cell of claim 15, wherein the mammalian cell comprises a human cell.

17. The host cell of claim 13 or 14, wherein the host cell is from a stable cell line.

18. The host cell of claim 13 or 14, further comprising a human sodium channel β-subunit, wherein the sodium channel β-subunit is expressed in the host cell.

19. The host cell of claim 18, wherein the human sodium channel β-subunit comprises a recombinantly expressed sodium channel β-subunit.

20. The host cell of claim 18, wherein the human sodium channel β-subunit comprises human sodium channel type 1 beta subunit (SCN1B).

21. The host cell of claim 18, further comprising at least one other human sodium channel β-subunit, wherein the at least one other sodium channel β-subunit is expressed in the host cell.

22. The host cell of claim 21, wherein the at least one other human sodium channel β-subunit comprises human sodium channel type 2 beta subunit (SCN2B).

23. A method for identifying a sodium channel modulator, the method comprising:
(a) providing a heterologous expression system whereby a human SCN1A polypeptide is expressed from a modified SCN1A nucleic acid molecule in a host cell, wherein the nucleic acid molecule encoding a human SCN1A polypeptide comprises:
(1) a nucleotide sequence comprising the nucleotide sequence of SEQ ID NO:1 comprising one or more mutations within nucleotides 1203–1209: or
(2) a nucleotide sequence at least 95% identical to SEQ ID NO:1, and further comprising one or more mutations within nucleotide positions corresponding to nucleotides 1203–1209 of SEQ ID NO:1; or
(3) a nucleotide sequence of SEQ ID NO:3; or
(4) a nucleotide sequence at least 95% identical to SEQ ID NO:3, and wherein the nucleic acid molecule comprises a T to C transition at each of the nucleotide positions corresponding to nucleotides 1206 and 1209 of SEQ ID NO:3, wherein the nucleotide sequences of (1), (2), (3), and (4) encode an SCN1A voltage-gated sodium channel polypeptide that regulates Na+ ion membrane permeation;
(b) providing a test substance to the system of (a);
(c) assaying sodium channel conductance in the presence of the test substance;
(d) comparing sodium channel conductance in the presence of the test substance with sodium channel conductance in the absence of the test compound; and
(e) identifying a test substance as a sodium channel modulator by measuring an increase or decrease in sodium channel conductance in the presence of the test substance as compared to sodium channel conductance in the absence of the test substance.

24. The method of claim 23, wherein the host cell comprises a mammalian cell.

25. The method of claim 24, wherein the mammalian cell comprises a human cell.

26. The method of claim 23, wherein the host cell is from a stable cell line.

27. The method of claim 23, wherein the host cell further comprises a human sodium channel β-subunit.

28. The method of claim 27, wherein the human sodium channel β-subunit comprises a recombinantly expressed human sodium channel β-subunit.

29. The method of claim 27, wherein the human sodium channel β-subunit comprises human SCN1B.

30. The method of claim 27, wherein the host cell comprises at least one other human sodium channel β-subunit, wherein the at least one other sodium channel β-subunit is expressed in the host cell.

31. The method of claim 30, wherein the at least one other human sodium channel β-subunit comprises human sodium channel type 2 beta subunit (SCN2B).

* * * * *

SEQUENCE LISTING

<160> NUMBER OF SEQ ID NOS: 27

<210> SEQ ID NO 1
<211> LENGTH: 7027
<212> TYPE: DNA
<213> ORGANISM: Homo sapiens
<220> FEATURE:
<221> NAME/KEY: CDS
<222> LOCATION: (1)..(6027)

<400> SEQUENCE: 1

```
atg gag caa aca gtg ctt gta cca cca gga cct gac agc ttc aac ttc      48
Met Glu Gln Thr Val Leu Val Pro Pro Gly Pro Asp Ser Phe Asn Phe
1               5                   10                  15 ttc acc aga gaa tct ctt gcg gct att gaa aga cgc att gca gaa gaa      96
Phe Thr Arg Glu Ser Leu Ala Ala Ile Glu Arg Arg Ile Ala Glu Glu
            20                  25                  30 aag gca aag aat ccc aaa cca gac aaa aaa gat gac gac gaa aat ggc     144
Lys Ala Lys Asn Pro Lys Pro Asp Lys Lys Asp Asp Asp Glu Asn Gly
        35                  40                  45 cca aag cca aat agt gac ttg gaa gct gga aag aac ctt cca ttt att     192
Pro Lys Pro Asn Ser Asp Leu Glu Ala Gly Lys Asn Leu Pro Phe Ile
    50                  55                  60 tat gga gac att cct cca gag atg gtg tca gag ccc ctg gag gac ctg     240
Tyr Gly Asp Ile Pro Pro Glu Met Val Ser Glu Pro Leu Glu Asp Leu
65                  70                  75                  80 gac ccc tac tat atc aat aag aaa act ttt ata gta ttg aat aaa ggg     288
Asp Pro Tyr Tyr Ile Asn Lys Lys Thr Phe Ile Val Leu Asn Lys Gly
                85                  90                  95
```

```
aag gcc atc ttc cgg ttc agt gcc acc tct gcc ctg tac att tta act       336
Lys Ala Ile Phe Arg Phe Ser Ala Thr Ser Ala Leu Tyr Ile Leu Thr
            100                 105                 110 ccc ttc aat cct ctt agg aaa ata gct att aag att ttg gta cat tca       384
Pro Phe Asn Pro Leu Arg Lys Ile Ala Ile Lys Ile Leu Val His Ser
        115                 120                 125 tta ttc agc atg cta att atg tgc act att ttg aca aac tgt gtg ttt       432
Leu Phe Ser Met Leu Ile Met Cys Thr Ile Leu Thr Asn Cys Val Phe
    130                 135                 140 atg aca atg agt aac cct cct gat tgg aca aag aat gta gaa tac acc       480
Met Thr Met Ser Asn Pro Pro Asp Trp Thr Lys Asn Val Glu Tyr Thr
145                 150                 155                 160 ttc aca gga ata tat act ttt gaa tca ctt ata aaa att att gca agg       528
Phe Thr Gly Ile Tyr Thr Phe Glu Ser Leu Ile Lys Ile Ile Ala Arg
                165                 170                 175 gga ttc tgt tta gaa gat ttt act ttc ctt cgg gat cca tgg aac tgg       576
Gly Phe Cys Leu Glu Asp Phe Thr Phe Leu Arg Asp Pro Trp Asn Trp
            180                 185                 190 ctc gat ttc act gtc att aca ttt gcg tac gtc aca gag ttt gtg gac       624
Leu Asp Phe Thr Val Ile Thr Phe Ala Tyr Val Thr Glu Phe Val Asp
        195                 200                 205 ctg ggc aat gtc tcg gca ttg aga aca ttc aga gtt ctc cga gca ttg       672
Leu Gly Asn Val Ser Ala Leu Arg Thr Phe Arg Val Leu Arg Ala Leu
    210                 215                 220 aag acg att tca gtc att cca ggc ctg aaa acc att gtg gga gcc ctg       720
Lys Thr Ile Ser Val Ile Pro Gly Leu Lys Thr Ile Val Gly Ala Leu
225                 230                 235                 240 atc cag tct gtg aag aag ctc tca gat gta atg atc ctg act gtg ttc       768
Ile Gln Ser Val Lys Lys Leu Ser Asp Val Met Ile Leu Thr Val Phe
                245                 250                 255 tgt ctg agc gta ttt gct cta att ggg ctg cag ctg ttc atg ggc aac       816
Cys Leu Ser Val Phe Ala Leu Ile Gly Leu Gln Leu Phe Met Gly Asn
            260                 265                 270 ctg agg aat aaa tgt ata caa tgg cct ccc acc aat gct tcc ttg gag       864
Leu Arg Asn Lys Cys Ile Gln Trp Pro Pro Thr Asn Ala Ser Leu Glu
        275                 280                 285 gaa cat agt ata gaa aag aat ata act gtg aat tat aat ggt aca ctt       912
Glu His Ser Ile Glu Lys Asn Ile Thr Val Asn Tyr Asn Gly Thr Leu
    290                 295                 300 ata aat gaa act gtc ttt gag ttt gac tgg aag tca tat att caa gat       960
Ile Asn Glu Thr Val Phe Glu Phe Asp Trp Lys Ser Tyr Ile Gln Asp
305                 310                 315                 320 tca aga tat cat tat ttc ctg gag ggt ttt tta gat gca cta cta tgt      1008
Ser Arg Tyr His Tyr Phe Leu Glu Gly Phe Leu Asp Ala Leu Leu Cys
                325                 330                 335 gga aat agc tct gat gca ggc caa tgt cca gag gga tat atg tgt gtg      1056
Gly Asn Ser Ser Asp Ala Gly Gln Cys Pro Glu Gly Tyr Met Cys Val
            340                 345                 350 aaa gct ggt aga aat ccc aat tat ggc tac aca agc ttt gat acc ttc      1104
Lys Ala Gly Arg Asn Pro Asn Tyr Gly Tyr Thr Ser Phe Asp Thr Phe
        355                 360                 365 agt tgg gct ttt ttg tcc ttg ttt cga cta atg act cag gac ttc tgg      1152
Ser Trp Ala Phe Leu Ser Leu Phe Arg Leu Met Thr Gln Asp Phe Trp
    370                 375                 380 gaa aat ctt tat caa ctg aca tta cgt gct gct ggg aaa acg tac atg      1200
Glu Asn Leu Tyr Gln Leu Thr Leu Arg Ala Ala Gly Lys Thr Tyr Met
385                 390                 395                 400 ata ttt ttt gta ttg gtc att ttc ttg ggc tca ttc tac cta ata aat      1248
Ile Phe Phe Val Leu Val Ile Phe Leu Gly Ser Phe Tyr Leu Ile Asn
```

-continued

```
                405                 410                 415
ttg atc ctg gct gtg gtg gcc atg gcc tac gag gaa cag aat cag gcc    1296
Leu Ile Leu Ala Val Val Ala Met Ala Tyr Glu Glu Gln Asn Gln Ala
            420                 425                 430 acc ttg gaa gaa gca gaa cag aaa gag gcc gaa ttt cag cag atg att    1344
Thr Leu Glu Glu Ala Glu Gln Lys Glu Ala Glu Phe Gln Gln Met Ile
        435                 440                 445 gaa cag ctt aaa aag caa cag gag gca gct cag cag gca gca acg gca    1392
Glu Gln Leu Lys Lys Gln Gln Glu Ala Ala Gln Gln Ala Ala Thr Ala
    450                 455                 460 act gcc tca gaa cat tcc aga gag ccc agt gca gca ggc agg ctc tca    1440
Thr Ala Ser Glu His Ser Arg Glu Pro Ser Ala Ala Gly Arg Leu Ser
465                 470                 475                 480 gac agc tca tct gaa gcc tct aag ttg agt tcc aag agt gct aag gaa    1488
Asp Ser Ser Ser Glu Ala Ser Lys Leu Ser Ser Lys Ser Ala Lys Glu
                485                 490                 495 aga aga aat cgg agg aag aaa aga aaa cag aaa gag cag tct ggt ggg    1536
Arg Arg Asn Arg Arg Lys Lys Arg Lys Gln Lys Glu Gln Ser Gly Gly
            500                 505                 510 gaa gag aaa gat gag gat gaa ttc caa aaa tct gaa tct gag gac agc    1584
Glu Glu Lys Asp Glu Asp Glu Phe Gln Lys Ser Glu Ser Glu Asp Ser
        515                 520                 525 atc agg agg aaa ggt ttt cgc ttc tcc att gaa ggg aac cga ttg aca    1632
Ile Arg Arg Lys Gly Phe Arg Phe Ser Ile Glu Gly Asn Arg Leu Thr
    530                 535                 540 tat gaa aag agg tac tcc tcc cca cac cag tct ttg ttg agc atc cgt    1680
Tyr Glu Lys Arg Tyr Ser Ser Pro His Gln Ser Leu Leu Ser Ile Arg
545                 550                 555                 560 ggc tcc cta ttt tca cca agg cga aat agc aga aca agc ctt ttc agc    1728
Gly Ser Leu Phe Ser Pro Arg Arg Asn Ser Arg Thr Ser Leu Phe Ser
                565                 570                 575 ttt aga ggg cga gca aag gat gtg gga tct gag aac gac ttc gca gat    1776
Phe Arg Gly Arg Ala Lys Asp Val Gly Ser Glu Asn Asp Phe Ala Asp
            580                 585                 590 gat gag cac agc acc ttt gag gat aac gag agc cgt aga gat tcc ttg    1824
Asp Glu His Ser Thr Phe Glu Asp Asn Glu Ser Arg Arg Asp Ser Leu
        595                 600                 605 ttt gtg ccc cga cga cac gga gag aga cgc aac agc aac ctg agt cag    1872
Phe Val Pro Arg Arg His Gly Glu Arg Arg Asn Ser Asn Leu Ser Gln
    610                 615                 620 acc agt agg tca tcc cgg atg ctg gca gtg ttt cca gcg aat ggg aag    1920
Thr Ser Arg Ser Ser Arg Met Leu Ala Val Phe Pro Ala Asn Gly Lys
625                 630                 635                 640 atg cac agc act gtg gat tgc aat ggt gtg gtt tcc ttg gtt ggt gga    1968
Met His Ser Thr Val Asp Cys Asn Gly Val Val Ser Leu Val Gly Gly
                645                 650                 655 cct tca gtt cct aca tcg cct gtt gga cag ctt ctg cca gag gtg ata    2016
Pro Ser Val Pro Thr Ser Pro Val Gly Gln Leu Leu Pro Glu Val Ile
            660                 665                 670 ata gat aag cca gct act gat gac aat gga aca acc act gaa act gaa    2064
Ile Asp Lys Pro Ala Thr Asp Asp Asn Gly Thr Thr Thr Glu Thr Glu
        675                 680                 685 atg aga aag aga agg tca agt tct ttc cac gtt tcc atg gac ttt cta    2112
Met Arg Lys Arg Arg Ser Ser Ser Phe His Val Ser Met Asp Phe Leu
    690                 695                 700 gaa gat cct tcc caa agg caa cga gca atg agt ata gcc agc att cta    2160
Glu Asp Pro Ser Gln Arg Gln Arg Ala Met Ser Ile Ala Ser Ile Leu
705                 710                 715                 720 aca aat aca gta gaa gaa ctt gaa gaa tcc agg cag aaa tgc cca ccc    2208
```

```
                                                                    -continued Thr Asn Thr Val Glu Glu Leu Glu Glu Ser Arg Gln Lys Cys Pro Pro
            725                 730                 735 tgt tgg tat aaa ttt tcc aac ata ttc tta atc tgg gac tgt tct cca    2256
Cys Trp Tyr Lys Phe Ser Asn Ile Phe Leu Ile Trp Asp Cys Ser Pro
            740                 745                 750 tat tgg tta aaa gtg aaa cat gtt gtc aac ctg gtt gtg atg gac cca    2304
Tyr Trp Leu Lys Val Lys His Val Val Asn Leu Val Val Met Asp Pro
            755                 760                 765 ttt gtt gac ctg gcc atc acc atc tgt att gtc tta aat act ctt ttc    2352
Phe Val Asp Leu Ala Ile Thr Ile Cys Ile Val Leu Asn Thr Leu Phe
            770                 775                 780 atg gcc atg gag cac tat cca atg acg gac cat ttc aat aat gtg ctt    2400
Met Ala Met Glu His Tyr Pro Met Thr Asp His Phe Asn Asn Val Leu
785                 790                 795                 800 aca gta gga aac ttg gtt ttc act ggg atc ttt aca gca gaa atg ttt    2448
Thr Val Gly Asn Leu Val Phe Thr Gly Ile Phe Thr Ala Glu Met Phe
                    805                 810                 815 ctg aaa att att gcc atg gat cct tac tat tat ttc caa gaa ggc tgg    2496
Leu Lys Ile Ile Ala Met Asp Pro Tyr Tyr Tyr Phe Gln Glu Gly Trp
                    820                 825                 830 aat atc ttt gac ggt ttt att gtg acg ctt agc ctg gta gaa ctt gga    2544
Asn Ile Phe Asp Gly Phe Ile Val Thr Leu Ser Leu Val Glu Leu Gly
                    835                 840                 845 ctc gcc aat gtg gaa gga tta tct gtt ctc cgt tca ttt cga ttg ctg    2592
Leu Ala Asn Val Glu Gly Leu Ser Val Leu Arg Ser Phe Arg Leu Leu
            850                 855                 860 cga gtt ttc aag ttg gca aaa tct tgg cca acg tta aat atg cta ata    2640
Arg Val Phe Lys Leu Ala Lys Ser Trp Pro Thr Leu Asn Met Leu Ile
865                 870                 875                 880 aag atc atc ggc aat tcc gtg ggg gct ctg gga aat tta acc ctc gtc    2688
Lys Ile Ile Gly Asn Ser Val Gly Ala Leu Gly Asn Leu Thr Leu Val
                    885                 890                 895 ttg gcc atc atc gtc ttc att ttt gcc gtg gtc ggc atg cag ctc ttt    2736
Leu Ala Ile Ile Val Phe Ile Phe Ala Val Val Gly Met Gln Leu Phe
                    900                 905                 910 ggt aaa agc tac aaa gat tgt gtc tgc aag atc gcc agt gat tgt caa    2784
Gly Lys Ser Tyr Lys Asp Cys Val Cys Lys Ile Ala Ser Asp Cys Gln
            915                 920                 925 ctc cca cgc tgg cac atg aat gac ttc ttc cac tcc ttc ctg att gtg    2832
Leu Pro Arg Trp His Met Asn Asp Phe Phe His Ser Phe Leu Ile Val
            930                 935                 940 ttc cgc gtg ctg tgt ggg gag tgg ata gag acc atg tgg gac tgt atg    2880
Phe Arg Val Leu Cys Gly Glu Trp Ile Glu Thr Met Trp Asp Cys Met
945                 950                 955                 960 gag gtt gct ggt caa gcc atg tgc ctt act gtc ttc atg atg gtc atg    2928
Glu Val Ala Gly Gln Ala Met Cys Leu Thr Val Phe Met Met Val Met
                    965                 970                 975 gtg att gga aac cta gtg gtc ctg aat ctc ttt ctg gcc ttg ctt ctg    2976
Val Ile Gly Asn Leu Val Val Leu Asn Leu Phe Leu Ala Leu Leu Leu
                    980                 985                 990 agc tca ttt agt gca gac aac ctt gca gcc act gat gat gat aat gaa    3024
Ser Ser Phe Ser Ala Asp Asn Leu Ala Ala Thr Asp Asp Asp Asn Glu
                    995                 1000                1005 atg aat aat ctc caa att gct gtg gat agg atg cac aaa gga gta       3069
Met Asn Asn Leu Gln Ile Ala Val Asp Arg Met His Lys Gly Val
            1010                1015                1020 gct tat gtg aaa aga aaa ata tat gaa ttt att caa cag tcc ttc       3114
Ala Tyr Val Lys Arg Lys Ile Tyr Glu Phe Ile Gln Gln Ser Phe
            1025                1030                1035
```

```
att agg aaa caa aag att tta gat gaa att aaa cca ctt gat gat      3159
Ile Arg Lys Gln Lys Ile Leu Asp Glu Ile Lys Pro Leu Asp Asp
    1040            1045                1050 cta aac aac aag aaa gac agt tgt atg tcc aat cat aca gca gaa      3204
Leu Asn Asn Lys Lys Asp Ser Cys Met Ser Asn His Thr Ala Glu
    1055            1060                1065 att ggg aaa gat ctt gac tat ctt aaa gat gta aat gga act aca      3249
Ile Gly Lys Asp Leu Asp Tyr Leu Lys Asp Val Asn Gly Thr Thr
    1070            1075                1080 agt ggt ata gga act ggc agc agt gtt gaa aaa tac att att gat      3294
Ser Gly Ile Gly Thr Gly Ser Ser Val Glu Lys Tyr Ile Ile Asp
    1085            1090                1095 gaa agt gat tac atg tca ttc ata aac aac ccc agt ctt act gtg      3339
Glu Ser Asp Tyr Met Ser Phe Ile Asn Asn Pro Ser Leu Thr Val
    1100            1105                1110 act gta cca att gct gta gga gaa tct gac ttt gaa aat tta aac      3384
Thr Val Pro Ile Ala Val Gly Glu Ser Asp Phe Glu Asn Leu Asn
    1115            1120                1125 acg gaa gac ttt agt agt gaa tcg gat ctg gaa gaa agc aaa gag      3429
Thr Glu Asp Phe Ser Ser Glu Ser Asp Leu Glu Glu Ser Lys Glu
    1130            1135                1140 aaa ctg aat gaa agc agt agc tca tca gaa ggt agc act gtg gac      3474
Lys Leu Asn Glu Ser Ser Ser Ser Ser Glu Gly Ser Thr Val Asp
    1145            1150                1155 atc ggc gca cct gta gaa gaa cag ccc gta gtg gaa cct gaa gaa      3519
Ile Gly Ala Pro Val Glu Glu Gln Pro Val Val Glu Pro Glu Glu
    1160            1165                1170 act ctt gaa cca gaa gct tgt ttc act gaa ggc tgt gta caa aga      3564
Thr Leu Glu Pro Glu Ala Cys Phe Thr Glu Gly Cys Val Gln Arg
    1175            1180                1185 ttc aag tgt tgt caa atc aat gtg gaa gaa ggc aga gga aaa caa      3609
Phe Lys Cys Cys Gln Ile Asn Val Glu Glu Gly Arg Gly Lys Gln
    1190            1195                1200 tgg tgg aac ctg aga agg acg tgt ttc cga ata gtt gaa cat aac      3654
Trp Trp Asn Leu Arg Arg Thr Cys Phe Arg Ile Val Glu His Asn
    1205            1210                1215 tgg ttt gag acc ttc att gtt ttc atg att ctc ctt agt agt ggt      3699
Trp Phe Glu Thr Phe Ile Val Phe Met Ile Leu Leu Ser Ser Gly
    1220            1225                1230 gct ctg gca ttt gaa gat ata tat att gat cag cga aag acg att      3744
Ala Leu Ala Phe Glu Asp Ile Tyr Ile Asp Gln Arg Lys Thr Ile
    1235            1240                1245 aag acg atg ttg gaa tat gct gac aag gtt ttc act tac att ttc      3789
Lys Thr Met Leu Glu Tyr Ala Asp Lys Val Phe Thr Tyr Ile Phe
    1250            1255                1260 att ctg gaa atg ctt cta aaa tgg gtg gca tat ggc tat caa aca      3834
Ile Leu Glu Met Leu Leu Lys Trp Val Ala Tyr Gly Tyr Gln Thr
    1265            1270                1275 tat ttc acc aat gcc tgg tgt tgg ctg gac ttc tta att gtt gat      3879
Tyr Phe Thr Asn Ala Trp Cys Trp Leu Asp Phe Leu Ile Val Asp
    1280            1285                1290 gtt tca ttg gtc agt tta aca gca aat gcc ttg ggt tac tca gaa      3924
Val Ser Leu Val Ser Leu Thr Ala Asn Ala Leu Gly Tyr Ser Glu
    1295            1300                1305 ctt gga gcc atc aaa tct ctc agg aca cta aga gct ctg aga cct      3969
Leu Gly Ala Ile Lys Ser Leu Arg Thr Leu Arg Ala Leu Arg Pro
    1310            1315                1320 cta aga gcc tta tct cga ttt gaa ggg atg agg gtg gtt gtg aat      4014
Leu Arg Ala Leu Ser Arg Phe Glu Gly Met Arg Val Val Val Asn
    1325            1330                1335
```

-continued

```
gcc ctt tta gga gca att cca tcc atc atg aat gtg ctt ctg gtt      4059
Ala Leu Leu Gly Ala Ile Pro Ser Ile Met Asn Val Leu Leu Val
1340                1345                1350 tgt ctt ata ttc tgg cta att ttc agc atc atg ggc gta aat ttg      4104
Cys Leu Ile Phe Trp Leu Ile Phe Ser Ile Met Gly Val Asn Leu
    1355                1360                1365 ttt gct ggc aaa ttc tac cac tgt att aac acc aca act ggt gac      4149
Phe Ala Gly Lys Phe Tyr His Cys Ile Asn Thr Thr Thr Gly Asp
1370                1375                1380 agg ttt gac atc gaa gac gtg aat aat cat act gat tgc cta aaa      4194
Arg Phe Asp Ile Glu Asp Val Asn Asn His Thr Asp Cys Leu Lys
    1385                1390                1395 cta ata gaa aga aat gag act gct cga tgg aaa aat gtg aaa gta      4239
Leu Ile Glu Arg Asn Glu Thr Ala Arg Trp Lys Asn Val Lys Val
1400                1405                1410 aac ttt gat aat gta gga ttt ggg tat ctc tct ttg ctt caa gtt      4284
Asn Phe Asp Asn Val Gly Phe Gly Tyr Leu Ser Leu Leu Gln Val
    1415                1420                1425 gcc aca ttc aaa gga tgg atg gat ata atg tat gca gca gtt gat      4329
Ala Thr Phe Lys Gly Trp Met Asp Ile Met Tyr Ala Ala Val Asp
1430                1435                1440 tcc aga aat gtg gaa ctc cag cct aag tat gaa gaa agt ctg tac      4374
Ser Arg Asn Val Glu Leu Gln Pro Lys Tyr Glu Glu Ser Leu Tyr
    1445                1450                1455 atg tat ctt tac ttt gtt att ttc atc atc ttt ggg tcc ttc ttc      4419
Met Tyr Leu Tyr Phe Val Ile Phe Ile Ile Phe Gly Ser Phe Phe
1460                1465                1470 acc ttg aac ctg ttt att ggt gtc atc ata gat aat ttc aac cag      4464
Thr Leu Asn Leu Phe Ile Gly Val Ile Ile Asp Asn Phe Asn Gln
    1475                1480                1485 cag aaa aag aag ttt gga ggt caa gac atc ttt atg aca gaa gaa      4509
Gln Lys Lys Lys Phe Gly Gly Gln Asp Ile Phe Met Thr Glu Glu
1490                1495                1500 cag aag aaa tac tat aat gca atg aaa aaa tta gga tcg aaa aaa      4554
Gln Lys Lys Tyr Tyr Asn Ala Met Lys Lys Leu Gly Ser Lys Lys
    1505                1510                1515 ccg caa aag cct ata cct cga cca gga aac aaa ttt caa gga atg      4599
Pro Gln Lys Pro Ile Pro Arg Pro Gly Asn Lys Phe Gln Gly Met
1520                1525                1530 gtc ttt gac ttc gta acc aga caa gtt ttt gac ata agc atc atg      4644
Val Phe Asp Phe Val Thr Arg Gln Val Phe Asp Ile Ser Ile Met
    1535                1540                1545 att ctc atc tgt ctt aac atg gtc aca atg atg gtg gaa aca gat      4689
Ile Leu Ile Cys Leu Asn Met Val Thr Met Met Val Glu Thr Asp
1550                1555                1560 gac cag agt gaa tat gtg act acc att ttg tca cgc atc aat ctg      4734
Asp Gln Ser Glu Tyr Val Thr Thr Ile Leu Ser Arg Ile Asn Leu
    1565                1570                1575 gtg ttc att gtg cta ttt act gga gag tgt gta ctg aaa ctc atc      4779
Val Phe Ile Val Leu Phe Thr Gly Glu Cys Val Leu Lys Leu Ile
1580                1585                1590 tct cta cgc cat tat tat ttt acc att gga tgg aat att ttt gat      4824
Ser Leu Arg His Tyr Tyr Phe Thr Ile Gly Trp Asn Ile Phe Asp
    1595                1600                1605 ttt gtg gtt gtc atc ctc tcc att gta ggt atg ttt ctt gcc gag      4869
Phe Val Val Val Ile Leu Ser Ile Val Gly Met Phe Leu Ala Glu
1610                1615                1620 ctg ata gaa aag tat ttc gtg tcc cct acc ctg ttc cga gtg atc      4914
Leu Ile Glu Lys Tyr Phe Val Ser Pro Thr Leu Phe Arg Val Ile
    1625                1630                1635
```

-continued

| | | | | | | | | | | | |
|---|---|---|---|---|---|---|---|---|---|---|---|
| | 1625 | | | 1630 | | | | 1635 | | | |
| cgt | ctt | gct | agg | att | ggc | cga | atc | cta | cgt | ctg | atc | aaa | gga | gca | 4959 |
| Arg | Leu | Ala | Arg | Ile | Gly | Arg | Ile | Leu | Arg | Leu | Ile | Lys | Gly | Ala | |
| 1640 | | | | 1645 | | | | | 1650 | | | | | | |

| aag | ggg | atc | cgc | acg | ctg | ctc | ttt | gct | ttg | atg | atg | tcc | ctt | cct | 5004 |
|---|---|---|---|---|---|---|---|---|---|---|---|---|---|---|---|
| Lys | Gly | Ile | Arg | Thr | Leu | Leu | Phe | Ala | Leu | Met | Met | Ser | Leu | Pro | |
| 1655 | | | | | 1660 | | | | 1665 | | | | | | |

| gcg | ttg | ttt | aac | atc | ggc | ctc | cta | ctc | ttc | cta | gtc | atg | ttc | atc | 5049 |
|---|---|---|---|---|---|---|---|---|---|---|---|---|---|---|---|
| Ala | Leu | Phe | Asn | Ile | Gly | Leu | Leu | Leu | Phe | Leu | Val | Met | Phe | Ile | |
| 1670 | | | | | 1675 | | | | 1680 | | | | | | |

| tac | gcc | atc | ttt | ggg | atg | tcc | aac | ttt | gcc | tat | gtt | aag | agg | gaa | 5094 |
|---|---|---|---|---|---|---|---|---|---|---|---|---|---|---|---|
| Tyr | Ala | Ile | Phe | Gly | Met | Ser | Asn | Phe | Ala | Tyr | Val | Lys | Arg | Glu | |
| 1685 | | | | | 1690 | | | | 1695 | | | | | | |

| gtt | ggg | atc | gat | gac | atg | ttc | aac | ttt | gag | acc | ttt | ggc | aac | agc | 5139 |
|---|---|---|---|---|---|---|---|---|---|---|---|---|---|---|---|
| Val | Gly | Ile | Asp | Asp | Met | Phe | Asn | Phe | Glu | Thr | Phe | Gly | Asn | Ser | |
| 1700 | | | | | 1705 | | | | 1710 | | | | | | |

| atg | atc | tgc | cta | ttc | caa | att | aca | acc | tct | gct | ggc | tgg | gat | gga | 5184 |
|---|---|---|---|---|---|---|---|---|---|---|---|---|---|---|---|
| Met | Ile | Cys | Leu | Phe | Gln | Ile | Thr | Thr | Ser | Ala | Gly | Trp | Asp | Gly | |
| 1715 | | | | | 1720 | | | | 1725 | | | | | | |

| ttg | cta | gca | ccc | att | ctc | aac | agt | aag | cca | ccc | gac | tgt | gac | cct | 5229 |
|---|---|---|---|---|---|---|---|---|---|---|---|---|---|---|---|
| Leu | Leu | Ala | Pro | Ile | Leu | Asn | Ser | Lys | Pro | Pro | Asp | Cys | Asp | Pro | |
| 1730 | | | | | 1735 | | | | 1740 | | | | | | |

| aat | aaa | gtt | aac | cct | gga | agc | tca | gtt | aag | gga | gac | tgt | ggg | aac | 5274 |
|---|---|---|---|---|---|---|---|---|---|---|---|---|---|---|---|
| Asn | Lys | Val | Asn | Pro | Gly | Ser | Ser | Val | Lys | Gly | Asp | Cys | Gly | Asn | |
| 1745 | | | | | 1750 | | | | 1755 | | | | | | |

| cca | tct | gtt | gga | att | ttc | ttt | ttt | gtc | agt | tac | atc | atc | ata | tcc | 5319 |
|---|---|---|---|---|---|---|---|---|---|---|---|---|---|---|---|
| Pro | Ser | Val | Gly | Ile | Phe | Phe | Phe | Val | Ser | Tyr | Ile | Ile | Ile | Ser | |
| 1760 | | | | | 1765 | | | | 1770 | | | | | | |

| ttc | ctg | gtt | gtg | gtg | aac | atg | tac | atc | gcg | gtc | atc | ctg | gag | aac | 5364 |
|---|---|---|---|---|---|---|---|---|---|---|---|---|---|---|---|
| Phe | Leu | Val | Val | Val | Asn | Met | Tyr | Ile | Ala | Val | Ile | Leu | Glu | Asn | |
| 1775 | | | | | 1780 | | | | 1785 | | | | | | |

| ttc | agt | gtt | gct | act | gaa | gaa | agt | gca | gag | cct | ctg | agt | gag | gat | 5409 |
|---|---|---|---|---|---|---|---|---|---|---|---|---|---|---|---|
| Phe | Ser | Val | Ala | Thr | Glu | Glu | Ser | Ala | Glu | Pro | Leu | Ser | Glu | Asp | |
| 1790 | | | | | 1795 | | | | 1800 | | | | | | |

| gac | ttt | gag | atg | ttc | tat | gag | gtt | tgg | gag | aag | ttt | gat | ccc | gat | 5454 |
|---|---|---|---|---|---|---|---|---|---|---|---|---|---|---|---|
| Asp | Phe | Glu | Met | Phe | Tyr | Glu | Val | Trp | Glu | Lys | Phe | Asp | Pro | Asp | |
| 1805 | | | | | 1810 | | | | 1815 | | | | | | |

| gca | act | cag | ttc | atg | gaa | ttt | gaa | aaa | tta | tct | cag | ttt | gca | gct | 5499 |
|---|---|---|---|---|---|---|---|---|---|---|---|---|---|---|---|
| Ala | Thr | Gln | Phe | Met | Glu | Phe | Glu | Lys | Leu | Ser | Gln | Phe | Ala | Ala | |
| 1820 | | | | | 1825 | | | | 1830 | | | | | | |

| gcg | ctt | gaa | ccg | cct | ctc | aat | ctg | cca | caa | cca | aac | aaa | ctc | cag | 5544 |
|---|---|---|---|---|---|---|---|---|---|---|---|---|---|---|---|
| Ala | Leu | Glu | Pro | Pro | Leu | Asn | Leu | Pro | Gln | Pro | Asn | Lys | Leu | Gln | |
| 1835 | | | | | 1840 | | | | 1845 | | | | | | |

| ctc | att | gcc | atg | gat | ttg | ccc | atg | gtg | agt | ggt | gac | cgg | atc | cac | 5589 |
|---|---|---|---|---|---|---|---|---|---|---|---|---|---|---|---|
| Leu | Ile | Ala | Met | Asp | Leu | Pro | Met | Val | Ser | Gly | Asp | Arg | Ile | His | |
| 1850 | | | | | 1855 | | | | 1860 | | | | | | |

| tgt | ctt | gat | atc | tta | ttt | gct | ttt | aca | aag | cgg | gtt | cta | gga | gag | 5634 |
|---|---|---|---|---|---|---|---|---|---|---|---|---|---|---|---|
| Cys | Leu | Asp | Ile | Leu | Phe | Ala | Phe | Thr | Lys | Arg | Val | Leu | Gly | Glu | |
| 1865 | | | | | 1870 | | | | 1875 | | | | | | |

| agt | gga | gag | atg | gat | gct | cta | cga | ata | cag | atg | gaa | gag | cga | ttc | 5679 |
|---|---|---|---|---|---|---|---|---|---|---|---|---|---|---|---|
| Ser | Gly | Glu | Met | Asp | Ala | Leu | Arg | Ile | Gln | Met | Glu | Glu | Arg | Phe | |
| 1880 | | | | | 1885 | | | | 1890 | | | | | | |

| atg | gct | tcc | aat | cct | tcc | aag | gtc | tcc | tat | cag | cca | atc | act | act | 5724 |
|---|---|---|---|---|---|---|---|---|---|---|---|---|---|---|---|
| Met | Ala | Ser | Asn | Pro | Ser | Lys | Val | Ser | Tyr | Gln | Pro | Ile | Thr | Thr | |
| 1895 | | | | | 1900 | | | | 1905 | | | | | | |

| act | tta | aaa | cga | aaa | caa | gag | gaa | gta | tct | gct | gtc | att | att | cag | 5769 |
|---|---|---|---|---|---|---|---|---|---|---|---|---|---|---|---|
| Thr | Leu | Lys | Arg | Lys | Gln | Glu | Glu | Val | Ser | Ala | Val | Ile | Ile | Gln | |
| 1910 | | | | | 1915 | | | | 1920 | | | | | | |

| cgt | gct | tac | aga | cgc | cac | ctt | tta | aag | cga | act | gta | aaa | caa | gct | 5814 |

-continued

```
Arg Ala Tyr Arg Arg His Leu Leu Lys Arg Thr Val Lys Gln Ala
    1925                1930                1935 tcc ttt acg tac aat aaa aac aaa atc aaa ggt ggg gct aat ctt      5859
Ser Phe Thr Tyr Asn Lys Asn Lys Ile Lys Gly Gly Ala Asn Leu
    1940                1945                1950 ctt ata aaa gaa gac atg ata att gac aga ata aat gaa aac tct      5904
Leu Ile Lys Glu Asp Met Ile Ile Asp Arg Ile Asn Glu Asn Ser
    1955                1960                1965 att aca gaa aaa act gat ctg acc atg tcc act gca gct tgt cca      5949
Ile Thr Glu Lys Thr Asp Leu Thr Met Ser Thr Ala Ala Cys Pro
    1970                1975                1980 cct tcc tat gac cgg gtg aca aag cca att gtg gaa aaa cat gag      5994
Pro Ser Tyr Asp Arg Val Thr Lys Pro Ile Val Glu Lys His Glu
    1985                1990                1995 caa gaa ggc aaa gat gaa aaa gcc aaa ggg aaa taaatgaaaa           6037
Gln Glu Gly Lys Asp Glu Lys Ala Lys Gly Lys
    2000                2005 taaataaaaa taattgggtg acaaattgtt tacagcctgt gaaggtgatg tattttatc  6097
aacaggactc ctttaggagg tcaatgccaa actgactgtt tttacacaaa tctccttaag  6157
gtcagtgcct acaataagac agtgacccct tgtcagcaaa ctgtgactct gtgtaaaggg  6217
gagatgacct tgacaggagg ttactgttct cactaccagc tgacactgct gaagataaga  6277
tgcacaatgg ctagtcagac tgtagggacc agtttcaagg ggtgcaaacc tgtgattttg  6337
gggttgttta acatgaaaca ctttagtgta gtaattgtat ccactgtttg catttcaact  6397
gccacatttg tcacatttt atggaatctg ttagtggatt catctttttg ttaatccatg   6457
tgtttattat atgtgactat ttttgtaaac gaagtttctg ttgagaaata ggctaaggac  6517
ctctataaca ggtatgccac ctgggggta tggcaaccac atggccctcc cagctacaca   6577
aagtcgtggt tgcatgagg gcatgctgca cttagagatc atgcatgaga aaaagtcaca   6637
agaaaaacaa attcttaaat ttcaccatat ttctgggagg ggtaattggg tgataagtgg  6697
aggtgctttg ttgatcttgt tttgcgaaat ccagccccta gaccaagtag attatttgtg  6757
ggtaggccag taaatcttag caggtgcaaa cttcattcaa atgtttggag tcataaatgt  6817
tatgtttctt tttgttgtat taaaaaaaaa acctgaatag tgaatattgc ccctcaccct  6877
ccaccgccag aagactgaat tgaccaaaat tactctttat aaatttctgc tttttcctgc  6937
actttgttta gccatcttcg gctctcagca aggttgacac tgtatatgtt aatgaaatgc  6997
tatttattat gtaaatagtc attttaccct                                   7027
```

<210> SEQ ID NO 2
<211> LENGTH: 2009
<212> TYPE: PRT
<213> ORGANISM: Homo sapiens

<400> SEQUENCE: 2

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80
```

-continued

```
Asp Pro Tyr Tyr Ile Asn Lys Lys Thr Phe Ile Val Leu Asn Lys Gly
             85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Lys Ile Leu Val His Ser
            115                 120                 125

Leu Phe Ser Met Leu Ile Met Cys Thr Ile Leu Thr Asn Cys Val Phe
            130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Leu Arg Asp Pro Trp Asn Trp
            180                 185                 190

Leu Asp Phe Thr Val Ile Thr Phe Ala Tyr Val Thr Glu Phe Val Asp
            195                 200                 205

Leu Gly Asn Val Ser Ala Leu Arg Thr Phe Arg Val Leu Arg Ala Leu
            210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
            275                 280                 285

Glu His Ser Ile Glu Lys Asn Ile Thr Val Asn Tyr Asn Gly Thr Leu
            290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
            355                 360                 365

Ser Trp Ala Phe Leu Ser Leu Phe Arg Leu Met Thr Gln Asp Phe Trp
            370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
            435                 440                 445

Glu Gln Leu Lys Lys Gln Gln Glu Ala Ala Gln Gln Ala Ala Thr Ala
            450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
            485                 490                 495
```

-continued

```
Arg Arg Asn Arg Arg Lys Lys Arg Lys Gln Lys Glu Gln Ser Gly Gly
            500                 505                 510
Glu Glu Lys Asp Glu Asp Glu Phe Gln Lys Ser Glu Ser Glu Asp Ser
        515                 520                 525
Ile Arg Arg Lys Gly Phe Arg Phe Ser Ile Glu Gly Asn Arg Leu Thr
    530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
            580                 585                 590
Asp Glu His Ser Thr Phe Glu Asp Asn Glu Ser Arg Arg Asp Ser Leu
        595                 600                 605
Phe Val Pro Arg Arg His Gly Glu Arg Arg Asn Ser Asn Leu Ser Gln
    610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                645                 650                 655
Pro Ser Val Pro Thr Ser Pro Val Gly Gln Leu Leu Pro Glu Val Ile
            660                 665                 670
Ile Asp Lys Pro Ala Thr Asp Asp Asn Gly Thr Thr Thr Glu Thr Glu
        675                 680                 685
Met Arg Lys Arg Arg Ser Ser Ser Phe His Val Ser Met Asp Phe Leu
    690                 695                 700
Glu Asp Pro Ser Gln Arg Gln Arg Ala Met Ser Ile Ala Ser Ile Leu
705                 710                 715                 720
Thr Asn Thr Val Glu Glu Leu Glu Glu Ser Arg Gln Lys Cys Pro Pro
                725                 730                 735
Cys Trp Tyr Lys Phe Ser Asn Ile Phe Leu Ile Trp Asp Cys Ser Pro
            740                 745                 750
Tyr Trp Leu Lys Val Lys His Val Val Asn Leu Val Val Met Asp Pro
        755                 760                 765
Phe Val Asp Leu Ala Ile Thr Ile Cys Ile Val Leu Asn Thr Leu Phe
    770                 775                 780
Met Ala Met Glu His Tyr Pro Met Thr Asp His Phe Asn Asn Val Leu
785                 790                 795                 800
Thr Val Gly Asn Leu Val Phe Thr Gly Ile Phe Thr Ala Glu Met Phe
                805                 810                 815
Leu Lys Ile Ile Ala Met Asp Pro Tyr Tyr Tyr Phe Gln Glu Gly Trp
            820                 825                 830
Asn Ile Phe Asp Gly Phe Ile Val Thr Leu Ser Leu Val Glu Leu Gly
        835                 840                 845
Leu Ala Asn Val Glu Gly Leu Ser Val Leu Arg Ser Phe Arg Leu Leu
    850                 855                 860
Arg Val Phe Lys Leu Ala Lys Ser Trp Pro Thr Leu Asn Met Leu Ile
865                 870                 875                 880
Lys Ile Ile Gly Asn Ser Val Gly Ala Leu Gly Asn Leu Thr Leu Val
                885                 890                 895
Leu Ala Ile Ile Val Phe Ile Phe Ala Val Val Gly Met Gln Leu Phe
            900                 905                 910
Gly Lys Ser Tyr Lys Asp Cys Val Cys Lys Ile Ala Ser Asp Cys Gln
```

```
                915                 920                 925
Leu Pro Arg Trp His Met Asn Asp Phe Phe His Ser Phe Leu Ile Val
        930                 935                 940
Phe Arg Val Leu Cys Gly Glu Trp Ile Glu Thr Met Trp Asp Cys Met
945                 950                 955                 960
Glu Val Ala Gly Gln Ala Met Cys Leu Thr Val Phe Met Met Val Met
                965                 970                 975
Val Ile Gly Asn Leu Val Leu Asn Leu Phe Leu Ala Leu Leu Leu
        980                 985                 990
Ser Ser Phe Ser Ala Asp Asn Leu  Ala Ala Thr Asp  Asp Asn Glu
        995                 1000                1005
Met Asn  Asn Leu Gln Ile Ala  Val Asp Arg Met His  Lys Gly Val
    1010                1015                1020
Ala Tyr  Val Lys Arg Lys Ile  Tyr Glu Phe Ile Gln  Gln Ser Phe
    1025                1030                1035
Ile Arg  Lys Gln Lys Ile Leu  Asp Glu Ile Lys Pro  Leu Asp Asp
    1040                1045                1050
Leu Asn  Asn Lys Lys Asp Ser  Cys Met Ser Asn His  Thr Ala Glu
    1055                1060                1065
Ile Gly  Lys Asp Leu Asp Tyr  Leu Lys Asp Val Asn  Gly Thr Thr
    1070                1075                1080
Ser Gly  Ile Gly Thr Gly Ser  Ser Val Glu Lys Tyr  Ile Ile Asp
    1085                1090                1095
Glu Ser  Asp Tyr Met Ser Phe  Ile Asn Asn Pro Ser  Leu Thr Val
    1100                1105                1110
Thr Val  Pro Ile Ala Val Gly  Glu Ser Asp Phe Glu  Asn Leu Asn
    1115                1120                1125
Thr Glu  Asp Phe Ser Ser Glu  Ser Asp Leu Glu Glu  Ser Lys Glu
    1130                1135                1140
Lys Leu  Asn Glu Ser Ser Ser  Ser Ser Glu Gly Ser  Thr Val Asp
    1145                1150                1155
Ile Gly  Ala Pro Val Glu Glu  Gln Pro Val Val Glu  Pro Glu Glu
    1160                1165                1170
Thr Leu  Glu Pro Glu Ala Cys  Phe Thr Glu Gly Cys  Val Gln Arg
    1175                1180                1185
Phe Lys  Cys Cys Gln Ile Asn  Val Glu Glu Gly Arg  Gly Lys Gln
    1190                1195                1200
Trp Trp  Asn Leu Arg Arg Thr  Cys Phe Arg Ile Val  Glu His Asn
    1205                1210                1215
Trp Phe  Glu Thr Phe Ile Val  Phe Met Ile Leu Leu  Ser Ser Gly
    1220                1225                1230
Ala Leu  Ala Phe Glu Asp Ile  Tyr Ile Asp Gln Arg  Lys Thr Ile
    1235                1240                1245
Lys Thr  Met Leu Glu Tyr Ala  Asp Lys Val Phe Thr  Tyr Ile Phe
    1250                1255                1260
Ile Leu  Glu Met Leu Leu Lys  Trp Val Ala Tyr Gly  Tyr Gln Thr
    1265                1270                1275
Tyr Phe  Thr Asn Ala Trp Cys  Trp Leu Asp Phe Leu  Ile Val Asp
    1280                1285                1290
Val Ser  Leu Val Ser Leu Thr  Ala Asn Ala Leu Gly  Tyr Ser Glu
    1295                1300                1305
Leu Gly  Ala Ile Lys Ser Leu  Arg Thr Leu Arg Ala  Leu Arg Pro
    1310                1315                1320
```

-continued

```
Leu Arg Ala Leu Ser Arg Phe Glu Gly Met Arg Val Val Val Asn
    1325                1330                1335

Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala Arg Trp Lys Asn Val Lys Val
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440

Ser Arg Asn Val Glu Leu Gln Pro Lys Tyr Glu Glu Ser Leu Tyr
    1445                1450                1455

Met Tyr Leu Tyr Phe Val Ile Phe Ile Ile Phe Gly Ser Phe Phe
    1460                1465                1470

Thr Leu Asn Leu Phe Ile Gly Val Ile Ile Asp Asn Phe Asn Gln
    1475                1480                1485

Gln Lys Lys Lys Phe Gly Gly Gln Asp Ile Phe Met Thr Glu Glu
    1490                1495                1500

Gln Lys Lys Tyr Tyr Asn Ala Met Lys Lys Leu Gly Ser Lys Lys
    1505                1510                1515

Pro Gln Lys Pro Ile Pro Arg Pro Gly Asn Lys Phe Gln Gly Met
    1520                1525                1530

Val Phe Asp Phe Val Thr Arg Gln Val Phe Asp Ile Ser Ile Met
    1535                1540                1545

Ile Leu Ile Cys Leu Asn Met Val Thr Met Met Val Glu Thr Asp
    1550                1555                1560

Asp Gln Ser Glu Tyr Val Thr Thr Ile Leu Ser Arg Ile Asn Leu
    1565                1570                1575

Val Phe Ile Val Leu Phe Thr Gly Glu Cys Val Leu Lys Leu Ile
    1580                1585                1590

Ser Leu Arg His Tyr Tyr Phe Thr Ile Gly Trp Asn Ile Phe Asp
    1595                1600                1605

Phe Val Val Val Ile Leu Ser Ile Val Gly Met Phe Leu Ala Glu
    1610                1615                1620

Leu Ile Glu Lys Tyr Phe Val Ser Pro Thr Leu Phe Arg Val Ile
    1625                1630                1635

Arg Leu Ala Arg Ile Gly Arg Ile Leu Arg Leu Ile Lys Gly Ala
    1640                1645                1650

Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710
```

-continued

```
Met Ile Cys Leu Phe Gln Ile Thr Thr Ser Ala Gly Trp Asp Gly
    1715                1720                1725

Leu Leu Ala Pro Ile Leu Asn Ser Lys Pro Pro Asp Cys Asp Pro
    1730                1735                1740

Asn Lys Val Asn Pro Gly Ser Ser Val Lys Gly Asp Cys Gly Asn
    1745                1750                1755

Pro Ser Val Gly Ile Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800

Asp Phe Glu Met Phe Tyr Glu Val Trp Glu Lys Phe Asp Pro Asp
    1805                1810                1815

Ala Thr Gln Phe Met Glu Phe Glu Lys Leu Ser Gln Phe Ala Ala
    1820                1825                1830

Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu Arg Phe
    1880                1885                1890

Met Ala Ser Asn Pro Ser Lys Val Ser Tyr Gln Pro Ile Thr Thr
    1895                1900                1905

Thr Leu Lys Arg Lys Gln Glu Glu Val Ser Ala Val Ile Ile Gln
    1910                1915                1920

Arg Ala Tyr Arg Arg His Leu Leu Lys Arg Thr Val Lys Gln Ala
    1925                1930                1935

Ser Phe Thr Tyr Asn Lys Asn Lys Ile Lys Gly Gly Ala Asn Leu
    1940                1945                1950

Leu Ile Lys Glu Asp Met Ile Ile Asp Arg Ile Asn Glu Asn Ser
    1955                1960                1965

Ile Thr Glu Lys Thr Asp Leu Thr Met Ser Thr Ala Ala Cys Pro
    1970                1975                1980

Pro Ser Tyr Asp Arg Val Thr Lys Pro Ile Val Glu Lys His Glu
    1985                1990                1995

Gln Glu Gly Lys Asp Glu Lys Ala Lys Gly Lys
    2000                2005
```

<210> SEQ ID NO 3
<211> LENGTH: 7027
<212> TYPE: DNA
<213> ORGANISM: Homo sapiens
<220> FEATURE:
<221> NAME/KEY: coding_region
<222> LOCATION: (1)..(6027)
<223> OTHER INFORMATION: encoded protein is identical to SEQ ID NO:2
<220> FEATURE:
<221> NAME/KEY: mutation
<222> LOCATION: (1206)..(1206)
<223> OTHER INFORMATION: t to c transition
<220> FEATURE:
<221> NAME/KEY: mutation
<222> LOCATION: (1209)..(1209)
<223> OTHER INFORMATION: t to c transition

<400> SEQUENCE: 3

```
atggagcaaa cagtgcttgt accaccagga cctgacagct tcaacttctt caccagagaa    60
tctcttgcgg ctattgaaag acgcattgca gaagaaaagg caaagaatcc caaaccagac   120
aaaaagatg acgacgaaaa tggcccaaag ccaaatagtg acttggaagc tggaaagaac    180
cttccattta tttatggaga cattcctcca gagatggtgt cagagcccct ggaggacctg   240
gaccctact atatcaataa gaaaactttt atagtattga ataaagggaa ggccatcttc    300
cggttcagtg ccacctctgc cctgtacatt ttaactccct tcaatcctct taggaaaata   360
gctattaaga ttttggtaca ttcattattc agcatgctaa ttatgtgcac tattttgaca   420
aactgtgtgt ttatgacaat gagtaaccct cctgattgga caaagaatgt agaatacacc   480
ttcacaggaa tatatacttt tgaatcactt ataaaaatta ttgcaagggg attctgttta   540
gaagatttta ctttccttcg ggatccatgg aactggctcg atttcactgt cattacattt   600
gcgtacgtca cagagtttgt ggacctgggc aatgtctcgg cattgagaac attcagagtt   660
ctccgagcat tgaagacgat ttcagtcatt ccaggcctga aaccattgt gggagccctg    720
atccagtctg tgaagaagct ctcagatgta atgatcctga ctgtgttctg tctgagcgta   780
tttgctctaa ttgggctgca gctgttcatg ggcaacctga ggaataaatg tatacaatgg   840
cctcccacca atgcttcctt ggaggaacat agtatagaaa agaatataac tgtgaattat   900
aatggtacac ttataaatga aactgtcttt gagtttgact ggaagtcata tattcaagat   960
tcaagatatc attatttcct ggagggtttt ttagatgcac tactatgtgg aaatagctct  1020
gatgcaggcc aatgtccaga gggatatatg tgtgtgaaag ctggtagaaa tcccaattat  1080
ggctacacaa gctttgatac cttcagttgg gctttttttgt ccttgtttcg actaatgact  1140
caggacttct gggaaaatct ttatcaactg acattacgtg ctgctgggaa aacgtacatg  1200
atattcttcg tattggtcat tttcttgggc tcattctacc taataaattt gatcctggct  1260
gtggtggcca tggcctacga ggaacagaat caggccacct ggaagaagc agaacagaaa  1320
gaggccgaat tcagcagat gattgaacag cttaaaaagc aacaggaggc agctcagcag  1380
gcagcaacgg caactgcctc agaacattcc agagagccca gtgcagcagg caggctctca  1440
gacagctcat ctgaagcctc taagttgagt tccaagagtg ctaaggaaag aagaaatcgg  1500
aggaagaaaa gaaaacagaa agagcagtct ggtggggaag agaaagatga ggatgaattc  1560
caaaaatctg aatctgagga cagcatcagg aggaaaggtt ttcgcttctc cattgaaggg  1620
aaccgattga catatgaaaa gaggtactcc tccccacacc agtctttgtt gagcatccgt  1680
ggctccctat tttcaccaag gcgaaatagc agaacaagcc ttttcagctt tagagggcga  1740
gcaaaggatg tgggatctga gaacgacttc gcagatgatg agcacagcac ctttgaggat  1800
aacgagagcc gtagagattc cttgtttgtg ccccgacgac acggagagag acgcaacagc  1860
aacctgagtc agaccagtag gtcatcccgg atgctggcag tgttccagc gaatgggaag  1920
atgcacagca ctgtggattg caatggtgtg gtttccttgg ttggtggacc ttcagttcct  1980
acatcgcctg ttggacagct tctgccagag gtgataatag ataagccagc tactgatgac  2040
aatggaacaa ccactgaaac tgaaatgaga agagaaggt caagttcttt ccacgtttcc  2100
atggactttc tagaagatcc ttcccaaagg caacgagcaa tgagtatagc cagcattcta  2160
acaaatacag tagaagaact tgaagaatcc aggcagaaat gcccaccctg ttggtataaa  2220
ttttccaaca tattcttaat ctgggactgt tctccatatt ggttaaaagt gaaacatgtt  2280
gtcaacctgg ttgtgatgga cccatttgtt gacctggcca tcaccatctg tattgtctta  2340
```

```
aatactctttt tcatggccat ggagcactat ccaatgacgg accatttcaa taatgtgctt   2400
acagtaggaa acttggtttt cactgggatc tttacagcag aaatgtttct gaaaattatt   2460
gccatggatc cttactatta tttccaagaa ggctggaata tctttgacgg ttttattgtg   2520
acgcttagcc tggtagaact tggactcgcc aatgtggaag gattatctgt tctccgttca   2580
tttcgattgc tgcgagtttt caagttggca aaatcttggc caacgttaaa tatgctaata   2640
aagatcatcg gcaattccgt gggggctctg ggaaatttaa ccctcgtctt ggccatcatc   2700
gtcttcattt tgccgtggt cggcatgcag ctctttggta aaagctacaa agattgtgtc   2760
tgcaagatcg ccagtgattg tcaactccca cgctggcaca tgaatgactt cttccactcc   2820
ttcctgattg tgttccgcgt gctgtgtggg gagtggatag agaccatgtg ggactgtatg   2880
gaggttgctg gtcaagccat gtgccttact gtcttcatga tggtcatggt gattggaaac   2940
ctagtggtcc tgaatctctt tctggccttg cttctgagct catttagtgc agacaacctt   3000
gcagccactg atgatgataa tgaaatgaat aatctccaaa ttgctgtgga taggatgcac   3060
aaaggagtag cttatgtgaa aagaaaaata tatgaattta ttcaacagtc cttcattagg   3120
aaacaaaaga ttttagatga aattaaacca cttgatgatc taaacaacaa gaaagacagt   3180
tgtatgtcca atcatacagc agaaattggg aaagatcttg actatcttaa agatgtaaat   3240
ggaactacaa gtggtatagg aactggcagc agtgttgaaa aatacattat tgatgaaagt   3300
gattacatgt cattcataaa caaccccagt cttactgtga ctgtaccaat tgctgtagga   3360
gaatctgact tgaaaatttt aaacacggaa gactttagta gtgaatcgga tctggaagaa   3420
agcaaagaga aactgaatga aagcagtagc tcatcagaag gtagcactgt ggacatcggc   3480
gcacctgtag aagaacagcc cgtagtggaa cctgaagaaa ctcttgaacc agaagcttgt   3540
ttcactgaag gctgtgtaca aagattcaag tgttgtcaaa tcaatgtgga agaaggcaga   3600
ggaaaacaat ggtggaacct gagaaggacg tgtttccgaa tagttgaaca taactggttt   3660
gagaccttca ttgttttcat gattctcctt agtagtggtg ctctggcatt tgaagatata   3720
tatattgatc agcgaaagac gattaagacg atgttggaat atgctgacaa ggttttcact   3780 tacatttca ttctggaaat gcttctaaaa tgggtggcat atggctatca aacatatttc   3840
accaatgcct ggtgttggct ggacttctta attgttgatg tttcattggt cagtttaaca   3900
gcaaatgcct tgggttactc agaacttgga gccatcaaat ctctcaggac actaagagct   3960
ctgagacctc taagagcctt atctcgattt gaagggatga gggtggttgt gaatgccctt   4020
ttaggagcaa ttccatccat catgaatgtg cttctggttt gtcttatatt ctggctaatt   4080
ttcagcatca tgggcgtaaa tttgtttgct ggcaaattct accactgtat taacaccaca   4140
actggtgaca ggtttgacat cgaagacgtg aataatcata ctgattgcct aaaactaata   4200
gaaagaaatg agactgctcg atggaaaaat gtgaaagtaa actttgataa tgtaggattt   4260
gggtatctct ctttgcttca agttgccaca ttcaaaggat ggatggatat aatgtatgca   4320
gcagttgatt ccagaaatgt ggaactccag cctaagtatg aagaaagtct gtacatgtat   4380
cttttacttg ttatttcat catctttggg tccttcttca ccttgaacct gtttattggt   4440
gtcatcatag ataatttcaa ccagcagaaa aagaagtttg gaggtcaaga catctttatg   4500
acagaagaac agaagaaata ctataatgca atgaaaaat taggatcgaa aaaaccgcaa   4560
aagcctatac ctcgaccagg aaacaaattt caaggaatgg tctttgactt cgtaaccaga   4620 caagttttg acataagcat catgattctc atctgtctta acatggtcac aatgatggtg   4680
gaaacagatg accagagtga atatgtgact accatttttgt cacgcatcaa tctggtgttc   4740
```

-continued

```
attgtgctat ttactggaga gtgtgtactg aaactcatct ctctacgcca ttattatttt    4800
accattggat ggaatatttt tgattttgtg gttgtcattc tctccattgt aggtatgttt    4860
cttgccgagc tgatagaaaa gtatttcgtg tcccctaccc tgttccgagt gatccgtctt    4920
gctaggattg gccgaatcct acgtctgatc aaaggagcaa agggatccg cacgctgctc    4980 tttgctttga tgatgtccct tcctgcgttg tttaacatcg gcctcctact cttcctagtc    5040
atgttcatct acgccatctt tgggatgtcc aactttgcct atgttaagag ggaagttggg    5100
atcgatgaca tgttcaactt tgagaccttt ggcaacagca tgatctgcct attccaaatt    5160
acaacctctg ctggctggga tggattgcta gcacccattc tcaacagtaa gccacccgac    5220 tgtgaccta ataaagttaa ccctggaagc tcagttaagg gagactgtgg gaacccatct    5280
gttggaattt tcttttttgt cagttacatc atcatatcct tcctggttgt ggtgaacatg    5340
tacatcgcgg tcatcctgga gaacttcagt gttgctactg aagaaagtgc agagcctctg    5400
agtgaggatg actttgagat gttctatgag gtttgggaga gtttgatcc cgatgcaact    5460 cagttcatgg aatttgaaaa attatctcag tttgcagctg cgcttgaacc gcctctcaat    5520
ctgccacaac caaacaaact ccagctcatt gccatggatt tgcccatggt gagtggtgac    5580
cggatccact gtcttgatat cttatttgct tttacaaagc gggttctagg agagagtgga    5640
gagatggatg ctctacgaat acagatggaa gagcgattca tggcttccaa tccttccaag    5700
gtctcctatc agccaatcac tactacttta aaacgaaaac aagaggaagt atctgctgtc    5760
attattcagc gtgcttacag acgccacctt ttaaagcgaa ctgtaaaaca gcttccttt    5820 acgtacaata aaaacaaaat caaaggtggg gctaatcttc ttataaaaga agacatgata    5880
attgacagaa taaatgaaaa ctctattaca gaaaaaactg atctgaccat gtccactgca    5940
gcttgtccac cttcctatga ccgggtgaca aagccaattg tggaaaaaca tgagcaagaa    6000
ggcaaagatg aaaaagccaa agggaaataa atgaaaataa ataaaaataa ttgggtgaca    6060
aattgtttac agcctgtgaa ggtgatgtat ttttatcaac aggactcctt taggaggtca    6120
atgccaaact gactgttttt acacaaatct ccttaaggtc agtgcctaca ataagacagt    6180 gacccttgt cagcaaactg tgactctgtg taaggggag atgaccttga caggaggtta    6240
ctgttctcac taccagctga cactgctgaa gataagatgc acaatggcta gtcagactgt    6300
agggaccagt ttcaaggggt gcaaacctgt gattttgggg ttgtttaaca tgaaacactt    6360
tagtgtagta attgtatcca ctgtttgcat ttcaactgcc acatttgtca cattttatg    6420 gaatctgtta gtggattcat cttttttgtta atccatgtgt ttattatatg tgactatttt    6480
tgtaaacgaa gtttctgttg agaaataggc taaggacctc tataacaggt atgccacctg    6540
gggggtatgg caaccacatg gccctcccag ctacacaaag tcgtggtttg catgagggca    6600
tgctgcactt agagatcatg catgagaaaa agtcacaaga aaaacaaatt cttaaatttc    6660
accatatttc tgggaggggt aattgggtga taagtggagg tgctttgttg atcttgtttt    6720
gcgaaatcca gccctagac caagtagatt atttgtgggt aggccagtaa atcttagcag    6780
gtgcaaactt cattcaaatg tttggagtca taaatgttat gtttctttt gttgtattaa    6840 aaaaaaacc tgaatagtga atattgcccc tcacctccca ccgccagaag actgaattga    6900
ccaaaattac tctttataaa tttctgcttt ttcctgcact tgtttagcc atcttcggct    6960 ctcagcaagg ttgacactgt atatgttaat gaaatgctat ttattatgta aatagtcatt    7020
ttaccct                                                             7027
```

<210> SEQ ID NO 4
<211> LENGTH: 1335
<212> TYPE: DNA
<213> ORGANISM: Homo sapiens
<220> FEATURE:
<221> NAME/KEY: CDS
<222> LOCATION: (25)..(681)

<400> SEQUENCE: 4

| | | | | | | | | | | | | | | | |
|---|---|---|---|---|---|---|---|---|---|---|---|---|---|---|---|
| atgcgcagca cgcgccgcgc agcc | atg | ggg | agg | ctg | ctg | gcc | tta | gtg | gtc | | | | | | 51 |
| | Met | Gly | Arg | Leu | Leu | Ala | Leu | Val | Val | | | | | | |
| | 1 | | | 5 | | | | | | | | | | | |

| ggc | gcg | gca | ctg | gtg | tcc | tca | gcc | tgc | ggg | ggc | tgc | gtg | gag | gtg | gac | 99 |
|---|---|---|---|---|---|---|---|---|---|---|---|---|---|---|---|---|
| Gly | Ala | Ala | Leu | Val | Ser | Ser | Ala | Cys | Gly | Gly | Cys | Val | Glu | Val | Asp | |
| 10 | | | | 15 | | | | | 20 | | | | | 25 | | |

| tcg | gag | acc | gag | gcc | gtg | tat | ggg | atg | acc | ttc | aaa | att | ctt | tgc | atc | 147 |
|---|---|---|---|---|---|---|---|---|---|---|---|---|---|---|---|---|
| Ser | Glu | Thr | Glu | Ala | Val | Tyr | Gly | Met | Thr | Phe | Lys | Ile | Leu | Cys | Ile | |
| | | | 30 | | | | | 35 | | | | | 40 | | | |

| tcc | tgc | aag | cgc | cgc | agc | gag | acc | aac | gct | gag | acc | ttc | acc | gag | tgg | 195 |
|---|---|---|---|---|---|---|---|---|---|---|---|---|---|---|---|---|
| Ser | Cys | Lys | Arg | Arg | Ser | Glu | Thr | Asn | Ala | Glu | Thr | Phe | Thr | Glu | Trp | |
| | | 45 | | | | | 50 | | | | | 55 | | | | |

| acc | ttc | cgc | cag | aag | ggc | act | gag | gag | ttt | gtc | aag | atc | ctg | cgc | tat | 243 |
|---|---|---|---|---|---|---|---|---|---|---|---|---|---|---|---|---|
| Thr | Phe | Arg | Gln | Lys | Gly | Thr | Glu | Glu | Phe | Val | Lys | Ile | Leu | Arg | Tyr | |
| | 60 | | | | | 65 | | | | | 70 | | | | | |

| gag | aat | gag | gtg | ttg | cag | ctg | gag | gag | gat | gag | cgc | ttc | gag | ggc | cgc | 291 |
|---|---|---|---|---|---|---|---|---|---|---|---|---|---|---|---|---|
| Glu | Asn | Glu | Val | Leu | Gln | Leu | Glu | Glu | Asp | Glu | Arg | Phe | Glu | Gly | Arg | |
| 75 | | | | | 80 | | | | | 85 | | | | | | |

| gtg | gtg | tgg | aat | ggc | agc | cgg | ggc | acc | aaa | gac | ctg | cag | gat | ctg | tct | 339 |
|---|---|---|---|---|---|---|---|---|---|---|---|---|---|---|---|---|
| Val | Val | Trp | Asn | Gly | Ser | Arg | Gly | Thr | Lys | Asp | Leu | Gln | Asp | Leu | Ser | |
| 90 | | | | 95 | | | | | 100 | | | | | 105 | | |

| atc | ttc | atc | acc | aat | gtc | acc | tac | aac | cac | tcg | ggc | gac | tac | gag | tgc | 387 |
|---|---|---|---|---|---|---|---|---|---|---|---|---|---|---|---|---|
| Ile | Phe | Ile | Thr | Asn | Val | Thr | Tyr | Asn | His | Ser | Gly | Asp | Tyr | Glu | Cys | |
| | | | 110 | | | | | 115 | | | | | 120 | | | |

| cac | gtc | tac | cgc | ctg | ctc | ttc | ttc | gaa | aac | tac | gag | cac | aac | acc | agc | 435 |
|---|---|---|---|---|---|---|---|---|---|---|---|---|---|---|---|---|
| His | Val | Tyr | Arg | Leu | Leu | Phe | Phe | Glu | Asn | Tyr | Glu | His | Asn | Thr | Ser | |
| | | 125 | | | | | 130 | | | | | 135 | | | | |

| gtc | gtc | aag | aag | atc | cac | att | gag | gta | gtg | gac | aaa | gcc | aac | aga | gac | 483 |
|---|---|---|---|---|---|---|---|---|---|---|---|---|---|---|---|---|
| Val | Val | Lys | Lys | Ile | His | Ile | Glu | Val | Val | Asp | Lys | Ala | Asn | Arg | Asp | |
| | 140 | | | | | 145 | | | | | 150 | | | | | |

| atg | gca | tcc | atc | gtg | tct | gag | atc | atg | atg | tat | gtg | ctc | att | gtg | gtg | 531 |
|---|---|---|---|---|---|---|---|---|---|---|---|---|---|---|---|---|
| Met | Ala | Ser | Ile | Val | Ser | Glu | Ile | Met | Met | Tyr | Val | Leu | Ile | Val | Val | |
| | 155 | | | | | 160 | | | | | 165 | | | | | |

| ttg | acc | ata | tgg | ctc | gtg | gca | gag | atg | att | tac | tgc | tac | aag | aag | atc | 579 |
|---|---|---|---|---|---|---|---|---|---|---|---|---|---|---|---|---|
| Leu | Thr | Ile | Trp | Leu | Val | Ala | Glu | Met | Ile | Tyr | Cys | Tyr | Lys | Lys | Ile | |
| 170 | | | | 175 | | | | | 180 | | | | | 185 | | |

| gct | gcc | gcc | acg | gag | act | gct | gca | cag | gag | aat | gcc | tcg | gaa | tac | ctg | 627 |
|---|---|---|---|---|---|---|---|---|---|---|---|---|---|---|---|---|
| Ala | Ala | Ala | Thr | Glu | Thr | Ala | Ala | Gln | Glu | Asn | Ala | Ser | Glu | Tyr | Leu | |
| | | | 190 | | | | | 195 | | | | | 200 | | | |

| gcc | atc | acc | tct | gaa | agc | aaa | gag | aac | tgc | acg | ggc | gtc | cag | gtg | gcc | 675 |
|---|---|---|---|---|---|---|---|---|---|---|---|---|---|---|---|---|
| Ala | Ile | Thr | Ser | Glu | Ser | Lys | Glu | Asn | Cys | Thr | Gly | Val | Gln | Val | Ala | |
| | | | 205 | | | | | 210 | | | | | 215 | | | |

| gaa | tag | ccctggccct | gggccccgcc | tcaaggaaga | gccagccgta | atggggactc | | | | | | | | | | 731 |
|---|---|---|---|---|---|---|---|---|---|---|---|---|---|---|---|---|
| Glu | | | | | | | | | | | | | | | | | tccaggcacc gcctgccccc agcgtggggg tggccactcc tgggcccag aaagcctcag          791 agtccctgcc gacggagcca ctgggtgtgg aggggcagg gggcttggct cgcaccccca          851 ctttcgcctc ctccagctcc tgccccgccg ccgcgcacc gccatgcatg atgggtaaag          911 caatactgcc gctgccccca ccctgcttct gctgcctgtt tggggagggg ggcggtgagg          971 tgggcagcgg ccccgcaccc ctcctccttg ctcatttgca cacattggcc gcttcagaca         1031

-continued

```
cgcacttctg gggccagccc ctccccgcct cctccctgcc tggcggcagg ggtcgcgatg    1091
atgggctgga gcagtttggg gcaggggtt ctgggaccca ctccgactcc ccctccccgg     1151
catcatttcc cctcccgctt ctccggctga cctggggtcc cccctccctg taatgcactc    1211
ctgccccggc ccaacctcgc cctctctcac cagccttgaa ctgtggccac ctagaaaggg    1271
gcccattcag cctcgtctct ttacagaagt agttttgttc atgaaataaa gactcttgga    1331
cttg                                                                1335
```

<210> SEQ ID NO 5
<211> LENGTH: 218
<212> TYPE: PRT
<213> ORGANISM: Homo sapiens

<400> SEQUENCE: 5

```
Met Gly Arg Leu Leu Ala Leu Val Val Gly Ala Leu Val Ser Ser
1               5                   10                  15

Ala Cys Gly Gly Cys Val Glu Val Asp Ser Glu Thr Glu Ala Val Tyr
            20                  25                  30

Gly Met Thr Phe Lys Ile Leu Cys Ile Ser Cys Lys Arg Arg Ser Glu
        35                  40                  45

Thr Asn Ala Glu Thr Phe Thr Glu Trp Thr Phe Arg Gln Lys Gly Thr
    50                  55                  60

Glu Glu Phe Val Lys Ile Leu Arg Tyr Glu Asn Glu Val Leu Gln Leu
65                  70                  75                  80

Glu Glu Asp Glu Arg Phe Glu Gly Arg Val Trp Asn Gly Ser Arg
                85                  90                  95

Gly Thr Lys Asp Leu Gln Asp Leu Ser Ile Phe Ile Thr Asn Val Thr
            100                 105                 110

Tyr Asn His Ser Gly Asp Tyr Glu Cys His Val Tyr Arg Leu Leu Phe
        115                 120                 125

Phe Glu Asn Tyr Glu His Asn Thr Ser Val Val Lys Lys Ile His Ile
    130                 135                 140

Glu Val Val Asp Lys Ala Asn Arg Asp Met Ala Ser Ile Val Ser Glu
145                 150                 155                 160

Ile Met Met Tyr Val Leu Ile Val Val Leu Thr Ile Trp Leu Val Ala
                165                 170                 175

Glu Met Ile Tyr Cys Tyr Lys Lys Ile Ala Ala Ala Thr Glu Thr Ala
            180                 185                 190

Ala Gln Glu Asn Ala Ser Glu Tyr Leu Ala Ile Thr Ser Glu Ser Lys
        195                 200                 205

Glu Asn Cys Thr Gly Val Gln Val Ala Glu
    210                 215
```

<210> SEQ ID NO 6
<211> LENGTH: 648
<212> TYPE: DNA
<213> ORGANISM: Homo sapiens
<220> FEATURE:
<221> NAME/KEY: CDS
<222> LOCATION: (1)..(648)

<400> SEQUENCE: 6

```
atg cac aga gat gcc tgg cta cct cgc cct gcc ttc agc ctc acg ggg    48
Met His Arg Asp Ala Trp Leu Pro Arg Pro Ala Phe Ser Leu Thr Gly
1               5                   10                  15 ctc agt ctc ttt ttc tct ttg gtg cca cca gga cgg agc atg gag gtc    96
```

|  |  |  |  |  |  |  |  |  |  |  |  |  |  |  |  |
|---|---|---|---|---|---|---|---|---|---|---|---|---|---|---|---|

```
Leu Ser Leu Phe Phe Ser Leu Val Pro Pro Gly Arg Ser Met Glu Val
         20                  25                  30 aca gta cct gcc acc ctc aac gtc ctc aat ggc tct gac gcc cgc ctg       144
Thr Val Pro Ala Thr Leu Asn Val Leu Asn Gly Ser Asp Ala Arg Leu
         35                  40                  45 ccc tgc acc ttc aac tcc tgc tac aca gtg aac cac aaa cag ttc tcc       192
Pro Cys Thr Phe Asn Ser Cys Tyr Thr Val Asn His Lys Gln Phe Ser
 50                  55                  60 ctg aac tgg act tac cag gag tgc aac aac tgc tct gag gag atg ttc       240
Leu Asn Trp Thr Tyr Gln Glu Cys Asn Asn Cys Ser Glu Glu Met Phe
 65                  70                  75                  80 ctc cag ttc cgc atg aag atc att aac ctg aag ctg gag cgg ttt caa       288
Leu Gln Phe Arg Met Lys Ile Ile Asn Leu Lys Leu Glu Arg Phe Gln
                 85                  90                  95 gac cgc gtg gag ttc tca ggg aac ccc agc aag tac gat gtg tcg gtg       336
Asp Arg Val Glu Phe Ser Gly Asn Pro Ser Lys Tyr Asp Val Ser Val
             100                 105                 110 atg ctg aga aac gtg cag ccg gag gat gag ggg att tac aac tgc tac       384
Met Leu Arg Asn Val Gln Pro Glu Asp Glu Gly Ile Tyr Asn Cys Tyr
             115                 120                 125 atc atg aac ccc cct gac cgc cac cgt ggc cat ggc aag atc cat ctg       432
Ile Met Asn Pro Pro Asp Arg His Arg Gly His Gly Lys Ile His Leu
 130                 135                 140 cag gtc ctc atg gaa gag ccc cct gag cgg gac tcc acg gtg gcc gtg       480
Gln Val Leu Met Glu Glu Pro Pro Glu Arg Asp Ser Thr Val Ala Val
 145                 150                 155                 160 att gtg ggt gcc tcc gtc ggg ggc ttc ctg gct gtg gtc atc ttg gtg       528
Ile Val Gly Ala Ser Val Gly Gly Phe Leu Ala Val Val Ile Leu Val
                 165                 170                 175 ctg atg gtg gtc aag tgt gtg agg aga aaa aaa gag cag aag ctg agc       576
Leu Met Val Val Lys Cys Val Arg Arg Lys Lys Glu Gln Lys Leu Ser
             180                 185                 190 aca gat gac ctg aag acc gag gag gag ggc aag acg gac ggt gaa ggc       624
Thr Asp Asp Leu Lys Thr Glu Glu Glu Gly Lys Thr Asp Gly Glu Gly
             195                 200                 205 aac ccg gat gat ggc gcc aag tag                                       648
Asn Pro Asp Asp Gly Ala Lys
 210                 215

<210> SEQ ID NO 7
<211> LENGTH: 215
<212> TYPE: PRT
<213> ORGANISM: Homo sapiens

<400> SEQUENCE: 7

Met His Arg Asp Ala Trp Leu Pro Arg Pro Ala Phe Ser Leu Thr Gly
 1               5                  10                  15

Leu Ser Leu Phe Phe Ser Leu Val Pro Pro Gly Arg Ser Met Glu Val
             20                  25                  30

Thr Val Pro Ala Thr Leu Asn Val Leu Asn Gly Ser Asp Ala Arg Leu
         35                  40                  45

Pro Cys Thr Phe Asn Ser Cys Tyr Thr Val Asn His Lys Gln Phe Ser
 50                  55                  60

Leu Asn Trp Thr Tyr Gln Glu Cys Asn Asn Cys Ser Glu Glu Met Phe
 65                  70                  75                  80

Leu Gln Phe Arg Met Lys Ile Ile Asn Leu Lys Leu Glu Arg Phe Gln
                 85                  90                  95

Asp Arg Val Glu Phe Ser Gly Asn Pro Ser Lys Tyr Asp Val Ser Val
             100                 105                 110
```

```
Met Leu Arg Asn Val Gln Pro Glu Asp Glu Gly Ile Tyr Asn Cys Tyr
            115                 120                 125
Ile Met Asn Pro Pro Asp Arg His Arg Gly His Gly Lys Ile His Leu
        130                 135                 140
Gln Val Leu Met Glu Glu Pro Pro Glu Arg Asp Ser Thr Val Ala Val
145                 150                 155                 160
Ile Val Gly Ala Ser Val Gly Gly Phe Leu Ala Val Ile Leu Val
                165                 170                 175
Leu Met Val Val Lys Cys Val Arg Arg Lys Lys Glu Gln Lys Leu Ser
            180                 185                 190
Thr Asp Asp Leu Lys Thr Glu Glu Gly Lys Thr Asp Gly Glu Gly
        195                 200                 205
Asn Pro Asp Asp Gly Ala Lys
        210                 215
```

<210> SEQ ID NO 8
<211> LENGTH: 1261
<212> TYPE: DNA
<213> ORGANISM: Homo sapiens
<220> FEATURE:
<221> NAME/KEY: CDS
<222> LOCATION: (376)..(1023)

<400> SEQUENCE: 8

```
ccctcccttc cgagctgagc ttaccctggg cgcaaacgag cgaggcaggg gcgcgagtgg      60
aagctggagt tccggggtgg gcggggaggc gactgtccgt ggtgctgagc gccggcgaga     120
gcgggcgcgg agcggctgat cggctccctc gaactgggga ggtccagtgg ggtcgcttag     180
ggcccaaagc ccccacccgg ctccaaaagc tcccagggcc tccccaggca ccggtgctcg     240
gcccttcctt cggtcagaaa gtcgcccccct gggggcagtt cgtcccaaag ggtttcctcg     300
aaagaatctg agagggcgca gtccttgacc gagggaatct ctctgtgtag ccttggaagc     360
cgccagcccc agaag atg cct gcc ttc aat aga ttg ttt ccc ctg gct tct      411
                Met Pro Ala Phe Asn Arg Leu Phe Pro Leu Ala Ser
                  1               5                  10 ctc gtg ctt atc tac tgg gtc agt gtc tgc ttc cct gtg tgt gtg gaa       459
Leu Val Leu Ile Tyr Trp Val Ser Val Cys Phe Pro Val Cys Val Glu
            15                  20                  25 gtg ccc tcg gag acg gag gcc gtg cag ggc aac ccc atg aag ctg cgc       507
Val Pro Ser Glu Thr Glu Ala Val Gln Gly Asn Pro Met Lys Leu Arg
        30                  35                  40 tgc atc tcc tgc atg aag aga gag gag gtg gag gcc acc acg gtg gtg       555
Cys Ile Ser Cys Met Lys Arg Glu Glu Val Glu Ala Thr Thr Val Val
 45                  50                  55                  60 gaa tgg ttc tac agg ccc gag ggc ggt aaa gat ttc ctt att tac gag       603
Glu Trp Phe Tyr Arg Pro Glu Gly Gly Lys Asp Phe Leu Ile Tyr Glu
                65                  70                  75 tat cgg aat ggc cac cag gag gtg gag agc ccc ttt cag ggg cgc ctg       651
Tyr Arg Asn Gly His Gln Glu Val Glu Ser Pro Phe Gln Gly Arg Leu
            80                  85                  90 cag tgg aat ggc agc aag gac ctg cag gac gtg tcc atc act gtg ctc       699
Gln Trp Asn Gly Ser Lys Asp Leu Gln Asp Val Ser Ile Thr Val Leu
        95                 100                 105 aac gtc act ctg aac gac tct ggc ctc tac acc tgc aat gtg tcc cgg       747
Asn Val Thr Leu Asn Asp Ser Gly Leu Tyr Thr Cys Asn Val Ser Arg
    110                 115                 120 gag ttt gag ttt gag gcg cat cgg ccc ttt gtg aag acg acg cgg ctg       795
Glu Phe Glu Phe Glu Ala His Arg Pro Phe Val Lys Thr Thr Arg Leu
```

-continued

| | | | | | | | | | | | | | | | |
|---|---|---|---|---|---|---|---|---|---|---|---|---|---|---|---|
| 125 | | | | 130 | | | | 135 | | | | 140 | | | |

```
atc ccc cta aga gtc acc gag gag gct gga gag gac ttc acc tct gtg     843
Ile Pro Leu Arg Val Thr Glu Glu Ala Gly Glu Asp Phe Thr Ser Val
            145                 150                 155 gtc tca gaa atc atg atg tac atc ctt ctg gtc ttc ctc acc ctg tgg     891
Val Ser Glu Ile Met Met Tyr Ile Leu Leu Val Phe Leu Thr Leu Trp
        160                 165                 170 ctg ctc atc gag atg ata tat tgc tac aga aag gtc tca aaa gcc gaa     939
Leu Leu Ile Glu Met Ile Tyr Cys Tyr Arg Lys Val Ser Lys Ala Glu
    175                 180                 185 gag gca gcc caa gaa aac gcg tct gac tac ctt gcc atc cca tct gag     987
Glu Ala Ala Gln Glu Asn Ala Ser Asp Tyr Leu Ala Ile Pro Ser Glu
190                 195                 200 aac aag gag aac tct gcg gta cca gtg gag gaa tag aacaggagca         1033
Asn Lys Glu Asn Ser Ala Val Pro Val Glu Glu
205                 210                 215 gtgtgacatg aggtggcctg aacacctgag ggactggaca tcccatgttc agcaatgtca  1093
atggcatcag gagggcgccc caagggcccc atcgcttccc ttcatgcatc cattgttctg  1153
ttcattcatt catccataca tccacctgcc tctgagcttt cacctctgac tccctaactc  1213
catcagacct ctacgcacca taagactctg ccagaactga gaagccgg               1261

<210> SEQ ID NO 9
<211> LENGTH: 215
<212> TYPE: PRT
<213> ORGANISM: Homo sapiens

<400> SEQUENCE: 9

Met Pro Ala Phe Asn Arg Leu Phe Pro Leu Ala Ser Leu Val Leu Ile
1               5                   10                  15

Tyr Trp Val Ser Val Cys Phe Pro Val Cys Val Glu Val Pro Ser Glu
            20                  25                  30

Thr Glu Ala Val Gln Gly Asn Pro Met Lys Leu Arg Cys Ile Ser Cys
        35                  40                  45

Met Lys Arg Glu Glu Val Glu Ala Thr Thr Val Val Glu Trp Phe Tyr
    50                  55                  60

Arg Pro Glu Gly Gly Lys Asp Phe Leu Ile Tyr Glu Tyr Arg Asn Gly
65                  70                  75                  80

His Gln Glu Val Glu Ser Pro Phe Gln Gly Arg Leu Gln Trp Asn Gly
                85                  90                  95

Ser Lys Asp Leu Gln Asp Val Ser Ile Thr Val Leu Asn Val Thr Leu
            100                 105                 110

Asn Asp Ser Gly Leu Tyr Thr Cys Asn Val Ser Arg Glu Phe Glu Phe
        115                 120                 125

Glu Ala His Arg Pro Phe Val Lys Thr Thr Arg Leu Ile Pro Leu Arg
    130                 135                 140

Val Thr Glu Glu Ala Gly Glu Asp Phe Thr Ser Val Val Ser Glu Ile
145                 150                 155                 160

Met Met Tyr Ile Leu Leu Val Phe Leu Thr Leu Trp Leu Leu Ile Glu
                165                 170                 175

Met Ile Tyr Cys Tyr Arg Lys Val Ser Lys Ala Glu Ala Ala Gln
            180                 185                 190

Glu Asn Ala Ser Asp Tyr Leu Ala Ile Pro Ser Glu Asn Lys Glu Asn
        195                 200                 205

Ser Ala Val Pro Val Glu Glu
    210                 215
```

```
<210> SEQ ID NO 10
<211> LENGTH: 39
<212> TYPE: DNA
<213> ORGANISM: Artificial Sequence
<220> FEATURE:
<223> OTHER INFORMATION: PCR primer AF having A-overhang-enhancing
      sequence at 5' end

<400> SEQUENCE: 10
gtttcttgcg gccgcatgga gcaaacagtg cttgtacca                     39

<210> SEQ ID NO 11
<211> LENGTH: 27
<212> TYPE: DNA
<213> ORGANISM: Artificial Sequence
<220> FEATURE:
<223> OTHER INFORMATION: PCR primer AR having A-overhang-enhancing
      sequence at 5' end

<400> SEQUENCE: 11
gtgtctttcc cttcaatgga gaagcga                                  27

<210> SEQ ID NO 12
<211> LENGTH: 25
<212> TYPE: DNA
<213> ORGANISM: Artificial Sequence
<220> FEATURE:
<223> OTHER INFORMATION: PCR primer BF having A-overhang-enhancing
      sequence at 5' end

<400> SEQUENCE: 12
gtttcttctg gtggggaaga gaaag                                    25

<210> SEQ ID NO 13
<211> LENGTH: 31
<212> TYPE: DNA
<213> ORGANISM: Artificial Sequence
<220> FEATURE:
<223> OTHER INFORMATION: PCR primer BR having A-overhang-enhancing
      sequence at 5' end

<400> SEQUENCE: 13
gtgtcttcta taccacttgt agttccattt a                             31

<210> SEQ ID NO 14
<211> LENGTH: 28
<212> TYPE: DNA
<213> ORGANISM: Artificial Sequence
<220> FEATURE:
<223> OTHER INFORMATION: PCR primer CF having A-overhang-enhancing
      sequence at 5' end

<400> SEQUENCE: 14
gtttctttat gtccaatcat acagcaga                                 28

<210> SEQ ID NO 15
<211> LENGTH: 27
<212> TYPE: DNA
<213> ORGANISM: Artificial Sequence
<220> FEATURE:
<223> OTHER INFORMATION: PCR primer CR having A-overhang-enhancing
      sequence at 5' end

<400> SEQUENCE: 15
gtgtcttggc ttactgttga gaatggg                                  27
```

<210> SEQ ID NO 16
<211> LENGTH: 27
<212> TYPE: DNA
<213> ORGANISM: Artificial Sequence
<220> FEATURE:
<223> OTHER INFORMATION: PCR primer DF having A-overhang-enhancing
      sequence at 5' end

<400> SEQUENCE: 16
gtttcttacg ccattattat tttacca                                          27

<210> SEQ ID NO 17
<211> LENGTH: 33
<212> TYPE: DNA
<213> ORGANISM: Artificial Sequence
<220> FEATURE:
<223> OTHER INFORMATION: PCR primer DR having A-overhang-enhancing
      sequence at 5' end

<400> SEQUENCE: 17
gtgtcttgtc gactcaaggt catctcccct tta                                   33

<210> SEQ ID NO 18
<211> LENGTH: 7
<212> TYPE: DNA
<213> ORGANISM: Artificial Sequence
<220> FEATURE:
<223> OTHER INFORMATION: 5' Sequence added to forward primers to enhance
      generation of A-overhangs by Taq polymerase

<400> SEQUENCE: 18 gtttctt                                                                 7

<210> SEQ ID NO 19
<211> LENGTH: 7
<212> TYPE: DNA
<213> ORGANISM: Artificial Sequence
<220> FEATURE:
<223> OTHER INFORMATION: 5' sequence added to reverse primers to enhance
      generation of A-overhangs by Taq polymerase

<400> SEQUENCE: 19 gtgtctt                                                                 7

<210> SEQ ID NO 20
<211> LENGTH: 5997
<212> TYPE: DNA
<213> ORGANISM: Homo sapiens
<220> FEATURE:
<221> NAME/KEY: CDS
<222> LOCATION: (1)..(5997)

<400> SEQUENCE: 20 atg gag caa aca gtg ctt gta cca cca gga cct gac agc ttc aac ttc         48
Met Glu Gln Thr Val Leu Val Pro Pro Gly Pro Asp Ser Phe Asn Phe
1               5                   10                  15 ttc acc aga gaa tct ctt gcg gct att gaa aga cgc att gca gaa gaa         96
Phe Thr Arg Glu Ser Leu Ala Ala Ile Glu Arg Arg Ile Ala Glu Glu
            20                  25                  30 aag gca aag aat ccc aaa cca gac aaa aaa gat gac gac gaa aat ggc        144
Lys Ala Lys Asn Pro Lys Pro Asp Lys Lys Asp Asp Asp Glu Asn Gly
        35                  40                  45 cca aag cca aat agt gac ttg gaa gct gga aag aac ctt cca ttt att        192
Pro Lys Pro Asn Ser Asp Leu Glu Ala Gly Lys Asn Leu Pro Phe Ile
    50                  55                  60

```
                                                        -continued tat gga gac att cct cca gag atg gtg tca gag ccc ctg gag gac ctg      240
Tyr Gly Asp Ile Pro Pro Glu Met Val Ser Glu Pro Leu Glu Asp Leu
 65                  70                  75                  80 gac ccc tac tat atc aat aag aaa act ttt ata gta ttg aat aaa ggg      288
Asp Pro Tyr Tyr Ile Asn Lys Lys Thr Phe Ile Val Leu Asn Lys Gly
                     85                  90                  95 aag gcc atc ttc cgg ttc agt gcc acc tct gcc ctg tac att tta act      336
Lys Ala Ile Phe Arg Phe Ser Ala Thr Ser Ala Leu Tyr Ile Leu Thr
                100                 105                 110 ccc ttc aat cct ctt agg aaa ata gct att aag att ttg gta cat tca      384
Pro Phe Asn Pro Leu Arg Lys Ile Ala Ile Lys Ile Leu Val His Ser
            115                 120                 125 tta ttc agc atg cta att atg tgc act att ttg aca aac tgt gtg ttt      432
Leu Phe Ser Met Leu Ile Met Cys Thr Ile Leu Thr Asn Cys Val Phe
130                 135                 140 atg aca atg agt aac cct cct gat tgg aca aag aat gta gaa tac acc      480
Met Thr Met Ser Asn Pro Pro Asp Trp Thr Lys Asn Val Glu Tyr Thr
145                 150                 155                 160 ttc aca gga ata tat act ttt gaa tca ctt ata aaa att att gca agg      528
Phe Thr Gly Ile Tyr Thr Phe Glu Ser Leu Ile Lys Ile Ile Ala Arg
                165                 170                 175 gga ttc tgt tta gaa gat ttt act ttc ctt cgg gat cca tgg aac tgg      576
Gly Phe Cys Leu Glu Asp Phe Thr Phe Leu Arg Asp Pro Trp Asn Trp
            180                 185                 190 ctc gat ttc act gtc att aca ttt gcg tac gtc aca gag ttt gtg gac      624
Leu Asp Phe Thr Val Ile Thr Phe Ala Tyr Val Thr Glu Phe Val Asp
        195                 200                 205 ctg ggc aat gtc tcg gca ttg aga aca ttc aga gtt ctc cga gca ttg      672
Leu Gly Asn Val Ser Ala Leu Arg Thr Phe Arg Val Leu Arg Ala Leu
    210                 215                 220 aag acg att tca gtc att cca ggc ctg aaa acc att gtg gga gcc ctg      720
Lys Thr Ile Ser Val Ile Pro Gly Leu Lys Thr Ile Val Gly Ala Leu
225                 230                 235                 240 atc cag tct gtg aag aag ctc tca gat gta atg atc ctg act gtg ttc      768
Ile Gln Ser Val Lys Lys Leu Ser Asp Val Met Ile Leu Thr Val Phe
                245                 250                 255 tgt ctg agc gta ttt gct cta att ggg ctg cag ctg ttc atg ggc aac      816
Cys Leu Ser Val Phe Ala Leu Ile Gly Leu Gln Leu Phe Met Gly Asn
            260                 265                 270 ctg agg aat aaa tgt ata caa tgg cct ccc acc aat gct tcc ttg gag      864
Leu Arg Asn Lys Cys Ile Gln Trp Pro Pro Thr Asn Ala Ser Leu Glu
        275                 280                 285 gaa cat agt ata gaa aag aat ata act gtg aat tat aat ggt aca ctt      912
Glu His Ser Ile Glu Lys Asn Ile Thr Val Asn Tyr Asn Gly Thr Leu
    290                 295                 300 ata aat gaa act gtc ttt gag ttt gac tgg aag tca tat att caa gat      960
Ile Asn Glu Thr Val Phe Glu Phe Asp Trp Lys Ser Tyr Ile Gln Asp
305                 310                 315                 320 tca aga tat cat tat ttc ctg gag ggt ttt tta gat gca cta cta tgt     1008
Ser Arg Tyr His Tyr Phe Leu Glu Gly Phe Leu Asp Ala Leu Leu Cys
                325                 330                 335 gga aat agc tct gat gca ggc caa tgt cca gag gga tat atg tgt gtg     1056
Gly Asn Ser Ser Asp Ala Gly Gln Cys Pro Glu Gly Tyr Met Cys Val
            340                 345                 350 aaa gct ggt aga aat ccc aat tat ggc tac aca agc ttt gat acc ttc     1104
Lys Ala Gly Arg Asn Pro Asn Tyr Gly Tyr Thr Ser Phe Asp Thr Phe
        355                 360                 365 agt tgg gct ttt ttg tcc ttg ttt cga cta atg act cag gac ttc tgg     1152
Ser Trp Ala Phe Leu Ser Leu Phe Arg Leu Met Thr Gln Asp Phe Trp
    370                 375                 380
```

```
                                                              -continued gaa aat ctt tat caa ctg aca tta cgt gct gct ggg aaa acg tac atg    1200
Glu Asn Leu Tyr Gln Leu Thr Leu Arg Ala Ala Gly Lys Thr Tyr Met
385                 390                 395                 400 ata ttt ttt gta ttg gtc att ttc ttg ggc tca ttc tac cta ata aat    1248
Ile Phe Phe Val Leu Val Ile Phe Leu Gly Ser Phe Tyr Leu Ile Asn
            405                 410                 415 ttg atc ctg gct gtg gtg gcc atg gcc tac gag gaa cag aat cag gcc    1296
Leu Ile Leu Ala Val Val Ala Met Ala Tyr Glu Glu Gln Asn Gln Ala
420                 425                 430 acc ttg gaa gaa gca gaa cag aaa gag gcc gaa ttt cag cag atg att    1344
Thr Leu Glu Glu Ala Glu Gln Lys Glu Ala Glu Phe Gln Gln Met Ile
    435                 440                 445 gaa cag ctt aaa aag caa cag gag gca gct cag cag gca gca acg gca    1392
Glu Gln Leu Lys Lys Gln Gln Glu Ala Ala Gln Gln Ala Ala Thr Ala
450                 455                 460 act gcc tca gaa cat tcc aga gag ccc agt gca gca ggc agg ctc tca    1440
Thr Ala Ser Glu His Ser Arg Glu Pro Ser Ala Ala Gly Arg Leu Ser
465                 470                 475                 480 gac agc tca tct gaa gcc tct aag ttg agt tcc aag agt gct aag gaa    1488
Asp Ser Ser Ser Glu Ala Ser Lys Leu Ser Ser Lys Ser Ala Lys Glu
                485                 490                 495 aga aga aat cgg agg aag aaa aga aaa cag aaa gag cag tct ggt ggg    1536
Arg Arg Asn Arg Arg Lys Lys Arg Lys Gln Lys Glu Gln Ser Gly Gly
            500                 505                 510 gaa gag aaa gat gag gat gaa ttc caa aaa tct gaa tct gag gac agc    1584
Glu Glu Lys Asp Glu Asp Glu Phe Gln Lys Ser Glu Ser Glu Asp Ser
        515                 520                 525 atc agg agg aaa ggt ttt cgc ttc tcc att gaa ggg aac cga ttg aca    1632
Ile Arg Arg Lys Gly Phe Arg Phe Ser Ile Glu Gly Asn Arg Leu Thr
    530                 535                 540 tat gaa aag agg tac tcc tcc cca cac cag tct ttg ttg agc atc cgt    1680
Tyr Glu Lys Arg Tyr Ser Ser Pro His Gln Ser Leu Leu Ser Ile Arg
545                 550                 555                 560 ggc tcc cta ttt tca cca agg cga aat agc aga aca agc ctt ttc agc    1728
Gly Ser Leu Phe Ser Pro Arg Arg Asn Ser Arg Thr Ser Leu Phe Ser
                565                 570                 575 ttt aga ggg cga gca aag gat gtg gga tct gag aac gac ttc gca gat    1776
Phe Arg Gly Arg Ala Lys Asp Val Gly Ser Glu Asn Asp Phe Ala Asp
            580                 585                 590 gat gag cac agc acc ttt gag gat aac gag agc cgt aga gat tcc ttg    1824
Asp Glu His Ser Thr Phe Glu Asp Asn Glu Ser Arg Arg Asp Ser Leu
        595                 600                 605 ttt gtg ccc cga cga cac gga gag aga cgc aac agc aac ctg agt cag    1872
Phe Val Pro Arg Arg His Gly Glu Arg Arg Asn Ser Asn Leu Ser Gln
    610                 615                 620 acc agt agg tca tcc cgg atg ctg gca gtg ttt cca gcg aat ggg aag    1920
Thr Ser Arg Ser Ser Arg Met Leu Ala Val Phe Pro Ala Asn Gly Lys
625                 630                 635                 640 atg cac agc act gtg gat tgc aat ggt gtg gtt tcc ttg gtt ggt gga    1968
Met His Ser Thr Val Asp Cys Asn Gly Val Val Ser Leu Val Gly Gly
                645                 650                 655 cct tca gtt cct aca tcg cct gtt gga cag ctt ctg cca gag gga aca    2016
Pro Ser Val Pro Thr Ser Pro Val Gly Gln Leu Leu Pro Glu Gly Thr
            660                 665                 670 acc act gaa act gaa atg aga aag aga agg tca agt tct ttc cac gtt    2064
Thr Thr Glu Thr Glu Met Arg Lys Arg Arg Ser Ser Ser Phe His Val
        675                 680                 685 tcc atg gac ttt cta gaa gat cct tcc caa agg caa cga gca atg agt    2112
Ser Met Asp Phe Leu Glu Asp Pro Ser Gln Arg Gln Arg Ala Met Ser
```

```
                690                 695                 700
ata gcc agc att cta aca aat aca gta gaa gaa ctt gaa gaa tcc agg      2160
Ile Ala Ser Ile Leu Thr Asn Thr Val Glu Glu Leu Glu Glu Ser Arg
705                 710                 715                 720 cag aaa tgc cca ccc tgt tgg tat aaa ttt tcc aac ata ttc tta atc      2208
Gln Lys Cys Pro Pro Cys Trp Tyr Lys Phe Ser Asn Ile Phe Leu Ile
                725                 730                 735 tgg gac tgt tct cca tat tgg tta aaa gtg aaa cat gtt gtc aac ctg      2256
Trp Asp Cys Ser Pro Tyr Trp Leu Lys Val Lys His Val Val Asn Leu
            740                 745                 750 gtt gtg atg gac cca ttt gtt gac ctg gcc atc acc atc tgt att gtc      2304
Val Val Met Asp Pro Phe Val Asp Leu Ala Ile Thr Ile Cys Ile Val
        755                 760                 765 tta aat act ctt ttc atg gcc atg gag cac tat cca atg acg gac cat      2352
Leu Asn Thr Leu Phe Met Ala Met Glu His Tyr Pro Met Thr Asp His
    770                 775                 780 ttc aat aat gtg ctt aca gta gga aac ttg gtt ttc act ggg atc ttt      2400
Phe Asn Asn Val Leu Thr Val Gly Asn Leu Val Phe Thr Gly Ile Phe
785                 790                 795                 800 aca gca gaa atg ttt ctg aaa att att gcc atg gat cct tac tat tat      2448
Thr Ala Glu Met Phe Leu Lys Ile Ile Ala Met Asp Pro Tyr Tyr Tyr
                805                 810                 815 ttc caa gaa ggc tgg aat atc ttt gac ggt ttt att gtg acg ctt agc      2496
Phe Gln Glu Gly Trp Asn Ile Phe Asp Gly Phe Ile Val Thr Leu Ser
            820                 825                 830 ctg gta gaa ctt gga ctc gcc aat gtg gaa gga tta tct gtt ctc cgt      2544
Leu Val Glu Leu Gly Leu Ala Asn Val Glu Gly Leu Ser Val Leu Arg
        835                 840                 845 tca ttt cga ttg ctg cga gtt ttc aag ttg gca aaa tct tgg cca acg      2592
Ser Phe Arg Leu Leu Arg Val Phe Lys Leu Ala Lys Ser Trp Pro Thr
    850                 855                 860 tta aat atg cta ata aag atc atc ggc aat tcc gtg ggg gct ctg gga      2640
Leu Asn Met Leu Ile Lys Ile Ile Gly Asn Ser Val Gly Ala Leu Gly
865                 870                 875                 880 aat tta acc ctc gtc ttg gcc atc atc gtc ttc att ttt gcc gtg gtc      2688
Asn Leu Thr Leu Val Leu Ala Ile Ile Val Phe Ile Phe Ala Val Val
                885                 890                 895 ggc atg cag ctc ttt ggt aaa agc tac aaa gat tgt gtc tgc aag atc      2736
Gly Met Gln Leu Phe Gly Lys Ser Tyr Lys Asp Cys Val Cys Lys Ile
            900                 905                 910 gcc agt gat tgt caa ctc cca cgc tgg cac atg aat gac ttc ttc cac      2784
Ala Ser Asp Cys Gln Leu Pro Arg Trp His Met Asn Asp Phe Phe His
        915                 920                 925 tcc ttc ctg att gtg ttc cgc gtg ctg tgt ggg gag tgg ata gag acc      2832
Ser Phe Leu Ile Val Phe Arg Val Leu Cys Gly Glu Trp Ile Glu Thr
    930                 935                 940 atg tgg gac tgt atg gag gtt gct ggt caa gcc atg tgc ctt act gtc      2880
Met Trp Asp Cys Met Glu Val Ala Gly Gln Ala Met Cys Leu Thr Val
945                 950                 955                 960 ttc atg atg gtc atg gtg att gga aac cta gtg gtc ctg aat ctc ttt      2928
Phe Met Met Val Met Val Ile Gly Asn Leu Val Val Leu Asn Leu Phe
                965                 970                 975 ctg gcc ttg ctt ctg agc tca ttt agt gca gac aac ctt gca gcc act      2976
Leu Ala Leu Leu Leu Ser Ser Phe Ser Ala Asp Asn Leu Ala Ala Thr
            980                 985                 990 gat gat gat aat gaa atg aat aat  ctc caa att gct gtg  gat agg atg    3024
Asp Asp Asp Asn Glu Met Asn Asn  Leu Gln Ile Ala Val  Asp Arg Met
        995                 1000                 1005 cac aaa  gga gta gct tat gtg  aaa aga aaa ata tat  gaa ttt att       3069
```

```
                                                        -continued

His Lys Gly Val Ala Tyr Val Lys Arg Lys Ile Tyr Glu Phe Ile
    1010            1015            1020 caa cag tcc ttc att agg aaa caa aag att tta gat gaa att aaa       3114
Gln Gln Ser Phe Ile Arg Lys Gln Lys Ile Leu Asp Glu Ile Lys
    1025            1030            1035 cca ctt gat gat cta aac aac aag aaa gac agt tgt atg tcc aat       3159
Pro Leu Asp Asp Leu Asn Asn Lys Lys Asp Ser Cys Met Ser Asn
    1040            1045            1050 cat aca gca gaa att ggg aaa gat ctt gac tat ctt aaa gat gta       3204
His Thr Ala Glu Ile Gly Lys Asp Leu Asp Tyr Leu Lys Asp Val
    1055            1060            1065 aat gga act aca agt ggt ata gga act ggc agc agt gtt gaa aaa       3249
Asn Gly Thr Thr Ser Gly Ile Gly Thr Gly Ser Ser Val Glu Lys
    1070            1075            1080 tac att att gat gaa agt gat tac atg tca ttc ata aac aac ccc       3294
Tyr Ile Ile Asp Glu Ser Asp Tyr Met Ser Phe Ile Asn Asn Pro
    1085            1090            1095 agt ctt act gtg act gta cca att gct gta gga gaa tct gac ttt       3339
Ser Leu Thr Val Thr Val Pro Ile Ala Val Gly Glu Ser Asp Phe
    1100            1105            1110 gaa aat tta aac acg gaa gac ttt agt agt gaa tcg gat ctg gaa       3384
Glu Asn Leu Asn Thr Glu Asp Phe Ser Ser Glu Ser Asp Leu Glu
    1115            1120            1125 gaa agc aaa gag aaa ctg aat gaa agc agt agc tca tca gaa ggt       3429
Glu Ser Lys Glu Lys Leu Asn Glu Ser Ser Ser Ser Ser Glu Gly
    1130            1135            1140 agc act gtg gac atc ggc gca cct gta gaa gaa cag ccc gta gtg       3474
Ser Thr Val Asp Ile Gly Ala Pro Val Glu Glu Gln Pro Val Val
    1145            1150            1155 gaa cct gaa gaa act ctt gaa cca gaa gct tgt ttc act gaa ggc       3519
Glu Pro Glu Glu Thr Leu Glu Pro Glu Ala Cys Phe Thr Glu Gly
    1160            1165            1170 tgt gta caa aga ttc aag tgt tgt caa atc aat gtg gaa gaa ggc       3564
Cys Val Gln Arg Phe Lys Cys Cys Gln Ile Asn Val Glu Glu Gly
    1175            1180            1185 aga gga aaa caa tgg tgg aac ctg aga agg acg tgt ttc cga ata       3609
Arg Gly Lys Gln Trp Trp Asn Leu Arg Arg Thr Cys Phe Arg Ile
    1190            1195            1200 gtt gaa cat aac tgg ttt gag acc ttc att gtt ttc atg att ctc       3654
Val Glu His Asn Trp Phe Glu Thr Phe Ile Val Phe Met Ile Leu
    1205            1210            1215 ctt agt agt ggt gct ctg gca ttt gaa gat ata tat att gat cag       3699
Leu Ser Ser Gly Ala Leu Ala Phe Glu Asp Ile Tyr Ile Asp Gln
    1220            1225            1230 cga aag acg att aag acg atg ttg gaa tat gct gac aag gtt ttc       3744
Arg Lys Thr Ile Lys Thr Met Leu Glu Tyr Ala Asp Lys Val Phe
    1235            1240            1245 act tac att ttc att ctg gaa atg ctt cta aaa tgg gtg gca tat       3789
Thr Tyr Ile Phe Ile Leu Glu Met Leu Leu Lys Trp Val Ala Tyr
    1250            1255            1260 ggc tat caa aca tat ttc acc aat gcc tgg tgt tgg ctg gac ttc       3834
Gly Tyr Gln Thr Tyr Phe Thr Asn Ala Trp Cys Trp Leu Asp Phe
    1265            1270            1275 tta att gtt gat gtt tca ttg gtc agt tta aca gca aat gcc ttg       3879
Leu Ile Val Asp Val Ser Leu Val Ser Leu Thr Ala Asn Ala Leu
    1280            1285            1290 ggt tac tca gaa ctt gga gcc atc aaa tct ctc agg aca cta aga       3924
Gly Tyr Ser Glu Leu Gly Ala Ile Lys Ser Leu Arg Thr Leu Arg
    1295            1300            1305
```

```
gct ctg aga cct cta aga gcc tta tct cga ttt gaa ggg atg agg      3969
Ala Leu Arg Pro Leu Arg Ala Leu Ser Arg Phe Glu Gly Met Arg
    1310            1315                1320 gtg gtt gtg aat gcc ctt tta gga gca att cca tcc atc atg aat      4014
Val Val Val Asn Ala Leu Leu Gly Ala Ile Pro Ser Ile Met Asn
1325            1330                1335 gtg ctt ctg gtt tgt ctt ata ttc tgg cta att ttc agc atc atg      4059
Val Leu Leu Val Cys Leu Ile Phe Trp Leu Ile Phe Ser Ile Met
    1340            1345                1350 ggc gta aat ttg ttt gct ggc aaa ttc tac cac tgt att aac acc      4104
Gly Val Asn Leu Phe Ala Gly Lys Phe Tyr His Cys Ile Asn Thr
1355            1360                1365 aca act ggt gac agg ttt gac atc gaa gac gtg aat aat cat act      4149
Thr Thr Gly Asp Arg Phe Asp Ile Glu Asp Val Asn Asn His Thr
    1370            1375                1380 gat tgc cta aaa cta ata gaa aga aat gag act gct cga tgg aaa      4194
Asp Cys Leu Lys Leu Ile Glu Arg Asn Glu Thr Ala Arg Trp Lys
1385            1390                1395 aat gtg aaa gta aac ttt gat aat gta gga ttt ggg tat ctc tct      4239
Asn Val Lys Val Asn Phe Asp Asn Val Gly Phe Gly Tyr Leu Ser
    1400            1405                1410 ttg ctt caa gtt gcc aca ttc aaa gga tgg atg gat ata atg tat      4284
Leu Leu Gln Val Ala Thr Phe Lys Gly Trp Met Asp Ile Met Tyr
1415            1420                1425 gca gca gtt gat tcc aga aat gtg gaa ctc cag cct aag tat gaa      4329
Ala Ala Val Asp Ser Arg Asn Val Glu Leu Gln Pro Lys Tyr Glu
    1430            1435                1440 gaa agt ctg tac atg tat ctt tac ttt gtt att ttc atc atc ttt      4374
Glu Ser Leu Tyr Met Tyr Leu Tyr Phe Val Ile Phe Ile Ile Phe
1445            1450                1455 ggg tcc ttc ttc acc ttg aac ctg ttt att ggt gtc atc ata gat      4419
Gly Ser Phe Phe Thr Leu Asn Leu Phe Ile Gly Val Ile Ile Asp
    1460            1465                1470 aat ttc aac cag cag aaa aag aag ttt gga ggt caa gac atc ttt      4464
Asn Phe Asn Gln Gln Lys Lys Lys Phe Gly Gly Gln Asp Ile Phe
1475            1480                1485 atg aca gaa gaa cag aag aaa tac tat aat gca atg aaa aaa tta      4509
Met Thr Glu Glu Gln Lys Lys Tyr Tyr Asn Ala Met Lys Lys Leu
    1490            1495                1500 gga tcg aaa aaa ccg caa aag cct ata cct cga cca gga aac aaa      4554
Gly Ser Lys Lys Pro Gln Lys Pro Ile Pro Arg Pro Gly Asn Lys
1505            1510                1515 ttt caa gga atg gtc ttt gac ttc gta acc aga caa gtt ttt gac      4599
Phe Gln Gly Met Val Phe Asp Phe Val Thr Arg Gln Val Phe Asp
    1520            1525                1530 ata agc atc atg att ctc atc tgt ctt aac atg gtc aca atg atg      4644
Ile Ser Ile Met Ile Leu Ile Cys Leu Asn Met Val Thr Met Met
1535            1540                1545 gtg gaa aca gat gac cag agt gaa tat gtg act acc att ttg tca      4689
Val Glu Thr Asp Asp Gln Ser Glu Tyr Val Thr Thr Ile Leu Ser
    1550            1555                1560 cgc atc aat ctg gtg ttc att gtg cta ttt act gga gag tgt gta      4734
Arg Ile Asn Leu Val Phe Ile Val Leu Phe Thr Gly Glu Cys Val
1565            1570                1575 ctg aaa ctc atc tct cta cgc cat tat tat ttt acc att gga tgg      4779
Leu Lys Leu Ile Ser Leu Arg His Tyr Tyr Phe Thr Ile Gly Trp
    1580            1585                1590 aat att ttt gat ttt gtg gtt gtc att ctc tcc att gta ggt atg      4824
Asn Ile Phe Asp Phe Val Val Val Ile Leu Ser Ile Val Gly Met
1595            1600                1605
```

-continued

| | |
|---|---|
| ttt ctt gcc gag ctg ata gaa aag tat ttc gtg tcc cct acc ctg<br>Phe Leu Ala Glu Leu Ile Glu Lys Tyr Phe Val Ser Pro Thr Leu<br>1610                         1615                       1620 | 4869 |
| ttc cga gtg atc cgt ctt gct agg att ggc cga atc cta cgt ctg<br>Phe Arg Val Ile Arg Leu Ala Arg Ile Gly Arg Ile Leu Arg Leu<br>1625                         1630                       1635 | 4914 |
| atc aaa gga gca aag ggg atc cgc acg ctg ctc ttt gct ttg atg<br>Ile Lys Gly Ala Lys Gly Ile Arg Thr Leu Leu Phe Ala Leu Met<br>1640                         1645                       1650 | 4959 |
| atg tcc ctt cct gcg ttg ttt aac atc ggc ctc cta ctc ttc cta<br>Met Ser Leu Pro Ala Leu Phe Asn Ile Gly Leu Leu Leu Phe Leu<br>1655                         1660                       1665 | 5004 |
| gtc atg ttc atc tac gcc atc ttt ggg atg tcc aac ttt gcc tat<br>Val Met Phe Ile Tyr Ala Ile Phe Gly Met Ser Asn Phe Ala Tyr<br>1670                         1675                       1680 | 5049 |
| gtt aag agg gaa gtt ggg atc gat gac atg ttc aac ttt gag acc<br>Val Lys Arg Glu Val Gly Ile Asp Asp Met Phe Asn Phe Glu Thr<br>1685                         1690                       1695 | 5094 |
| ttt ggc aac agc atg atc tgc cta ttc caa att aca acc tct gct<br>Phe Gly Asn Ser Met Ile Cys Leu Phe Gln Ile Thr Thr Ser Ala<br>1700                         1705                       1710 | 5139 |
| ggc tgg gat gga ttg cta gca ccc att ctc aac agt aag cca ccc<br>Gly Trp Asp Gly Leu Leu Ala Pro Ile Leu Asn Ser Lys Pro Pro<br>1715                         1720                       1725 | 5184 |
| gac tgt gac cct aat aaa gtt aac cct gga agc tca gtt aag gga<br>Asp Cys Asp Pro Asn Lys Val Asn Pro Gly Ser Ser Val Lys Gly<br>1730                         1735                       1740 | 5229 |
| gac tgt ggg aac cca tct gtt gga att ttc ttt ttt gtc agt tac<br>Asp Cys Gly Asn Pro Ser Val Gly Ile Phe Phe Phe Val Ser Tyr<br>1745                         1750                       1755 | 5274 |
| atc atc ata tcc ttc ctg gtt gtg gtg aac atg tac atc gcg gtc<br>Ile Ile Ile Ser Phe Leu Val Val Val Asn Met Tyr Ile Ala Val<br>1760                         1765                       1770 | 5319 |
| atc ctg gag aac ttc agt gtt gct act gaa gaa agt gca gag cct<br>Ile Leu Glu Asn Phe Ser Val Ala Thr Glu Glu Ser Ala Glu Pro<br>1775                         1780                       1785 | 5364 |
| ctg agt gag gat gac ttt gag atg ttc tat gag gtt tgg gag aag<br>Leu Ser Glu Asp Asp Phe Glu Met Phe Tyr Glu Val Trp Glu Lys<br>1790                         1795                       1800 | 5409 |
| ttt gat ccc gat gca act cag ttc atg gaa ttt gaa aaa tta tct<br>Phe Asp Pro Asp Ala Thr Gln Phe Met Glu Phe Glu Lys Leu Ser<br>1805                         1810                       1815 | 5454 |
| cag ttt gca gct gcg ctt gaa ccg cct ctc aat ctg cca caa cca<br>Gln Phe Ala Ala Ala Leu Glu Pro Pro Leu Asn Leu Pro Gln Pro<br>1820                         1825                       1830 | 5499 |
| aac aaa ctc cag ctc att gcc atg gat ttg ccc atg gtg agt ggt<br>Asn Lys Leu Gln Leu Ile Ala Met Asp Leu Pro Met Val Ser Gly<br>1835                         1840                       1845 | 5544 |
| gac cgg atc cac tgt ctt gat atc tta ttt gct ttt aca aag cgg<br>Asp Arg Ile His Cys Leu Asp Ile Leu Phe Ala Phe Thr Lys Arg<br>1850                         1855                       1860 | 5589 |
| gtt cta gga gag agt gga gag atg gat gct cta cga ata cag atg<br>Val Leu Gly Glu Ser Gly Glu Met Asp Ala Leu Arg Ile Gln Met<br>1865                         1870                       1875 | 5634 |
| gaa gag cga ttc atg gct tcc aat cct tcc aag gtc tcc tat cag<br>Glu Glu Arg Phe Met Ala Ser Asn Pro Ser Lys Val Ser Tyr Gln<br>1880                         1885                       1890 | 5679 |
| cca atc act act act tta aaa cga aaa caa gag gaa gta tct gct<br>Pro Ile Thr Thr Thr Leu Lys Arg Lys Gln Glu Glu Val Ser Ala | 5724 |

```
              1895                1900                1905
gtc att att cag cgt gct tac aga cgc cac ctt tta aag cga act    5769
Val Ile Ile Gln Arg Ala Tyr Arg Arg His Leu Leu Lys Arg Thr
    1910                1915                1920 gta aaa caa gct tcc ttt acg tac aat aaa aac aaa atc aaa ggt    5814
Val Lys Gln Ala Ser Phe Thr Tyr Asn Lys Asn Lys Ile Lys Gly
    1925                1930                1935 ggg gct aat ctt ctt ata aaa gaa gac atg ata att gac aga ata    5859
Gly Ala Asn Leu Leu Ile Lys Glu Asp Met Ile Ile Asp Arg Ile
    1940                1945                1950 aat gaa aac tct att aca gaa aaa act gat ctg acc atg tcc act    5904
Asn Glu Asn Ser Ile Thr Glu Lys Thr Asp Leu Thr Met Ser Thr
    1955                1960                1965 gca gct tgt cca cct tcc tat gac cgg gtg aca aag cca att gtg    5949
Ala Ala Cys Pro Pro Ser Tyr Asp Arg Val Thr Lys Pro Ile Val
    1970                1975                1980 gaa aaa cat gag caa gaa ggc aaa gat gaa aaa gcc aaa ggg aaa    5994
Glu Lys His Glu Gln Glu Gly Lys Asp Glu Lys Ala Lys Gly Lys
    1985                1990                1995 taa                                                            5997

<210> SEQ ID NO 21
<211> LENGTH: 1998
<212> TYPE: PRT
<213> ORGANISM: Homo sapiens

<400> SEQUENCE: 21

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
                20                  25                  30

Lys Ala Lys Asn Pro Lys Pro Asp Lys Lys Asp Asp Asp Glu Asn Gly
            35                  40                  45

Pro Lys Pro Asn Ser Asp Leu Glu Ala Gly Lys Asn Leu Pro Phe Ile
        50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
```

```
        225                 230                 235                 240
Ile Gln Ser Val Lys Lys Leu Ser Asp Val Met Ile Leu Thr Val Phe
                245                 250                 255
Cys Leu Ser Val Phe Ala Leu Ile Gly Leu Gln Leu Phe Met Gly Asn
                260                 265                 270
Leu Arg Asn Lys Cys Ile Gln Trp Pro Pro Thr Asn Ala Ser Leu Glu
            275                 280                 285
Glu His Ser Ile Glu Lys Asn Ile Thr Val Asn Tyr Asn Gly Thr Leu
        290                 295                 300
Ile Asn Glu Thr Val Phe Glu Phe Asp Trp Lys Ser Tyr Ile Gln Asp
305                 310                 315                 320
Ser Arg Tyr His Tyr Phe Leu Glu Gly Phe Leu Asp Ala Leu Leu Cys
                325                 330                 335
Gly Asn Ser Ser Asp Ala Gly Gln Cys Pro Glu Gly Tyr Met Cys Val
                340                 345                 350
Lys Ala Gly Arg Asn Pro Asn Tyr Gly Tyr Thr Ser Phe Asp Thr Phe
            355                 360                 365
Ser Trp Ala Phe Leu Ser Leu Phe Arg Leu Met Thr Gln Asp Phe Trp
        370                 375                 380
Glu Asn Leu Tyr Gln Leu Thr Leu Arg Ala Ala Gly Lys Thr Tyr Met
385                 390                 395                 400
Ile Phe Phe Val Leu Val Ile Phe Leu Gly Ser Phe Tyr Leu Ile Asn
                405                 410                 415
Leu Ile Leu Ala Val Val Ala Met Ala Tyr Glu Glu Gln Asn Gln Ala
                420                 425                 430
Thr Leu Glu Glu Ala Glu Gln Lys Glu Ala Glu Phe Gln Gln Met Ile
            435                 440                 445
Glu Gln Leu Lys Lys Gln Gln Glu Ala Ala Gln Gln Ala Ala Thr Ala
        450                 455                 460
Thr Ala Ser Glu His Ser Arg Glu Pro Ser Ala Ala Gly Arg Leu Ser
465                 470                 475                 480
Asp Ser Ser Ser Glu Ala Ser Lys Leu Ser Ser Lys Ser Ala Lys Glu
                485                 490                 495
Arg Arg Asn Arg Arg Lys Lys Arg Lys Gln Lys Glu Gln Ser Gly Gly
                500                 505                 510
Glu Glu Lys Asp Glu Asp Glu Phe Gln Lys Ser Glu Ser Glu Asp Ser
            515                 520                 525
Ile Arg Arg Lys Gly Phe Arg Phe Ser Ile Glu Gly Asn Arg Leu Thr
        530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
                580                 585                 590
Asp Glu His Ser Thr Phe Glu Asp Asn Glu Ser Arg Arg Asp Ser Leu
            595                 600                 605
Phe Val Pro Arg Arg His Gly Glu Arg Arg Asn Ser Asn Leu Ser Gln
        610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                645                 650                 655
```

```
Pro Ser Val Pro Thr Ser Pro Val Gly Gln Leu Leu Pro Glu Gly Thr
            660                 665                 670

Thr Thr Glu Thr Glu Met Arg Lys Arg Arg Ser Ser Phe His Val
        675                 680                 685

Ser Met Asp Phe Leu Glu Asp Pro Ser Gln Arg Gln Arg Ala Met Ser
            690                 695                 700

Ile Ala Ser Ile Leu Thr Asn Thr Val Glu Glu Leu Glu Glu Ser Arg
705                 710                 715                 720

Gln Lys Cys Pro Pro Cys Trp Tyr Lys Phe Ser Asn Ile Phe Leu Ile
                725                 730                 735

Trp Asp Cys Ser Pro Tyr Trp Leu Lys Val Lys His Val Val Asn Leu
            740                 745                 750

Val Val Met Asp Pro Phe Val Asp Leu Ala Ile Thr Ile Cys Ile Val
            755                 760                 765

Leu Asn Thr Leu Phe Met Ala Met Glu His Tyr Pro Met Thr Asp His
    770                 775                 780

Phe Asn Asn Val Leu Thr Val Gly Asn Leu Val Phe Thr Gly Ile Phe
785                 790                 795                 800

Thr Ala Glu Met Phe Leu Lys Ile Ile Ala Met Asp Pro Tyr Tyr Tyr
                805                 810                 815

Phe Gln Glu Gly Trp Asn Ile Phe Asp Gly Phe Ile Val Thr Leu Ser
            820                 825                 830

Leu Val Glu Leu Gly Leu Ala Asn Val Glu Gly Leu Ser Val Leu Arg
            835                 840                 845

Ser Phe Arg Leu Leu Arg Val Phe Lys Leu Ala Lys Ser Trp Pro Thr
    850                 855                 860

Leu Asn Met Leu Ile Lys Ile Ile Gly Asn Ser Val Gly Ala Leu Gly
865                 870                 875                 880

Asn Leu Thr Leu Val Leu Ala Ile Ile Val Phe Ile Phe Ala Val Val
                885                 890                 895

Gly Met Gln Leu Phe Gly Lys Ser Tyr Lys Asp Cys Val Cys Lys Ile
            900                 905                 910

Ala Ser Asp Cys Gln Leu Pro Arg Trp His Met Asn Asp Phe Phe His
    915                 920                 925

Ser Phe Leu Ile Val Phe Arg Val Leu Cys Gly Glu Trp Ile Glu Thr
    930                 935                 940

Met Trp Asp Cys Met Glu Val Ala Gly Gln Ala Met Cys Leu Thr Val
945                 950                 955                 960

Phe Met Met Val Met Val Ile Gly Asn Leu Val Val Leu Asn Leu Phe
                965                 970                 975

Leu Ala Leu Leu Leu Ser Ser Phe Ser Ala Asp Asn Leu Ala Ala Thr
            980                 985                 990

Asp Asp Asp Asn Glu Met Asn Asn  Leu Gln Ile Ala Val  Asp Arg Met
            995                 1000                1005

His Lys  Gly Val Ala Tyr Val  Lys Arg Lys Ile Tyr  Glu Phe Ile
    1010                1015                1020

Gln Gln  Ser Phe Ile Arg Lys  Gln Lys Ile Leu Asp  Glu Ile Lys
    1025                1030                1035

Pro Leu  Asp Asp Leu Asn Asn  Lys Lys Asp Ser Cys  Met Ser Asn
    1040                1045                1050

His Thr  Ala Glu Ile Gly Lys  Asp Leu Asp Tyr Leu  Lys Asp Val
    1055                1060                1065
```

-continued

```
Asn Gly Thr Thr Ser Gly Ile Gly Thr Gly Ser Ser Val Glu Lys
    1070            1075            1080

Tyr Ile Ile Asp Glu Ser Asp Tyr Met Ser Phe Ile Asn Asn Pro
    1085            1090            1095

Ser Leu Thr Val Thr Val Pro Ile Ala Val Gly Glu Ser Asp Phe
    1100            1105            1110

Glu Asn Leu Asn Thr Glu Asp Phe Ser Ser Glu Ser Asp Leu Glu
    1115            1120            1125

Glu Ser Lys Glu Lys Leu Asn Glu Ser Ser Ser Ser Glu Gly
    1130            1135            1140

Ser Thr Val Asp Ile Gly Ala Pro Val Glu Glu Gln Pro Val Val
    1145            1150            1155

Glu Pro Glu Glu Thr Leu Glu Pro Glu Ala Cys Phe Thr Glu Gly
    1160            1165            1170

Cys Val Gln Arg Phe Lys Cys Cys Gln Ile Asn Val Glu Glu Gly
    1175            1180            1185

Arg Gly Lys Gln Trp Trp Asn Leu Arg Arg Thr Cys Phe Arg Ile
    1190            1195            1200

Val Glu His Asn Trp Phe Glu Thr Phe Ile Val Phe Met Ile Leu
    1205            1210            1215

Leu Ser Ser Gly Ala Leu Ala Phe Glu Asp Ile Tyr Ile Asp Gln
    1220            1225            1230

Arg Lys Thr Ile Lys Thr Met Leu Glu Tyr Ala Asp Lys Val Phe
    1235            1240            1245

Thr Tyr Ile Phe Ile Leu Glu Met Leu Leu Lys Trp Val Ala Tyr
    1250            1255            1260

Gly Tyr Gln Thr Tyr Phe Thr Asn Ala Trp Cys Trp Leu Asp Phe
    1265            1270            1275

Leu Ile Val Asp Val Ser Leu Val Ser Leu Thr Ala Asn Ala Leu
    1280            1285            1290

Gly Tyr Ser Glu Leu Gly Ala Ile Lys Ser Leu Arg Thr Leu Arg
    1295            1300            1305

Ala Leu Arg Pro Leu Arg Ala Leu Ser Arg Phe Glu Gly Met Arg
    1310            1315            1320

Val Val Val Asn Ala Leu Leu Gly Ala Ile Pro Ser Ile Met Asn
    1325            1330            1335

Val Leu Leu Val Cys Leu Ile Phe Trp Leu Ile Phe Ser Ile Met
    1340            1345            1350

Gly Val Asn Leu Phe Ala Gly Lys Phe Tyr His Cys Ile Asn Thr
    1355            1360            1365

Thr Thr Gly Asp Arg Phe Asp Ile Glu Asp Val Asn Asn His Thr
    1370            1375            1380

Asp Cys Leu Lys Leu Ile Glu Arg Asn Glu Thr Ala Arg Trp Lys
    1385            1390            1395

Asn Val Lys Val Asn Phe Asp Asn Val Gly Phe Gly Tyr Leu Ser
    1400            1405            1410

Leu Leu Gln Val Ala Thr Phe Lys Gly Trp Met Asp Ile Met Tyr
    1415            1420            1425

Ala Ala Val Asp Ser Arg Asn Val Glu Leu Gln Pro Lys Tyr Glu
    1430            1435            1440

Glu Ser Leu Tyr Met Tyr Leu Tyr Phe Val Ile Phe Ile Ile Phe
    1445            1450            1455

Gly Ser Phe Phe Thr Leu Asn Leu Phe Ile Gly Val Ile Ile Asp
```

-continued

```
        1460                1465                1470
Asn Phe Asn Gln Gln Lys Lys Phe Gly Gly Gln Asp Ile Phe
        1475                1480                1485
Met Thr Glu Glu Gln Lys Lys Tyr Tyr Asn Ala Met Lys Lys Leu
        1490                1495                1500
Gly Ser Lys Lys Pro Gln Lys Pro Ile Pro Arg Pro Gly Asn Lys
        1505                1510                1515
Phe Gln Gly Met Val Phe Asp Phe Val Thr Arg Gln Val Phe Asp
        1520                1525                1530
Ile Ser Ile Met Ile Leu Ile Cys Leu Asn Met Val Thr Met Met
        1535                1540                1545
Val Glu Thr Asp Asp Gln Ser Glu Tyr Val Thr Thr Ile Leu Ser
        1550                1555                1560
Arg Ile Asn Leu Val Phe Ile Val Leu Phe Thr Gly Glu Cys Val
        1565                1570                1575
Leu Lys Leu Ile Ser Leu Arg His Tyr Tyr Phe Thr Ile Gly Trp
        1580                1585                1590
Asn Ile Phe Asp Phe Val Val Val Ile Leu Ser Ile Val Gly Met
        1595                1600                1605
Phe Leu Ala Glu Leu Ile Glu Lys Tyr Phe Val Ser Pro Thr Leu
        1610                1615                1620
Phe Arg Val Ile Arg Leu Ala Arg Ile Gly Arg Ile Leu Arg Leu
        1625                1630                1635
Ile Lys Gly Ala Lys Gly Ile Arg Thr Leu Leu Phe Ala Leu Met
        1640                1645                1650
Met Ser Leu Pro Ala Leu Phe Asn Ile Gly Leu Leu Leu Phe Leu
        1655                1660                1665
Val Met Phe Ile Tyr Ala Ile Phe Gly Met Ser Asn Phe Ala Tyr
        1670                1675                1680
Val Lys Arg Glu Val Gly Ile Asp Asp Met Phe Asn Phe Glu Thr
        1685                1690                1695
Phe Gly Asn Ser Met Ile Cys Leu Phe Gln Ile Thr Thr Ser Ala
        1700                1705                1710
Gly Trp Asp Gly Leu Leu Ala Pro Ile Leu Asn Ser Lys Pro Pro
        1715                1720                1725
Asp Cys Asp Pro Asn Lys Val Asn Pro Gly Ser Ser Val Lys Gly
        1730                1735                1740
Asp Cys Gly Asn Pro Ser Val Gly Ile Phe Phe Phe Val Ser Tyr
        1745                1750                1755
Ile Ile Ile Ser Phe Leu Val Val Val Asn Met Tyr Ile Ala Val
        1760                1765                1770
Ile Leu Glu Asn Phe Ser Val Ala Thr Glu Glu Ser Ala Glu Pro
        1775                1780                1785
Leu Ser Glu Asp Asp Phe Glu Met Phe Tyr Glu Val Trp Glu Lys
        1790                1795                1800
Phe Asp Pro Asp Ala Thr Gln Phe Met Glu Phe Glu Lys Leu Ser
        1805                1810                1815
Gln Phe Ala Ala Ala Leu Glu Pro Pro Leu Asn Leu Pro Gln Pro
        1820                1825                1830
Asn Lys Leu Gln Leu Ile Ala Met Asp Leu Pro Met Val Ser Gly
        1835                1840                1845
Asp Arg Ile His Cys Leu Asp Ile Leu Phe Ala Phe Thr Lys Arg
        1850                1855                1860
```

```
Val Leu Gly Glu Ser Gly Glu Met Asp Ala Leu Arg Ile Gln Met
    1865            1870                1875

Glu Glu Arg Phe Met Ala Ser Asn Pro Ser Lys Val Ser Tyr Gln
        1880            1885                1890

Pro Ile Thr Thr Thr Leu Lys Arg Lys Gln Glu Glu Val Ser Ala
    1895                1900                1905

Val Ile Ile Gln Arg Ala Tyr Arg Arg His Leu Leu Lys Arg Thr
    1910                1915                1920

Val Lys Gln Ala Ser Phe Thr Tyr Asn Lys Asn Lys Ile Lys Gly
    1925                1930                1935

Gly Ala Asn Leu Leu Ile Lys Glu Asp Met Ile Ile Asp Arg Ile
    1940                1945                1950

Asn Glu Asn Ser Ile Thr Glu Lys Thr Asp Leu Thr Met Ser Thr
    1955                1960                1965

Ala Ala Cys Pro Pro Ser Tyr Asp Arg Val Thr Lys Pro Ile Val
    1970                1975                1980

Glu Lys His Glu Gln Glu Gly Lys Asp Glu Lys Ala Lys Gly Lys
    1985                1990                1995

<210> SEQ ID NO 22
<211> LENGTH: 5946
<212> TYPE: DNA
<213> ORGANISM: Homo sapiens
<220> FEATURE:
<221> NAME/KEY: CDS
<222> LOCATION: (1)..(5946)

<400> SEQUENCE: 22 atg gag caa aca gtg ctt gta cca cca gga cct gac agc ttc aac ttc      48
Met Glu Gln Thr Val Leu Val Pro Pro Gly Pro Asp Ser Phe Asn Phe
1               5                   10                  15 ttc acc aga gaa tct ctt gcg gct att gaa aga cgc att gca gaa gaa      96
Phe Thr Arg Glu Ser Leu Ala Ala Ile Glu Arg Arg Ile Ala Glu Glu
            20                  25                  30 aag gca aag aat ccc aaa cca gac aaa aaa gat gac gac gaa aat ggc     144
Lys Ala Lys Asn Pro Lys Pro Asp Lys Lys Asp Asp Asp Glu Asn Gly
        35                  40                  45 cca aag cca aat agt gac ttg gaa gct gga aag aac ctt cca ttt att     192
Pro Lys Pro Asn Ser Asp Leu Glu Ala Gly Lys Asn Leu Pro Phe Ile
    50                  55                  60 tat gga gac att cct cca gag atg gtg tca gag ccc ctg gag gac ctg     240
Tyr Gly Asp Ile Pro Pro Glu Met Val Ser Glu Pro Leu Glu Asp Leu
65                  70                  75                  80 gac ccc tac tat atc aat aag aaa act ttt ata gta ttg aat aaa ggg     288
Asp Pro Tyr Tyr Ile Asn Lys Lys Thr Phe Ile Val Leu Asn Lys Gly
                85                  90                  95 aag gcc atc ttc cgg ttc agt gcc acc tct gcc ctg tac att tta act     336
Lys Ala Ile Phe Arg Phe Ser Ala Thr Ser Ala Leu Tyr Ile Leu Thr
            100                 105                 110 ccc ttc aat cct ctt agg aaa ata gct att aag att ttg gta cat tca     384
Pro Phe Asn Pro Leu Arg Lys Ile Ala Ile Lys Ile Leu Val His Ser
        115                 120                 125 tta ttc agc atg cta att atg tgc act att ttg aca aac tgt gtg ttt     432
Leu Phe Ser Met Leu Ile Met Cys Thr Ile Leu Thr Asn Cys Val Phe
    130                 135                 140 atg aca atg agt aac cct cct gat tgg aca aag aat gta gaa tac acc     480
Met Thr Met Ser Asn Pro Pro Asp Trp Thr Lys Asn Val Glu Tyr Thr
145                 150                 155                 160
```

| | | |
|---|---|---|
| ttc aca gga ata tat act ttt gaa tca ctt ata aaa att att gca agg<br>Phe Thr Gly Ile Tyr Thr Phe Glu Ser Leu Ile Lys Ile Ile Ala Arg<br>                 165                       170                  175 | 528 | |
| gga ttc tgt tta gaa gat ttt act ttc ctt cgg gat cca tgg aac tgg<br>Gly Phe Cys Leu Glu Asp Phe Thr Phe Leu Arg Asp Pro Trp Asn Trp<br>                 180                       185                  190 | 576 | |
| ctc gat ttc act gtc att aca ttt gcg tac gtc aca gag ttt gtg gac<br>Leu Asp Phe Thr Val Ile Thr Phe Ala Tyr Val Thr Glu Phe Val Asp<br>                 195                       200                  205 | 624 | |
| ctg ggc aat gtc tcg gca ttg aga aca ttc aga gtt ctc cga gca ttg<br>Leu Gly Asn Val Ser Ala Leu Arg Thr Phe Arg Val Leu Arg Ala Leu<br>       210                       215                       220 | 672 | |
| aag acg att tca gtc att cca ggc ctg aaa acc att gtg gga gcc ctg<br>Lys Thr Ile Ser Val Ile Pro Gly Leu Lys Thr Ile Val Gly Ala Leu<br>225                       230                       235                  240 | 720 | |
| atc cag tct gtg aag aag ctc tca gat gta atg atc ctg act gtg ttc<br>Ile Gln Ser Val Lys Lys Leu Ser Asp Val Met Ile Leu Thr Val Phe<br>                 245                       250                  255 | 768 | |
| tgt ctg agc gta ttt gct cta att ggg ctg cag ctg ttc atg ggc aac<br>Cys Leu Ser Val Phe Ala Leu Ile Gly Leu Gln Leu Phe Met Gly Asn<br>                 260                       265                  270 | 816 | |
| ctg agg aat aaa tgt ata caa tgg cct ccc acc aat gct tcc ttg gag<br>Leu Arg Asn Lys Cys Ile Gln Trp Pro Pro Thr Asn Ala Ser Leu Glu<br>       275                       280                       285 | 864 | |
| gaa cat agt ata gaa aag aat ata act gtg aat tat aat ggt aca ctt<br>Glu His Ser Ile Glu Lys Asn Ile Thr Val Asn Tyr Asn Gly Thr Leu<br>                 290                       295                  300 | 912 | |
| ata aat gaa act gtc ttt gag ttt gac tgg aag tca tat att caa gat<br>Ile Asn Glu Thr Val Phe Glu Phe Asp Trp Lys Ser Tyr Ile Gln Asp<br>305                       310                       315                  320 | 960 | |
| tca aga tat cat tat ttc ctg gag ggt ttt tta gat gca cta cta tgt<br>Ser Arg Tyr His Tyr Phe Leu Glu Gly Phe Leu Asp Ala Leu Leu Cys<br>                 325                       330                  335 | 1008 | |
| gga aat agc tct gat gca ggc caa tgt cca gag gga tat atg tgt gtg<br>Gly Asn Ser Ser Asp Ala Gly Gln Cys Pro Glu Gly Tyr Met Cys Val<br>                 340                       345                  350 | 1056 | |
| aaa gct ggt aga aat ccc aat tat ggc tac aca agc ttt gat acc ttc<br>Lys Ala Gly Arg Asn Pro Asn Tyr Gly Tyr Thr Ser Phe Asp Thr Phe<br>       355                       360                       365 | 1104 | |
| agt tgg gct ttt ttg tcc ttg ttt cga cta atg act cag gac ttc tgg<br>Ser Trp Ala Phe Leu Ser Leu Phe Arg Leu Met Thr Gln Asp Phe Trp<br>       370                       375                       380 | 1152 | |
| gaa aat ctt tat caa ctg aca tta cgt gct gct ggg aaa acg tac atg<br>Glu Asn Leu Tyr Gln Leu Thr Leu Arg Ala Ala Gly Lys Thr Tyr Met<br>385                       390                       395                  400 | 1200 | |
| ata ttt ttt gta ttg gtc att ttc ttg ggc tca ttc tac cta ata aat<br>Ile Phe Phe Val Leu Val Ile Phe Leu Gly Ser Phe Tyr Leu Ile Asn<br>                 405                       410                  415 | 1248 | |
| ttg atc ctg gct gtg gtg gcc atg gcc tac gag gaa cag aat cag gcc<br>Leu Ile Leu Ala Val Val Ala Met Ala Tyr Glu Glu Gln Asn Gln Ala<br>                 420                       425                  430 | 1296 | |
| acc ttg gaa gaa gca gaa cag aaa gag gcc gaa ttt cag cag atg att<br>Thr Leu Glu Glu Ala Glu Gln Lys Glu Ala Glu Phe Gln Gln Met Ile<br>       435                       440                       445 | 1344 | |
| gaa cag ctt aaa aag caa cag gag gca gct cag cag gca gca acg gca<br>Glu Gln Leu Lys Lys Gln Gln Glu Ala Ala Gln Gln Ala Ala Thr Ala<br>                 450                       455                  460 | 1392 | |
| act gcc tca gaa cat tcc aga gag ccc agt gca gca ggc agg ctc tca<br>Thr Ala Ser Glu His Ser Arg Glu Pro Ser Ala Ala Gly Arg Leu Ser<br>465                       470                       475                  480 | 1440 | |

```
gac agc tca tct gaa gcc tct aag ttg agt tcc aag agt gct aag gaa      1488
Asp Ser Ser Ser Glu Ala Ser Lys Leu Ser Ser Lys Ser Ala Lys Glu
                485                 490                 495 aga aga aat cgg agg aag aaa aga aaa cag aaa gag cag tct ggt ggg      1536
Arg Arg Asn Arg Arg Lys Lys Arg Lys Gln Lys Glu Gln Ser Gly Gly
            500                 505                 510 gaa gag aaa gat gag gat gaa ttc caa aaa tct gaa tct gag gac agc      1584
Glu Glu Lys Asp Glu Asp Glu Phe Gln Lys Ser Glu Ser Glu Asp Ser
        515                 520                 525 atc agg agg aaa ggt ttt cgc ttc tcc att gaa ggg aac cga ttg aca      1632
Ile Arg Arg Lys Gly Phe Arg Phe Ser Ile Glu Gly Asn Arg Leu Thr
    530                 535                 540 tat gaa aag agg tac tcc tcc cca cac cag tct ttg ttg agc atc cgt      1680
Tyr Glu Lys Arg Tyr Ser Ser Pro His Gln Ser Leu Leu Ser Ile Arg
545                 550                 555                 560 ggc tcc cta ttt tca cca agg cga aat agc aga aca agc ctt ttc agc      1728
Gly Ser Leu Phe Ser Pro Arg Arg Asn Ser Arg Thr Ser Leu Phe Ser
                565                 570                 575 ttt aga ggg cga gca aag gat gtg gga tct gag aac gac ttc gca gat      1776
Phe Arg Gly Arg Ala Lys Asp Val Gly Ser Glu Asn Asp Phe Ala Asp
            580                 585                 590 gat gag cac agc acc ttt gag gat aac gag agc cgt aga gat tcc ttg      1824
Asp Glu His Ser Thr Phe Glu Asp Asn Glu Ser Arg Arg Asp Ser Leu
        595                 600                 605 ttt gtg ccc cga cga cac gga gag aga cgc aac agc aac ctg agt cag      1872
Phe Val Pro Arg Arg His Gly Glu Arg Arg Asn Ser Asn Leu Ser Gln
    610                 615                 620 acc agt agg tca tcc cgg atg ctg gca gtg ttt cca gcg aat ggg aag      1920
Thr Ser Arg Ser Ser Arg Met Leu Ala Val Phe Pro Ala Asn Gly Lys
625                 630                 635                 640 atg cac agc act gtg gat tgc aat ggt gtg gtt tcc ttg gga aca acc      1968
Met His Ser Thr Val Asp Cys Asn Gly Val Val Ser Leu Gly Thr Thr
                645                 650                 655 act gaa act gaa atg aga aag aga agg tca agt tct ttc cac gtt tcc      2016
Thr Glu Thr Glu Met Arg Lys Arg Arg Ser Ser Ser Phe His Val Ser
            660                 665                 670 atg gac ttt cta gaa gat cct tcc caa agg caa cga gca atg agt ata      2064
Met Asp Phe Leu Glu Asp Pro Ser Gln Arg Gln Arg Ala Met Ser Ile
        675                 680                 685 gcc agc att cta aca aat aca gta gaa gaa ctt gaa gaa tcc agg cag      2112
Ala Ser Ile Leu Thr Asn Thr Val Glu Glu Leu Glu Glu Ser Arg Gln
    690                 695                 700 aaa tgc cca ccc tgt tgg tat aaa ttt tcc aac ata ttc tta atc tgg      2160
Lys Cys Pro Pro Cys Trp Tyr Lys Phe Ser Asn Ile Phe Leu Ile Trp
705                 710                 715                 720 gac tgt tct cca tat tgg tta aaa gtg aaa cat gtt gtc aac ctg gtt      2208
Asp Cys Ser Pro Tyr Trp Leu Lys Val Lys His Val Val Asn Leu Val
                725                 730                 735 gtg atg gac cca ttt gtt gac ctg gcc atc acc atc tgt att gtc tta      2256
Val Met Asp Pro Phe Val Asp Leu Ala Ile Thr Ile Cys Ile Val Leu
            740                 745                 750 aat act ctt ttc atg gcc atg gag cac tat cca atg acg gac cat ttc      2304
Asn Thr Leu Phe Met Ala Met Glu His Tyr Pro Met Thr Asp His Phe
        755                 760                 765 aat aat gtg ctt aca gta gga aac ttg gtt ttc act ggg atc ttt aca      2352
Asn Asn Val Leu Thr Val Gly Asn Leu Val Phe Thr Gly Ile Phe Thr
    770                 775                 780 gca gaa atg ttt ctg aaa att att gcc atg gat cct tac tat tat ttc      2400
Ala Glu Met Phe Leu Lys Ile Ile Ala Met Asp Pro Tyr Tyr Tyr Phe
```

```
                                                                        -continued
     785              790              795              800
caa gaa ggc tgg aat atc ttt gac ggt ttt att gtg acg ctt agc ctg          2448
Gln Glu Gly Trp Asn Ile Phe Asp Gly Phe Ile Val Thr Leu Ser Leu
                 805              810              815 gta gaa ctt gga ctc gcc aat gtg gaa gga tta tct gtt ctc cgt tca          2496
Val Glu Leu Gly Leu Ala Asn Val Glu Gly Leu Ser Val Leu Arg Ser
                 820              825              830 ttt cga ttg ctg cga gtt ttc aag ttg gca aaa tct tgg cca acg tta          2544
Phe Arg Leu Leu Arg Val Phe Lys Leu Ala Lys Ser Trp Pro Thr Leu
                 835              840              845 aat atg cta ata aag atc atc ggc aat tcc gtg ggg gct ctg gga aat          2592
Asn Met Leu Ile Lys Ile Ile Gly Asn Ser Val Gly Ala Leu Gly Asn
             850              855              860 tta acc ctc gtc ttg gcc atc atc gtc ttc att ttt gcc gtg gtc ggc          2640
Leu Thr Leu Val Leu Ala Ile Ile Val Phe Ile Phe Ala Val Val Gly
865              870              875              880 atg cag ctc ttt ggt aaa agc tac aaa gat tgt gtc tgc aag atc gcc          2688
Met Gln Leu Phe Gly Lys Ser Tyr Lys Asp Cys Val Cys Lys Ile Ala
                     885              890              895 agt gat tgt caa ctc cca cgc tgg cac atg aat gac ttc ttc cac tcc          2736
Ser Asp Cys Gln Leu Pro Arg Trp His Met Asn Asp Phe Phe His Ser
                 900              905              910 ttc ctg att gtg ttc cgc gtg ctg tgt ggg gag tgg ata gag acc atg          2784
Phe Leu Ile Val Phe Arg Val Leu Cys Gly Glu Trp Ile Glu Thr Met
             915              920              925 tgg gac tgt atg gag gtt gct ggt caa gcc atg tgc ctt act gtc ttc          2832
Trp Asp Cys Met Glu Val Ala Gly Gln Ala Met Cys Leu Thr Val Phe
930              935              940 atg atg gtc atg gtg att gga aac cta gtg gtc ctg aat ctc ttt ctg          2880
Met Met Val Met Val Ile Gly Asn Leu Val Val Leu Asn Leu Phe Leu
945              950              955              960 gcc ttg ctt ctg agc tca ttt agt gca gac aac ctt gca gcc act gat          2928
Ala Leu Leu Leu Ser Ser Phe Ser Ala Asp Asn Leu Ala Ala Thr Asp
                 965              970              975 gat gat aat gaa atg aat aat ctc caa att gct gtg gat agg atg cac          2976
Asp Asp Asn Glu Met Asn Asn Leu Gln Ile Ala Val Asp Arg Met His
             980              985              990 aaa gga gta gct tat gtg aaa aga  aaa ata tat gaa ttt  att caa cag        3024
Lys Gly Val Ala Tyr Val Lys Arg  Lys Ile Tyr Glu Phe  Ile Gln Gln
             995              1000              1005 tcc ttc att agg aaa caa aag  att tta gat gaa att  aaa cca ctt            3069
Ser Phe Ile Arg Lys Gln Lys  Ile Leu Asp Glu Ile  Lys Pro Leu
    1010              1015              1020 gat gat cta aac aac aag aaa  gac agt tgt atg tcc  aat cat aca            3114
Asp Asp Leu Asn Asn Lys Lys  Asp Ser Cys Met Ser  Asn His Thr
    1025              1030              1035 gca gaa att ggg aaa gat ctt  gac tat ctt aaa gat  gta aat gga            3159
Ala Glu Ile Gly Lys Asp Leu  Asp Tyr Leu Lys Asp  Val Asn Gly
    1040              1045              1050 act aca agt ggt ata gga act  ggc agc agt gtt gaa  aaa tac att            3204
Thr Thr Ser Gly Ile Gly Thr  Gly Ser Ser Val Glu  Lys Tyr Ile
    1055              1060              1065 att gat gaa agt gat tac atg  tca ttc ata aac aac  ccc agt ctt            3249
Ile Asp Glu Ser Asp Tyr Met  Ser Phe Ile Asn Asn  Pro Ser Leu
    1070              1075              1080 act gtg act gta cca att gct  gta gga gaa tct gac  ttt gaa aat            3294
Thr Val Thr Val Pro Ile Ala  Val Gly Glu Ser Asp  Phe Glu Asn
    1085              1090              1095 tta aac acg gaa gac ttt agt  agt gaa tcg gat ctg  gaa gaa agc            3339
```

|  |  |  |  |  |  |  |  |  |  |  |  |  |
|---|---|---|---|---|---|---|---|---|---|---|---|---|
| Leu | Asn | Thr | Glu | Asp | Phe | Ser | Ser | Glu | Ser | Asp | Leu | Glu | Glu | Ser |
|  | 1100 |  |  |  | 1105 |  |  |  | 1110 |  |  |  |

```
aaa gag aaa ctg aat gaa agc agt agc tca tca gaa ggt agc act        3384
Lys Glu Lys Leu Asn Glu Ser Ser Ser Ser Ser Glu Gly Ser Thr
    1115                1120                1125 gtg gac atc ggc gca cct gta gaa gaa cag ccc gta gtg gaa cct        3429
Val Asp Ile Gly Ala Pro Val Glu Glu Gln Pro Val Val Glu Pro
1130                1135                1140 gaa gaa act ctt gaa cca gaa gct tgt ttc act gaa ggc tgt gta        3474
Glu Glu Thr Leu Glu Pro Glu Ala Cys Phe Thr Glu Gly Cys Val
    1145                1150                1155 caa aga ttc aag tgt tgt caa atc aat gtg gaa gaa ggc aga gga        3519
Gln Arg Phe Lys Cys Cys Gln Ile Asn Val Glu Glu Gly Arg Gly
        1160                1165                1170 aaa caa tgg tgg aac ctg aga agg acg tgt ttc cga ata gtt gaa        3564
Lys Gln Trp Trp Asn Leu Arg Arg Thr Cys Phe Arg Ile Val Glu
    1175                1180                1185 cat aac tgg ttt gag acc ttc att gtt ttc atg att ctc ctt agt        3609
His Asn Trp Phe Glu Thr Phe Ile Val Phe Met Ile Leu Leu Ser
    1190                1195                1200 agt ggt gct ctg gca ttt gaa gat ata tat att gat cag cga aag        3654
Ser Gly Ala Leu Ala Phe Glu Asp Ile Tyr Ile Asp Gln Arg Lys
    1205                1210                1215 acg att aag acg atg ttg gaa tat gct gac aag gtt ttc act tac        3699
Thr Ile Lys Thr Met Leu Glu Tyr Ala Asp Lys Val Phe Thr Tyr
    1220                1225                1230 att ttc att ctg gaa atg ctt cta aaa tgg gtg gca tat ggc tat        3744
Ile Phe Ile Leu Glu Met Leu Leu Lys Trp Val Ala Tyr Gly Tyr
    1235                1240                1245 caa aca tat ttc acc aat gcc tgg tgt tgg ctg gac ttc tta att        3789
Gln Thr Tyr Phe Thr Asn Ala Trp Cys Trp Leu Asp Phe Leu Ile
    1250                1255                1260 gtt gat gtt tca ttg gtc agt tta aca gca aat gcc ttg ggt tac        3834
Val Asp Val Ser Leu Val Ser Leu Thr Ala Asn Ala Leu Gly Tyr
    1265                1270                1275 tca gaa ctt gga gcc atc aaa tct ctc agg aca cta aga gct ctg        3879
Ser Glu Leu Gly Ala Ile Lys Ser Leu Arg Thr Leu Arg Ala Leu
    1280                1285                1290 aga cct cta aga gcc tta tct cga ttt gaa ggg atg agg gtg gtt        3924
Arg Pro Leu Arg Ala Leu Ser Arg Phe Glu Gly Met Arg Val Val
    1295                1300                1305 gtg aat gcc ctt tta gga gca att cca tcc atc atg aat gtg ctt        3969
Val Asn Ala Leu Leu Gly Ala Ile Pro Ser Ile Met Asn Val Leu
    1310                1315                1320 ctg gtt tgt ctt ata ttc tgg cta att ttc agc atc atg ggc gta        4014
Leu Val Cys Leu Ile Phe Trp Leu Ile Phe Ser Ile Met Gly Val
    1325                1330                1335 aat ttg ttt gct ggc aaa ttc tac cac tgt att aac acc aca act        4059
Asn Leu Phe Ala Gly Lys Phe Tyr His Cys Ile Asn Thr Thr Thr
    1340                1345                1350 ggt gac agg ttt gac atc gaa gac gtg aat aat cat act gat tgc        4104
Gly Asp Arg Phe Asp Ile Glu Asp Val Asn Asn His Thr Asp Cys
    1355                1360                1365 cta aaa cta ata gaa aga aat gag act gct cga tgg aaa aat gtg        4149
Leu Lys Leu Ile Glu Arg Asn Glu Thr Ala Arg Trp Lys Asn Val
    1370                1375                1380 aaa gta aac ttt gat aat gta gga ttt ggg tat ctc tct ttg ctt        4194
Lys Val Asn Phe Asp Asn Val Gly Phe Gly Tyr Leu Ser Leu Leu
    1385                1390                1395
```

-continued

| | | | | | | | | | | | | | | | |
|---|---|---|---|---|---|---|---|---|---|---|---|---|---|---|---|
| caa | gtt | gcc | aca | ttc | aaa | gga | tgg | atg | gat | ata | atg | tat | gca | gca | 4239 |
| Gln | Val | Ala | Thr | Phe | Lys | Gly | Trp | Met | Asp | Ile | Met | Tyr | Ala | Ala | |
| | 1400 | | | | 1405 | | | | 1410 | | | | | | |
| gtt | gat | tcc | aga | aat | gtg | gaa | ctc | cag | cct | aag | tat | gaa | gaa | agt | 4284 |
| Val | Asp | Ser | Arg | Asn | Val | Glu | Leu | Gln | Pro | Lys | Tyr | Glu | Glu | Ser | |
| 1415 | | | | | 1420 | | | | | 1425 | | | | | |
| ctg | tac | atg | tat | ctt | tac | ttt | gtt | att | ttc | atc | atc | ttt | ggg | tcc | 4329 |
| Leu | Tyr | Met | Tyr | Leu | Tyr | Phe | Val | Ile | Phe | Ile | Ile | Phe | Gly | Ser | |
| 1430 | | | | | 1435 | | | | 1440 | | | | | | |
| ttc | ttc | acc | ttg | aac | ctg | ttt | att | ggt | gtc | atc | ata | gat | aat | ttc | 4374 |
| Phe | Phe | Thr | Leu | Asn | Leu | Phe | Ile | Gly | Val | Ile | Ile | Asp | Asn | Phe | |
| | 1445 | | | | 1450 | | | | 1455 | | | | | | |
| aac | cag | cag | aaa | aag | aag | ttt | gga | ggt | caa | gac | atc | ttt | atg | aca | 4419 |
| Asn | Gln | Gln | Lys | Lys | Lys | Phe | Gly | Gly | Gln | Asp | Ile | Phe | Met | Thr | |
| 1460 | | | | | 1465 | | | | 1470 | | | | | | |
| gaa | gaa | cag | aag | aaa | tac | tat | aat | gca | atg | aaa | aaa | tta | gga | tcg | 4464 |
| Glu | Glu | Gln | Lys | Lys | Tyr | Tyr | Asn | Ala | Met | Lys | Lys | Leu | Gly | Ser | |
| 1475 | | | | | 1480 | | | | | 1485 | | | | | |
| aaa | aaa | ccg | caa | aag | cct | ata | cct | cga | cca | gga | aac | aaa | ttt | caa | 4509 |
| Lys | Lys | Pro | Gln | Lys | Pro | Ile | Pro | Arg | Pro | Gly | Asn | Lys | Phe | Gln | |
| | 1490 | | | | 1495 | | | | 1500 | | | | | | |
| gga | atg | gtc | ttt | gac | ttc | gta | acc | aga | caa | gtt | ttt | gac | ata | agc | 4554 |
| Gly | Met | Val | Phe | Asp | Phe | Val | Thr | Arg | Gln | Val | Phe | Asp | Ile | Ser | |
| 1505 | | | | | 1510 | | | | | 1515 | | | | | |
| atc | atg | att | ctc | atc | tgt | ctt | aac | atg | gtc | aca | atg | atg | gtg | gaa | 4599 |
| Ile | Met | Ile | Leu | Ile | Cys | Leu | Asn | Met | Val | Thr | Met | Met | Val | Glu | |
| 1520 | | | | | 1525 | | | | | 1530 | | | | | |
| aca | gat | gac | cag | agt | gaa | tat | gtg | act | acc | att | ttg | tca | cgc | atc | 4644 |
| Thr | Asp | Asp | Gln | Ser | Glu | Tyr | Val | Thr | Thr | Ile | Leu | Ser | Arg | Ile | |
| 1535 | | | | | 1540 | | | | | 1545 | | | | | |
| aat | ctg | gtg | ttc | att | gtg | cta | ttt | act | gga | gag | tgt | gta | ctg | aaa | 4689 |
| Asn | Leu | Val | Phe | Ile | Val | Leu | Phe | Thr | Gly | Glu | Cys | Val | Leu | Lys | |
| 1550 | | | | | 1555 | | | | | 1560 | | | | | |
| ctc | atc | tct | cta | cgc | cat | tat | tat | ttt | acc | att | gga | tgg | aat | att | 4734 |
| Leu | Ile | Ser | Leu | Arg | His | Tyr | Tyr | Phe | Thr | Ile | Gly | Trp | Asn | Ile | |
| 1565 | | | | | 1570 | | | | | 1575 | | | | | |
| ttt | gat | ttt | gtg | gtt | gtc | att | ctc | tcc | att | gta | ggt | atg | ttt | ctt | 4779 |
| Phe | Asp | Phe | Val | Val | Val | Ile | Leu | Ser | Ile | Val | Gly | Met | Phe | Leu | |
| 1580 | | | | | 1585 | | | | | 1590 | | | | | |
| gcc | gag | ctg | ata | gaa | aag | tat | ttc | gtg | tcc | cct | acc | ctg | ttc | cga | 4824 |
| Ala | Glu | Leu | Ile | Glu | Lys | Tyr | Phe | Val | Ser | Pro | Thr | Leu | Phe | Arg | |
| 1595 | | | | | 1600 | | | | | 1605 | | | | | |
| gtg | atc | cgt | ctt | gct | agg | att | ggc | cga | atc | cta | cgt | ctg | atc | aaa | 4869 |
| Val | Ile | Arg | Leu | Ala | Arg | Ile | Gly | Arg | Ile | Leu | Arg | Leu | Ile | Lys | |
| 1610 | | | | | 1615 | | | | | 1620 | | | | | |
| gga | gca | aag | ggg | atc | cgc | acg | ctg | ctc | ttt | gct | ttg | atg | atg | tcc | 4914 |
| Gly | Ala | Lys | Gly | Ile | Arg | Thr | Leu | Leu | Phe | Ala | Leu | Met | Met | Ser | |
| 1625 | | | | | 1630 | | | | | 1635 | | | | | |
| ctt | cct | gcg | ttg | ttt | aac | atc | ggc | ctc | ctc | ttc | cta | gtc | atg | | 4959 |
| Leu | Pro | Ala | Leu | Phe | Asn | Ile | Gly | Leu | Leu | Phe | Leu | Val | Met | | |
| 1640 | | | | | 1645 | | | | | 1650 | | | | | |
| ttc | atc | tac | gcc | atc | ttt | ggg | atg | tcc | aac | ttt | gcc | tat | gtt | aag | 5004 |
| Phe | Ile | Tyr | Ala | Ile | Phe | Gly | Met | Ser | Asn | Phe | Ala | Tyr | Val | Lys | |
| 1655 | | | | | 1660 | | | | | 1665 | | | | | |
| agg | gaa | gtt | ggg | atc | gat | gac | atg | ttc | aac | ttt | gag | acc | ttt | ggc | 5049 |
| Arg | Glu | Val | Gly | Ile | Asp | Asp | Met | Phe | Asn | Phe | Glu | Thr | Phe | Gly | |
| 1670 | | | | | 1675 | | | | | 1680 | | | | | |
| aac | agc | atg | atc | tgc | cta | ttc | caa | att | aca | acc | tct | gct | ggc | tgg | 5094 |
| Asn | Ser | Met | Ile | Cys | Leu | Phe | Gln | Ile | Thr | Thr | Ser | Ala | Gly | Trp | |
| 1685 | | | | | 1690 | | | | | 1695 | | | | | |

| | | | | | | | | | | |
|---|---|---|---|---|---|---|---|---|---|---|
| gat | gga | ttg | cta | gca | ccc | att | ctc | aac | agt | aag | cca | ccc | gac | tgt | 5139 |
| Asp | Gly | Leu | Leu | Ala | Pro | Ile | Leu | Asn | Ser | Lys | Pro | Pro | Asp | Cys | |
| 1700 | | | | | 1705 | | | | | 1710 | | | | | |

```
gat gga ttg cta gca ccc att ctc aac agt aag cca ccc gac tgt      5139
Asp Gly Leu Leu Ala Pro Ile Leu Asn Ser Lys Pro Pro Asp Cys
    1700              1705              1710 gac cct aat aaa gtt aac cct gga agc tca gtt aag gga gac tgt      5184
Asp Pro Asn Lys Val Asn Pro Gly Ser Ser Val Lys Gly Asp Cys
    1715              1720              1725 ggg aac cca tct gtt gga att ttc ttt ttt gtc agt tac atc atc      5229
Gly Asn Pro Ser Val Gly Ile Phe Phe Phe Val Ser Tyr Ile Ile
    1730              1735              1740 ata tcc ttc ctg gtt gtg gtg aac atg tac atc gcg gtc atc ctg      5274
Ile Ser Phe Leu Val Val Val Asn Met Tyr Ile Ala Val Ile Leu
    1745              1750              1755 gag aac ttc agt gtt gct act gaa gaa agt gca gag cct ctg agt      5319
Glu Asn Phe Ser Val Ala Thr Glu Glu Ser Ala Glu Pro Leu Ser
    1760              1765              1770 gag gat gac ttt gag atg ttc tat gag gtt tgg gag aag ttt gat      5364
Glu Asp Asp Phe Glu Met Phe Tyr Glu Val Trp Glu Lys Phe Asp
    1775              1780              1785 ccc gat gca act cag ttc atg gaa ttt gaa aaa tta tct cag ttt      5409
Pro Asp Ala Thr Gln Phe Met Glu Phe Glu Lys Leu Ser Gln Phe
    1790              1795              1800 gca gct gcg ctt gaa ccg cct ctc aat ctg cca caa cca aac aaa      5454
Ala Ala Ala Leu Glu Pro Pro Leu Asn Leu Pro Gln Pro Asn Lys
    1805              1810              1815 ctc cag ctc att gcc atg gat ttg ccc atg gtg agt ggt gac cgg      5499
Leu Gln Leu Ile Ala Met Asp Leu Pro Met Val Ser Gly Asp Arg
    1820              1825              1830 atc cac tgt ctt gat atc tta ttt gct ttt aca aag cgg gtt cta      5544
Ile His Cys Leu Asp Ile Leu Phe Ala Phe Thr Lys Arg Val Leu
    1835              1840              1845 gga gag agt gga gag atg gat gct cta cga ata cag atg gaa gag      5589
Gly Glu Ser Gly Glu Met Asp Ala Leu Arg Ile Gln Met Glu Glu
    1850              1855              1860 cga ttc atg gct tcc aat cct tcc aag gtc tcc tat cag cca atc      5634
Arg Phe Met Ala Ser Asn Pro Ser Lys Val Ser Tyr Gln Pro Ile
    1865              1870              1875 act act act tta aaa cga aaa caa gag gaa gta tct gct gtc att      5679
Thr Thr Thr Leu Lys Arg Lys Gln Glu Glu Val Ser Ala Val Ile
    1880              1885              1890 att cag cgt gct tac aga cgc cac ctt tta aag cga act gta aaa      5724
Ile Gln Arg Ala Tyr Arg Arg His Leu Leu Lys Arg Thr Val Lys
    1895              1900              1905 caa gct tcc ttt acg tac aat aaa aac aaa atc aaa ggt ggg gct      5769
Gln Ala Ser Phe Thr Tyr Asn Lys Asn Lys Ile Lys Gly Gly Ala
    1910              1915              1920 aat ctt ctt ata aaa gaa gac atg ata att gac aga ata aat gaa      5814
Asn Leu Leu Ile Lys Glu Asp Met Ile Ile Asp Arg Ile Asn Glu
    1925              1930              1935 aac tct att aca gaa aaa act gat ctg acc atg tcc act gca gct      5859
Asn Ser Ile Thr Glu Lys Thr Asp Leu Thr Met Ser Thr Ala Ala
    1940              1945              1950 tgt cca cct tcc tat gac cgg gtg aca aag cca att gtg gaa aaa      5904
Cys Pro Pro Ser Tyr Asp Arg Val Thr Lys Pro Ile Val Glu Lys
    1955              1960              1965 cat gag caa gaa ggc aaa gat gaa aaa gcc aaa ggg aaa taa           5946
His Glu Gln Glu Gly Lys Asp Glu Lys Ala Lys Gly Lys
    1970              1975              1980
```

<210> SEQ ID NO 23

```
<211> LENGTH: 1981
<212> TYPE: PRT
<213> ORGANISM: Homo sapiens

<400> SEQUENCE: 23

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
```

-continued

```
            385                 390                 395                 400
Ile Phe Phe Val Leu Val Ile Phe Leu Gly Ser Phe Tyr Leu Ile Asn
                405                 410                 415
Leu Ile Leu Ala Val Val Ala Met Ala Tyr Glu Glu Gln Asn Gln Ala
                420                 425                 430
Thr Leu Glu Glu Ala Glu Gln Lys Glu Ala Glu Phe Gln Gln Met Ile
                435                 440                 445
Glu Gln Leu Lys Lys Gln Gln Glu Ala Ala Gln Gln Ala Ala Thr Ala
        450                 455                 460
Thr Ala Ser Glu His Ser Arg Glu Pro Ser Ala Ala Gly Arg Leu Ser
465                 470                 475                 480
Asp Ser Ser Ser Glu Ala Ser Lys Leu Ser Ser Lys Ser Ala Lys Glu
                485                 490                 495
Arg Arg Asn Arg Arg Lys Lys Arg Lys Gln Lys Glu Gln Ser Gly Gly
                500                 505                 510
Glu Glu Lys Asp Glu Asp Glu Phe Gln Lys Ser Glu Ser Glu Asp Ser
                515                 520                 525
Ile Arg Arg Lys Gly Phe Arg Phe Ser Ile Glu Gly Asn Arg Leu Thr
        530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
                580                 585                 590
Asp Glu His Ser Thr Phe Glu Asp Asn Glu Ser Arg Arg Asp Ser Leu
                595                 600                 605
Phe Val Pro Arg Arg His Gly Glu Arg Arg Asn Ser Asn Leu Ser Gln
                610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Gly Thr Thr
                645                 650                 655
Thr Glu Thr Glu Met Arg Lys Arg Arg Ser Ser Ser Phe His Val Ser
                660                 665                 670
Met Asp Phe Leu Glu Asp Pro Ser Gln Arg Gln Arg Ala Met Ser Ile
                675                 680                 685
Ala Ser Ile Leu Thr Asn Thr Val Glu Glu Leu Glu Glu Ser Arg Gln
        690                 695                 700
Lys Cys Pro Pro Cys Trp Tyr Lys Phe Ser Asn Ile Phe Leu Ile Trp
705                 710                 715                 720
Asp Cys Ser Pro Tyr Trp Leu Lys Val Lys His Val Val Asn Leu Val
                725                 730                 735
Val Met Asp Pro Phe Val Asp Leu Ala Ile Thr Ile Cys Ile Val Leu
                740                 745                 750
Asn Thr Leu Phe Met Ala Met Glu His Tyr Pro Met Thr Asp His Phe
                755                 760                 765
Asn Asn Val Leu Thr Val Gly Asn Leu Val Phe Thr Gly Ile Phe Thr
                770                 775                 780
Ala Glu Met Phe Leu Lys Ile Ile Ala Met Asp Pro Tyr Tyr Tyr Phe
785                 790                 795                 800
Gln Glu Gly Trp Asn Ile Phe Asp Gly Phe Ile Val Thr Leu Ser Leu
                805                 810                 815
```

-continued

```
Val Glu Leu Gly Leu Ala Asn Val Glu Gly Leu Ser Val Leu Arg Ser
            820                 825                 830

Phe Arg Leu Leu Arg Val Phe Lys Leu Ala Lys Ser Trp Pro Thr Leu
            835                 840                 845

Asn Met Leu Ile Lys Ile Ile Gly Asn Ser Val Gly Ala Leu Gly Asn
            850                 855                 860

Leu Thr Leu Val Leu Ala Ile Ile Val Phe Ile Phe Ala Val Val Gly
865                 870                 875                 880

Met Gln Leu Phe Gly Lys Ser Tyr Lys Asp Cys Val Cys Lys Ile Ala
                    885                 890                 895

Ser Asp Cys Gln Leu Pro Arg Trp His Met Asn Asp Phe Phe His Ser
            900                 905                 910

Phe Leu Ile Val Phe Arg Val Leu Cys Gly Glu Trp Ile Glu Thr Met
            915                 920                 925

Trp Asp Cys Met Glu Val Ala Gly Gln Ala Met Cys Leu Thr Val Phe
            930                 935                 940

Met Met Val Met Val Ile Gly Asn Leu Val Val Leu Asn Leu Phe Leu
945                 950                 955                 960

Ala Leu Leu Leu Ser Ser Phe Ser Ala Asp Asn Leu Ala Ala Thr Asp
                    965                 970                 975

Asp Asp Asn Glu Met Asn Asn Leu Gln Ile Ala Val Asp Arg Met His
            980                 985                 990

Lys Gly Val Ala Tyr Val Lys Arg  Lys Ile Tyr Glu Phe  Ile Gln Gln
            995                 1000                 1005

Ser Phe Ile Arg Lys Gln Lys  Ile Leu Asp Glu Ile   Lys Pro Leu
    1010                 1015                 1020

Asp Asp  Leu Asn Asn Lys Lys  Asp Ser Cys Met Ser   Asn His Thr
    1025                 1030                 1035

Ala Glu Ile Gly Lys Asp Leu  Asp Tyr Leu Lys Asp   Val Asn Gly
    1040                 1045                 1050

Thr Thr Ser Gly Ile Gly Thr  Gly Ser Ser Val Glu   Lys Tyr Ile
    1055                 1060                 1065

Ile Asp Glu Ser Asp Tyr Met  Ser Phe Ile Asn Asn   Pro Ser Leu
    1070                 1075                 1080

Thr Val Thr Val Pro Ile Ala  Val Gly Glu Ser Asp   Phe Glu Asn
    1085                 1090                 1095

Leu Asn Thr Glu Asp Phe Ser  Ser Glu Ser Asp Leu   Glu Glu Ser
    1100                 1105                 1110

Lys Glu Lys Leu Asn Glu Ser  Ser Ser Ser Ser Glu   Gly Ser Thr
    1115                 1120                 1125

Val Asp Ile Gly Ala Pro Val  Glu Glu Gln Pro Val   Val Glu Pro
    1130                 1135                 1140

Glu Glu Thr Leu Glu Pro Glu  Ala Cys Phe Thr Glu   Gly Cys Val
    1145                 1150                 1155

Gln Arg Phe Lys Cys Cys Gln  Ile Asn Val Glu Glu   Gly Arg Gly
    1160                 1165                 1170

Lys Gln Trp Trp Asn Leu Arg  Arg Thr Cys Phe Arg   Ile Val Glu
    1175                 1180                 1185

His Asn Trp Phe Glu Thr Phe  Ile Val Phe Met Ile   Leu Leu Ser
    1190                 1195                 1200

Ser Gly Ala Leu Ala Phe Glu  Asp Ile Tyr Ile Asp   Gln Arg Lys
    1205                 1210                 1215
```

-continued

Thr Ile Lys Thr Met Leu Glu Tyr Ala Asp Lys Val Phe Thr Tyr
1220            1225                1230

Ile Phe Ile Leu Glu Met Leu Leu Lys Trp Val Ala Tyr Gly Tyr
1235            1240                1245

Gln Thr Tyr Phe Thr Asn Ala Trp Cys Trp Leu Asp Phe Leu Ile
1250            1255                1260

Val Asp Val Ser Leu Val Ser Leu Thr Ala Asn Ala Leu Gly Tyr
1265            1270                1275

Ser Glu Leu Gly Ala Ile Lys Ser Leu Arg Thr Leu Arg Ala Leu
1280            1285                1290

Arg Pro Leu Arg Ala Leu Ser Arg Phe Glu Gly Met Arg Val Val
1295            1300                1305

Val Asn Ala Leu Leu Gly Ala Ile Pro Ser Ile Met Asn Val Leu
1310            1315                1320

Leu Val Cys Leu Ile Phe Trp Leu Ile Phe Ser Ile Met Gly Val
1325            1330                1335

Asn Leu Phe Ala Gly Lys Phe Tyr His Cys Ile Asn Thr Thr Thr
1340            1345                1350

Gly Asp Arg Phe Asp Ile Glu Asp Val Asn Asn His Thr Asp Cys
1355            1360                1365

Leu Lys Leu Ile Glu Arg Asn Glu Thr Ala Arg Trp Lys Asn Val
1370            1375                1380

Lys Val Asn Phe Asp Asn Val Gly Phe Gly Tyr Leu Ser Leu Leu
1385            1390                1395

Gln Val Ala Thr Phe Lys Gly Trp Met Asp Ile Met Tyr Ala Ala
1400            1405                1410

Val Asp Ser Arg Asn Val Glu Leu Gln Pro Lys Tyr Glu Glu Ser
1415            1420                1425

Leu Tyr Met Tyr Leu Tyr Phe Val Ile Phe Ile Ile Phe Gly Ser
1430            1435                1440

Phe Phe Thr Leu Asn Leu Phe Ile Gly Val Ile Ile Asp Asn Phe
1445            1450                1455

Asn Gln Gln Lys Lys Lys Phe Gly Gly Gln Asp Ile Phe Met Thr
1460            1465                1470

Glu Glu Gln Lys Lys Tyr Tyr Asn Ala Met Lys Lys Leu Gly Ser
1475            1480                1485

Lys Lys Pro Gln Lys Pro Ile Pro Arg Pro Gly Asn Lys Phe Gln
1490            1495                1500

Gly Met Val Phe Asp Phe Val Thr Arg Gln Val Phe Asp Ile Ser
1505            1510                1515

Ile Met Ile Leu Ile Cys Leu Asn Met Val Thr Met Met Val Glu
1520            1525                1530

Thr Asp Asp Gln Ser Glu Tyr Val Thr Thr Ile Leu Ser Arg Ile
1535            1540                1545

Asn Leu Val Phe Ile Val Leu Phe Thr Gly Glu Cys Val Leu Lys
1550            1555                1560

Leu Ile Ser Leu Arg His Tyr Tyr Phe Thr Ile Gly Trp Asn Ile
1565            1570                1575

Phe Asp Phe Val Val Val Ile Leu Ser Ile Val Gly Met Phe Leu
1580            1585                1590

Ala Glu Leu Ile Glu Lys Tyr Phe Val Ser Pro Thr Leu Phe Arg
1595            1600                1605

Val Ile Arg Leu Ala Arg Ile Gly Arg Ile Leu Arg Leu Ile Lys

```
                1610                1615                1620

Gly Ala Lys Gly Ile Arg Thr Leu Leu Phe Ala Leu Met Met Ser
    1625                1630                1635

Leu Pro Ala Leu Phe Asn Ile Gly Leu Leu Phe Leu Val Met
    1640                1645                1650

Phe Ile Tyr Ala Ile Phe Gly Met Ser Asn Phe Ala Tyr Val Lys
    1655                1660                1665

Arg Glu Val Gly Ile Asp Asp Met Phe Asn Phe Glu Thr Phe Gly
    1670                1675                1680

Asn Ser Met Ile Cys Leu Phe Gln Ile Thr Thr Ser Ala Gly Trp
    1685                1690                1695

Asp Gly Leu Leu Ala Pro Ile Leu Asn Ser Lys Pro Pro Asp Cys
    1700                1705                1710

Asp Pro Asn Lys Val Asn Pro Gly Ser Ser Val Lys Gly Asp Cys
    1715                1720                1725

Gly Asn Pro Ser Val Gly Ile Phe Phe Phe Val Ser Tyr Ile Ile
    1730                1735                1740

Ile Ser Phe Leu Val Val Val Asn Met Tyr Ile Ala Val Ile Leu
    1745                1750                1755

Glu Asn Phe Ser Val Ala Thr Glu Glu Ser Ala Glu Pro Leu Ser
    1760                1765                1770

Glu Asp Asp Phe Glu Met Phe Tyr Glu Val Trp Glu Lys Phe Asp
    1775                1780                1785

Pro Asp Ala Thr Gln Phe Met Glu Phe Glu Lys Leu Ser Gln Phe
    1790                1795                1800

Ala Ala Ala Leu Glu Pro Pro Leu Asn Leu Pro Gln Pro Asn Lys
    1805                1810                1815

Leu Gln Leu Ile Ala Met Asp Leu Pro Met Val Ser Gly Asp Arg
    1820                1825                1830

Ile His Cys Leu Asp Ile Leu Phe Ala Phe Thr Lys Arg Val Leu
    1835                1840                1845

Gly Glu Ser Gly Glu Met Asp Ala Leu Arg Ile Gln Met Glu Glu
    1850                1855                1860

Arg Phe Met Ala Ser Asn Pro Ser Lys Val Ser Tyr Gln Pro Ile
    1865                1870                1875

Thr Thr Thr Leu Lys Arg Lys Gln Glu Glu Val Ser Ala Val Ile
    1880                1885                1890

Ile Gln Arg Ala Tyr Arg Arg His Leu Leu Lys Arg Thr Val Lys
    1895                1900                1905

Gln Ala Ser Phe Thr Tyr Asn Lys Asn Lys Ile Lys Gly Gly Ala
    1910                1915                1920

Asn Leu Leu Ile Lys Glu Asp Met Ile Ile Asp Arg Ile Asn Glu
    1925                1930                1935

Asn Ser Ile Thr Glu Lys Thr Asp Leu Thr Met Ser Thr Ala Ala
    1940                1945                1950

Cys Pro Pro Ser Tyr Asp Arg Val Thr Lys Pro Ile Val Glu Lys
    1955                1960                1965

His Glu Gln Glu Gly Lys Asp Glu Lys Ala Lys Gly Lys
    1970                1975                1980

<210> SEQ ID NO 24
<211> LENGTH: 33
<212> TYPE: DNA
<213> ORGANISM: Homo sapiens
```

```
<220> FEATURE:
<221> NAME/KEY: CDS
<222> LOCATION: (1)..(33)

<400> SEQUENCE: 24 gtg ata ata gat aag cca gct act gat gac aat                    33
Val Ile Ile Asp Lys Pro Ala Thr Asp Asp Asn
1               5                   10

<210> SEQ ID NO 25
<211> LENGTH: 11
<212> TYPE: PRT
<213> ORGANISM: Homo sapiens

<400> SEQUENCE: 25

Val Ile Ile Asp Lys Pro Ala Thr Asp Asp Asn
1               5                   10

<210> SEQ ID NO 26
<211> LENGTH: 84
<212> TYPE: DNA
<213> ORGANISM: Homo sapiens
<220> FEATURE:
<221> NAME/KEY: CDS
<222> LOCATION: (1)..(84)

<400> SEQUENCE: 26 gtt ggt gga cct tca gtt cct aca tcg cct gtt gga cag ctt ctg cca    48
Val Gly Gly Pro Ser Val Pro Thr Ser Pro Val Gly Gln Leu Leu Pro
1               5                   10                  15 gag gtg ata ata gat aag cca gct act gat gac aat                    84
Glu Val Ile Ile Asp Lys Pro Ala Thr Asp Asp Asn
            20                  25

<210> SEQ ID NO 27
<211> LENGTH: 28
<212> TYPE: PRT
<213> ORGANISM: Homo sapiens

<400> SEQUENCE: 27

Val Gly Gly Pro Ser Val Pro Thr Ser Pro Val Gly Gln Leu Leu Pro
1               5                   10                  15

Glu Val Ile Ile Asp Lys Pro Ala Thr Asp Asp Asn
            20                  25
```